US011919943B2

(12) United States Patent
Weber et al.

(10) Patent No.: US 11,919,943 B2
(45) Date of Patent: Mar. 5, 2024

(54) ANTI-BK VIRUS ANTIBODY MOLECULES

(71) Applicants: MEMO THERAPEUTICS AG, Schlieren (CH); UNIVERSITÄT BERN, Bern (CH); UNIVERSITÄT ZÜRICH, Zürich (CH)

(72) Inventors: Marcel Weber, Zürich (CH); Simone Schmitt, Dietikon (CH); Christoph Esslinger, Zürich (CH); Thomas Schachtner, Zürich (CH); Uyen Huynh-Do, Liebefeld (CH); Maurizio Provenzano, Birrwil (CH)

(73) Assignees: MEMO THERAPEUTICS AG, Schlieren (CH); UNIVERSITÄT BERN, Bern (CH); UNIVERSITÄT ZÜRICH, Zürich (CH)

( * ) Notice: Subject to any disclaimer, the term of this patent is extended or adjusted under 35 U.S.C. 154(b) by 0 days.

(21) Appl. No.: 18/049,559

(22) Filed: Oct. 25, 2022

(65) Prior Publication Data
US 2023/0192816 A1 Jun. 22, 2023

Related U.S. Application Data

(63) Continuation of application No. PCT/EP2021/065462, filed on Jun. 9, 2021.

(51) Int. Cl.
*C07K 16/08* (2006.01)
*A61P 31/20* (2006.01)
*C12N 15/63* (2006.01)

(52) U.S. Cl.
CPC ........... *C07K 16/084* (2013.01); *A61P 31/20* (2018.01); *C12N 15/63* (2013.01); *C07K 2317/35* (2013.01); *C07K 2317/565* (2013.01); *C07K 2317/92* (2013.01)

(58) Field of Classification Search
None
See application file for complete search history.

(56) References Cited

FOREIGN PATENT DOCUMENTS

| WO | WO-2014102399 A1 | 7/2014 | |
|----|---|---|---|
| WO | WO-2017046676 A1 * | 3/2017 | ............. A61K 39/42 |
| WO | WO-2019106578 A2 | 6/2019 | |
| WO | WO-2021250097 A1 | 12/2021 | |

OTHER PUBLICATIONS

Altschul, S.F., et al., "Basic Local Alignment Search Tool," Journal of Molecular Biology 215(3):403-410, Elsevier, Netherlands (Oct. 1990).
Bennett, S.M., et al., "BK Polyomavirus: Emerging Pathogen," Microbes and Infection 14(9):672-683, Elsevier, France (Aug. 2012).
Buck, C.B. and Thompson, C.D., "Production of Papillomavirus-based Gene Transfer Vectors," Current Protocols in Cell Biology 26:Unit 26.1, John Wiley, United States (Dec. 2007).
Buck, C.B., et al., "Arrangement of L2 Within the Papillomavirus Capsid," Journal of Virology 82(11):5190-5197, American Society For Microbiology, United States (Jun. 2008).
Caldas, C., et al., "Humanization of the Anti-CD18 Antibody 6.7: An Unexpected Effect of a FrameworkResidue in Binding to Antigen," Molecular Immunology 39(15):941-952, Pergamon Press, United Kingdom (May 2003).
Du, J., et al., "Molecular Basis of Recognition of Human Osteopontin by 23C3, a Potential Therapeutic Antibody for Treatment of Rheumatoid Arthritis," Journal of Molecular Biology 382(4):835-842, Elsevier, United Kingdom (Oct. 2008).
Hurdiss, D.L., et al., "New Structural Insights into the Genome and Minor Capsid Proteins of BK Polyomavirus using Cryo-Electron Microscopy," Structure 24(4):528-536, Cell Press, United States (Apr. 2016).
International Search Report and Written Opinion for International Application No. PCT/EP2021/065462, European Patent Office, Netherlands, dated Oct. 5, 2021, 19 pages.
Kable, K., et al., "Clearance of BK Virus Nephropathy by Combination Antiviral Therapy With Intravenous Immunoglobulin," Transplantation Direct 3(4):e142, Wolters Kluwer, United States (Mar. 2017).
Karlin, S. and Altschul, S.F., "Applications and Statistics for Multiple High-scoring Segments in Molecular Sequences," Proceedings of the National Academy of Sciences of the United States of America 90(12):5873-5877, National Academy of Sciences, United States (Jun. 1993).
Martelli, F., et al., "BK Polyomavirus MicroRNA Levels in Exosomes Are Modulated by Non-Coding Control Region Activity and Down-Regulate Viral Replication When Delivered to Non-Infected Cells Prior to Infection," Viruses 10(9):466, MDPI, Switzerland (Aug. 2018).
Panka, D.J., et al., "Variable Region Framework Differences Result in Decreased or Increased Affinity of Variant Anti-digoxin Antibodies," Proceedings of the National Academy of Sciences USA 85(9):3080-3084, National Academy of Sciences, United States (May 1988).
Pastrana, D.V., et al., "BK Polyomavirus Genotypes Represent Distinct Serotypes With Distinct Entry Tropism," Journal of Virology 87(18):10105-10113, American Society For Microbiology, United States (Sep. 2013).
Pérez De La Lastra, J.M., et al., "Epitope Mapping of 10 Monoclonal Antibodies Against the Pig Analogue of Human Membrane Cofactor Protein (MCP)," Immunology 96(4):663-670, Blackwell Scientific Publications, United Kingdom (Apr. 1999).
Ramos, E., et al., "The Decade of Polyomavirus BK-associated Nephropathy: State of Affairs," Transplantation 87(5):621-630, Lippincott Williams & Wilkins, United States (Mar. 2009).

(Continued)

*Primary Examiner* — Michael Szperka
(74) *Attorney, Agent, or Firm* — STERNE, KESSLER, GOLDSTEIN & FOX P.L.L.C.

(57) ABSTRACT

Anti-BK virus antibody molecules or binding fragments thereof are disclosed. These Anti-BK virus antibody molecules or binding fragments can be used in the treatment or prevention of BK virus infection and/or BK virus associated disorder.

16 Claims, 21 Drawing Sheets

Specification includes a Sequence Listing.

(56) References Cited

OTHER PUBLICATIONS

Randhawa, P., et al., "Identification of Species-specific and Cross-reactive Epitopes in Human Polyomavirus Capsids Using Monoclonal Antibodies," The Journal of General Virology 90(Pt 3):634-639, Microbiology Society, United Kingdom (Mar. 2009).

Rinaldo, C.H., et al., "The Human Polyomavirus BK (BKPyV): Virological Background and Clinical Implications," APMIS 121(8):728-745, Munksgaard, Denmark (Aug. 2013).

Santeusanio, A.D., et al., "Antiviral Treatment of BK Virus Viremia After Kidney Transplantation," American Journal of Health-System Pharmacy 74(24):2037-2045, Oxford University Press, United Kingdom (Dec. 2017).

Xiang, J.H., et al., "Modification in Framework Region I Results in a Decreased Affinity of Chimeric Anti-TAG72 Antibody," Molecular Immunology 28(1-2):141-148, Pergamon Press, United Kingdom (Jan. 1991).

\* cited by examiner

Figure 1
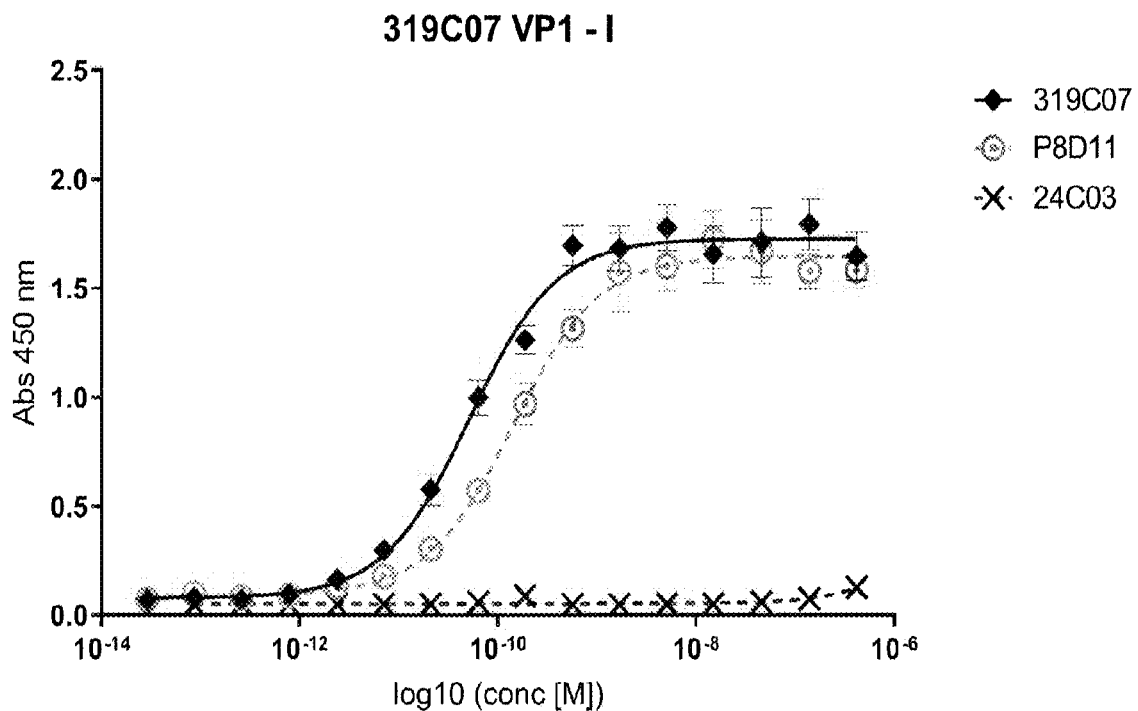
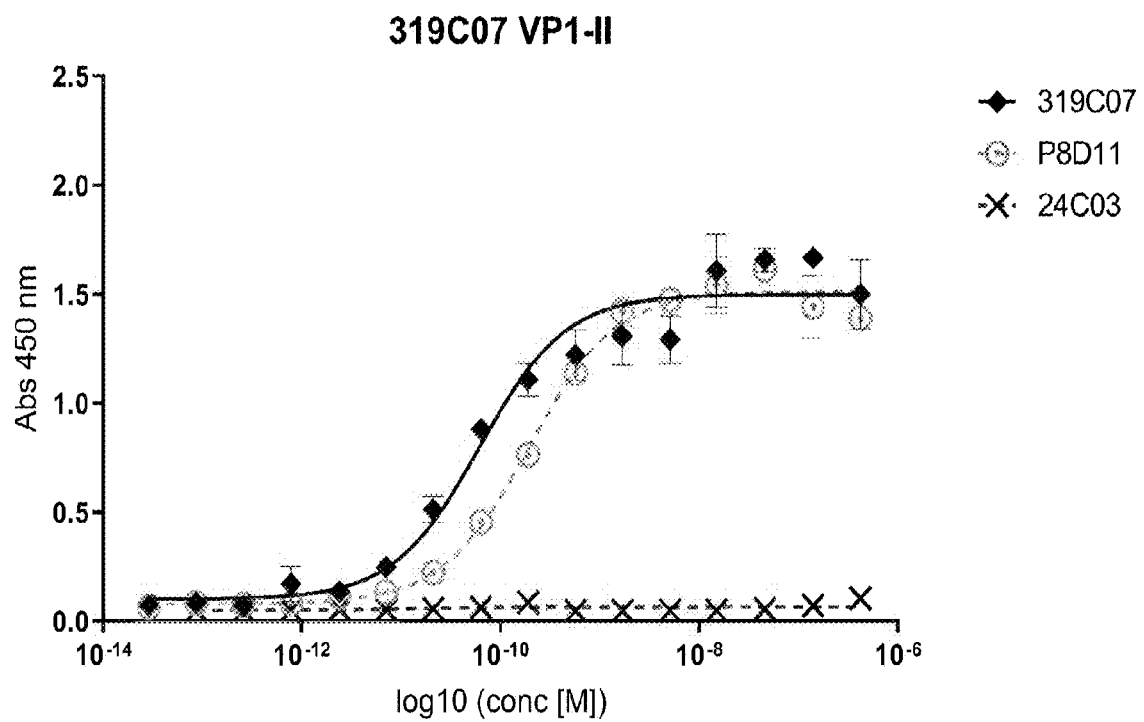

Figure 1 - continued
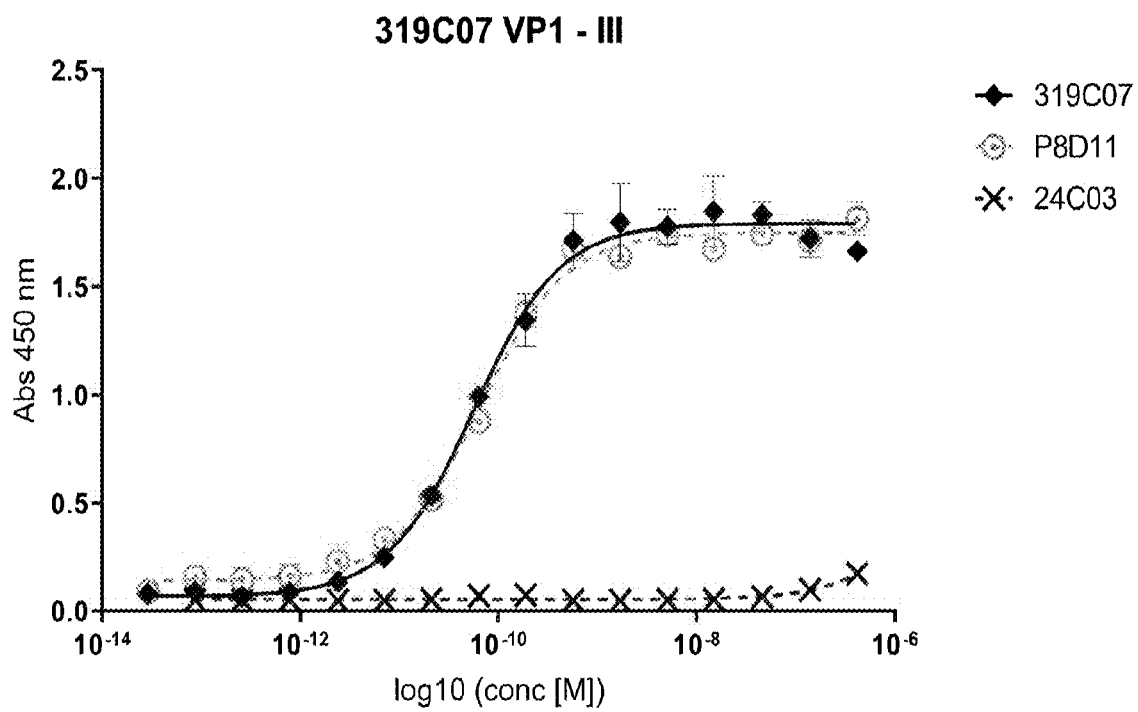
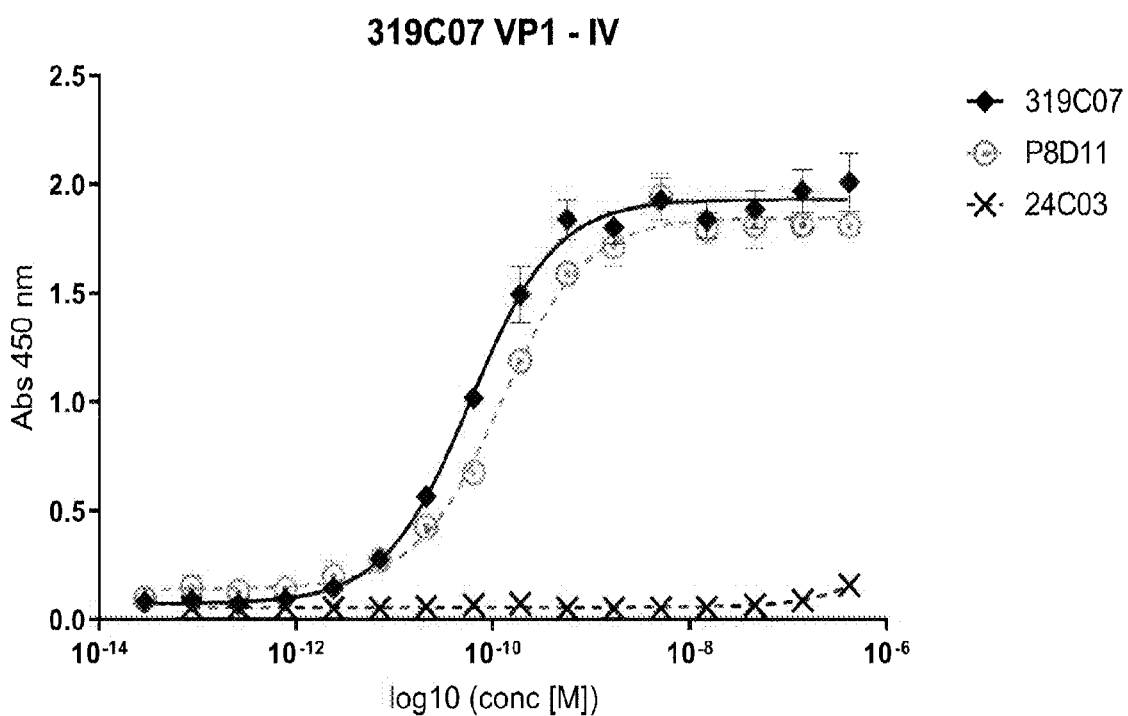

Figure 1 - continued
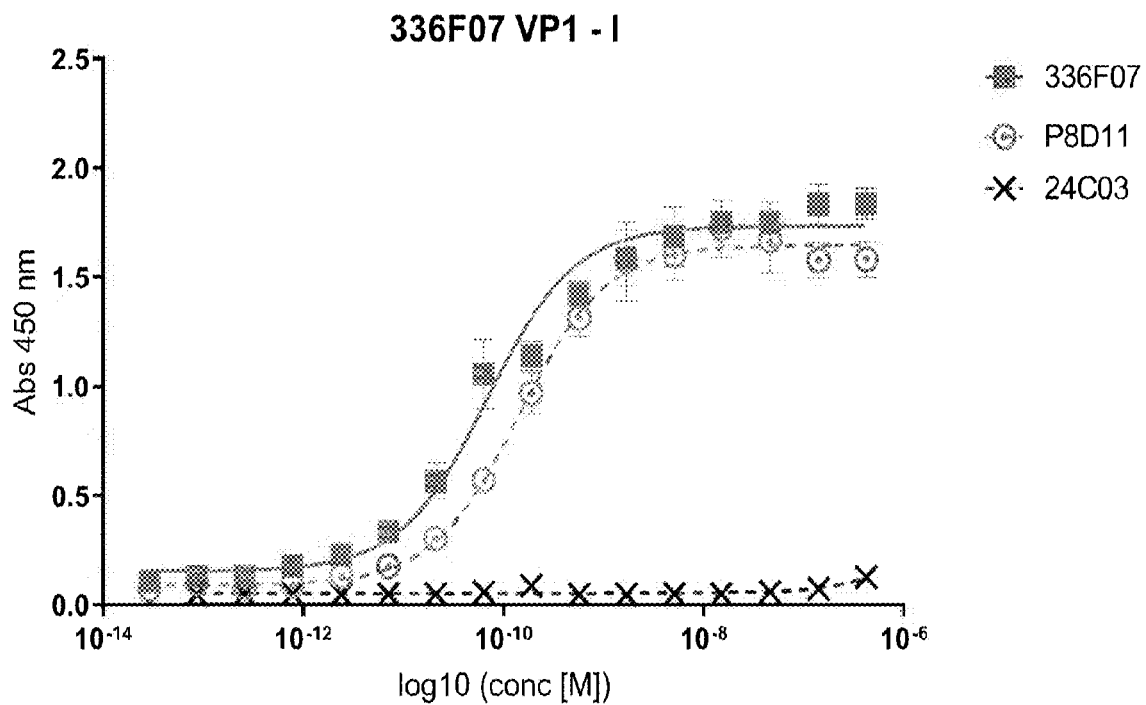
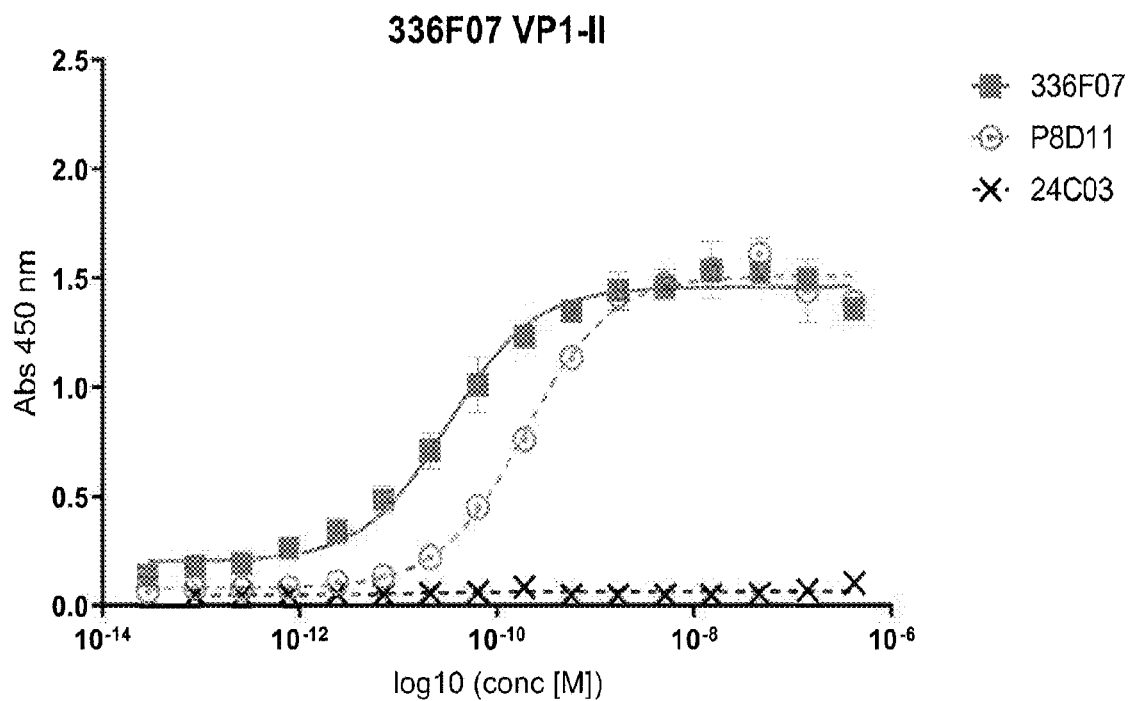

Figure 1 - continued
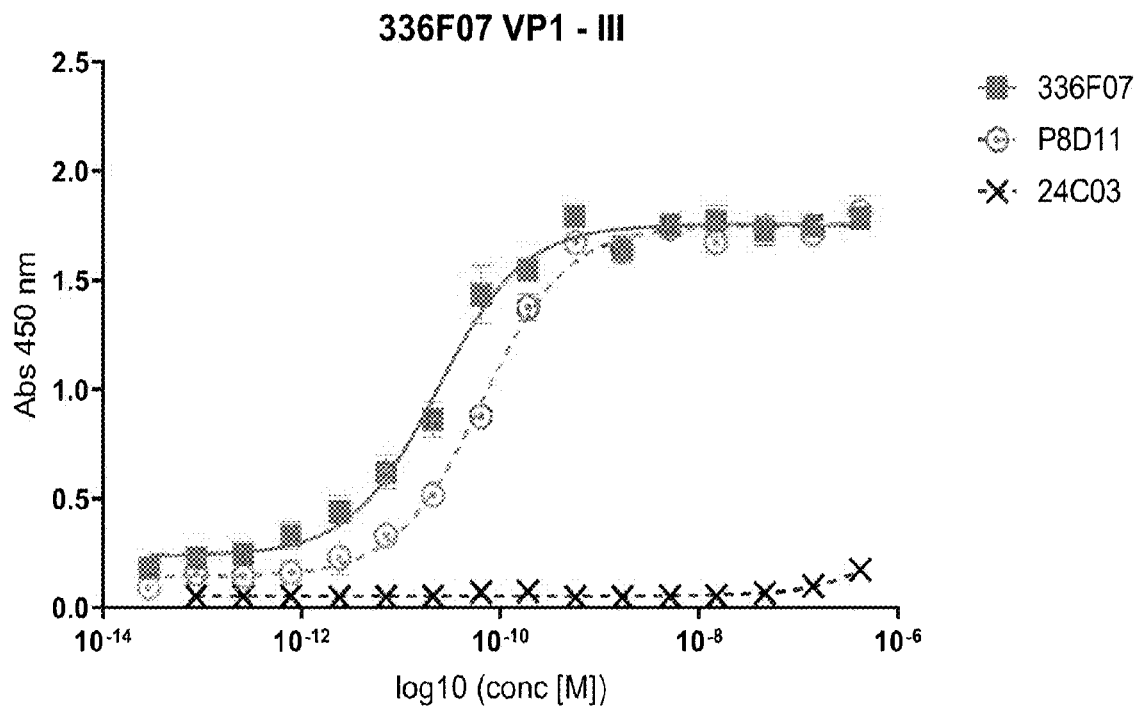
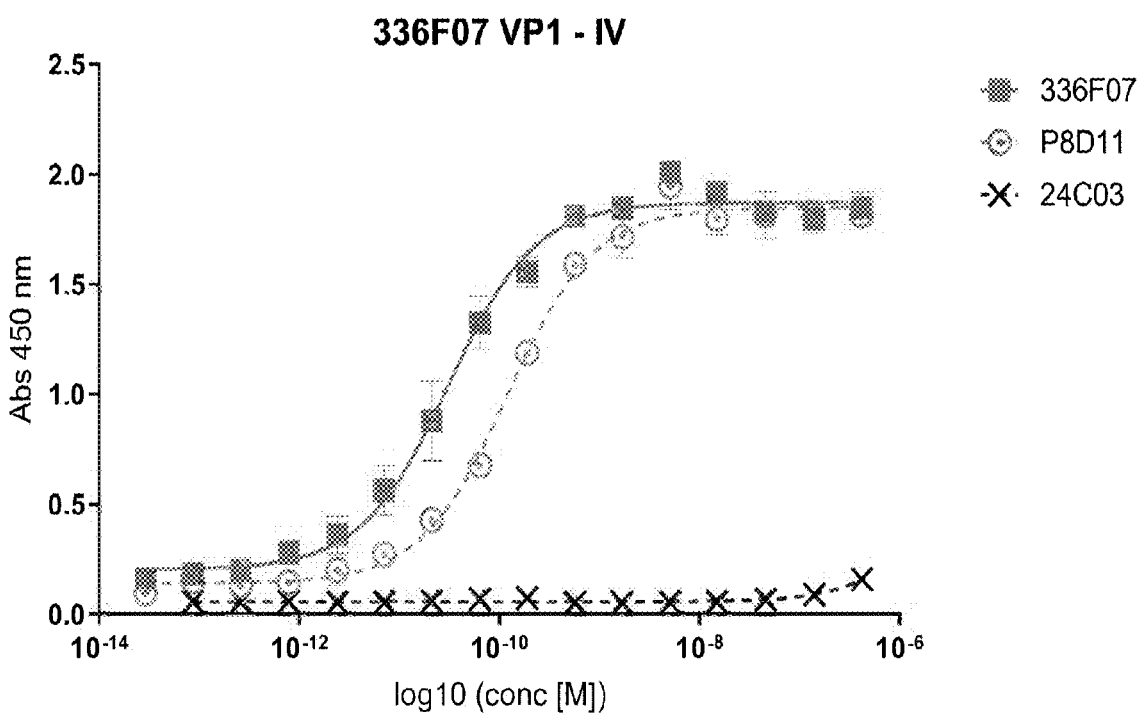

Figure 2
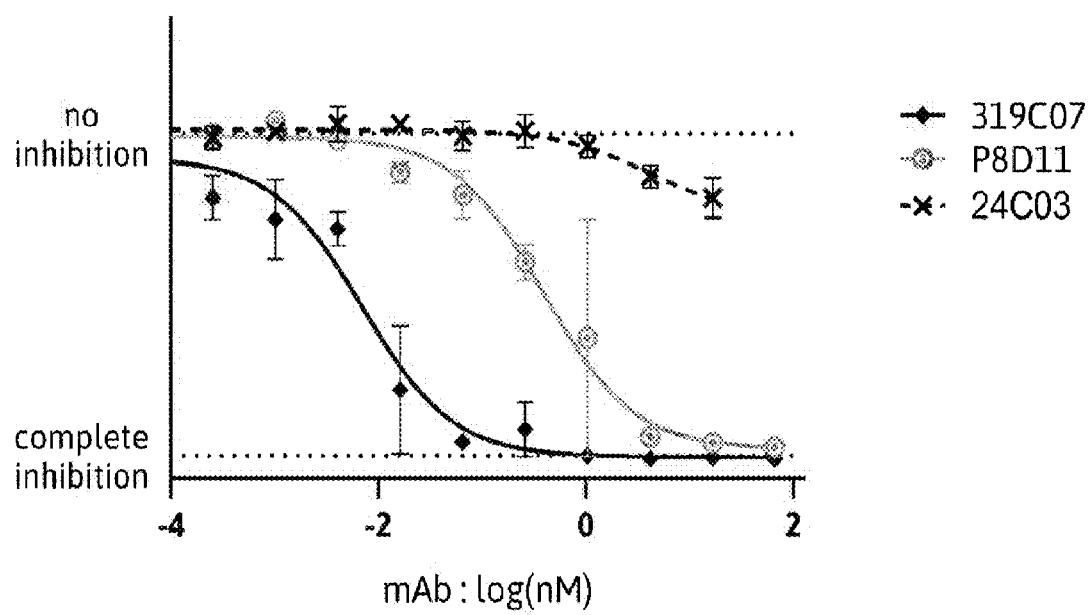
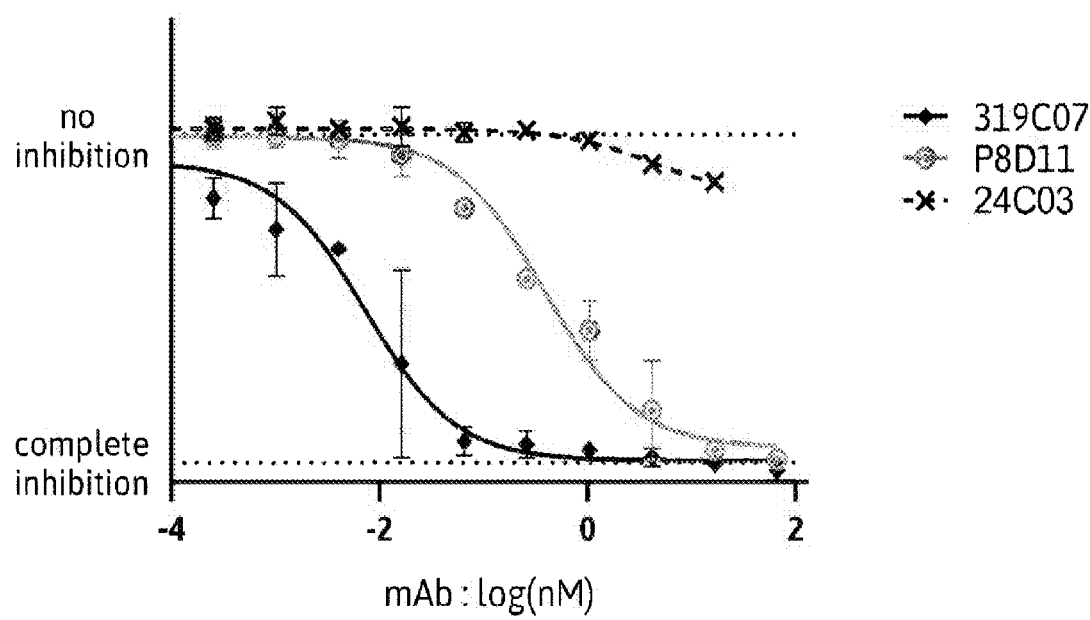

Figure 2 - continued
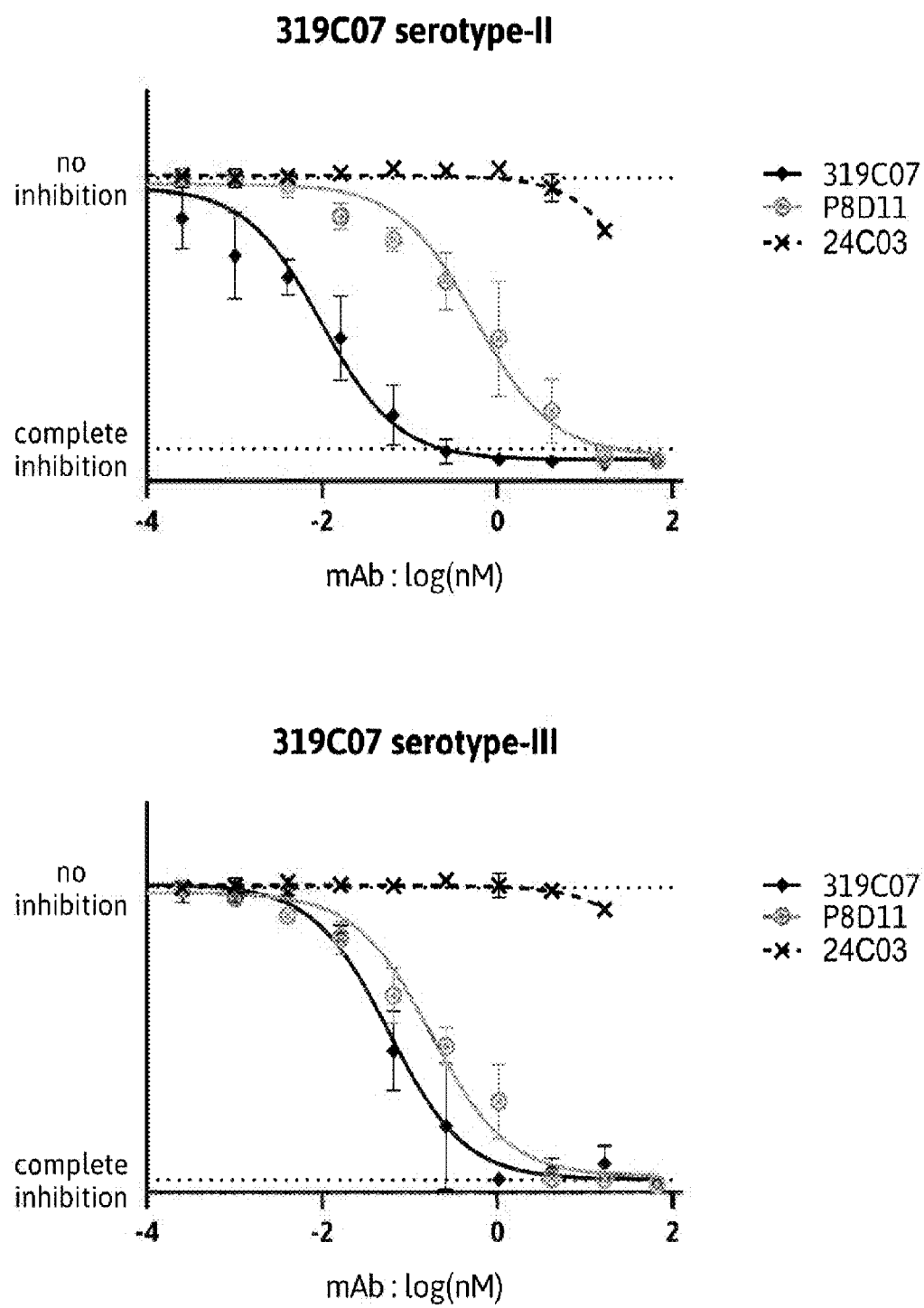

Figure 2 - continued
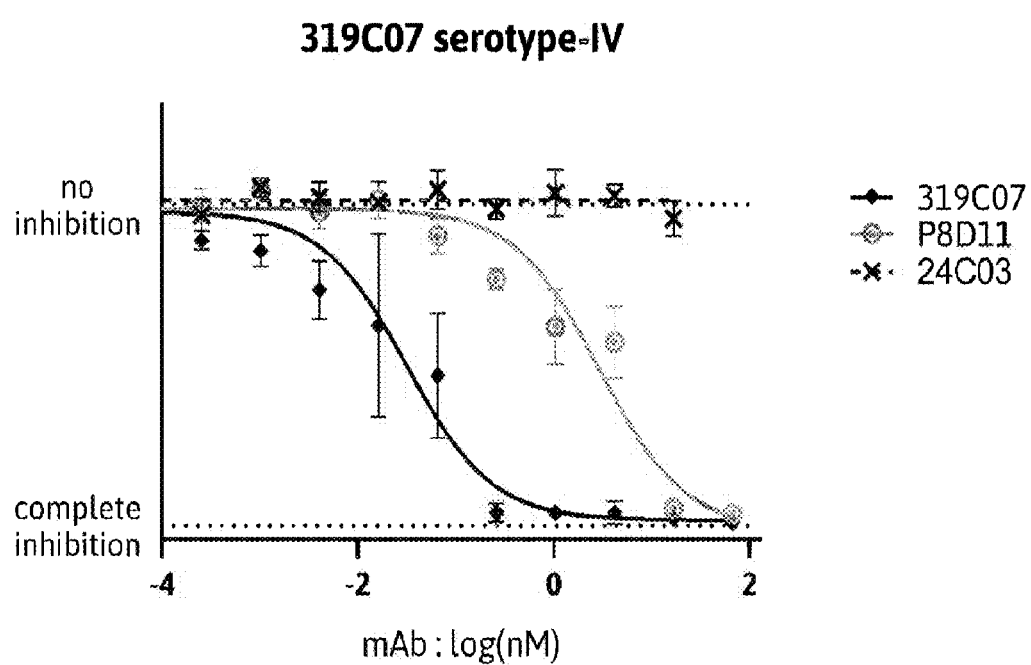

Figure 2 - continued
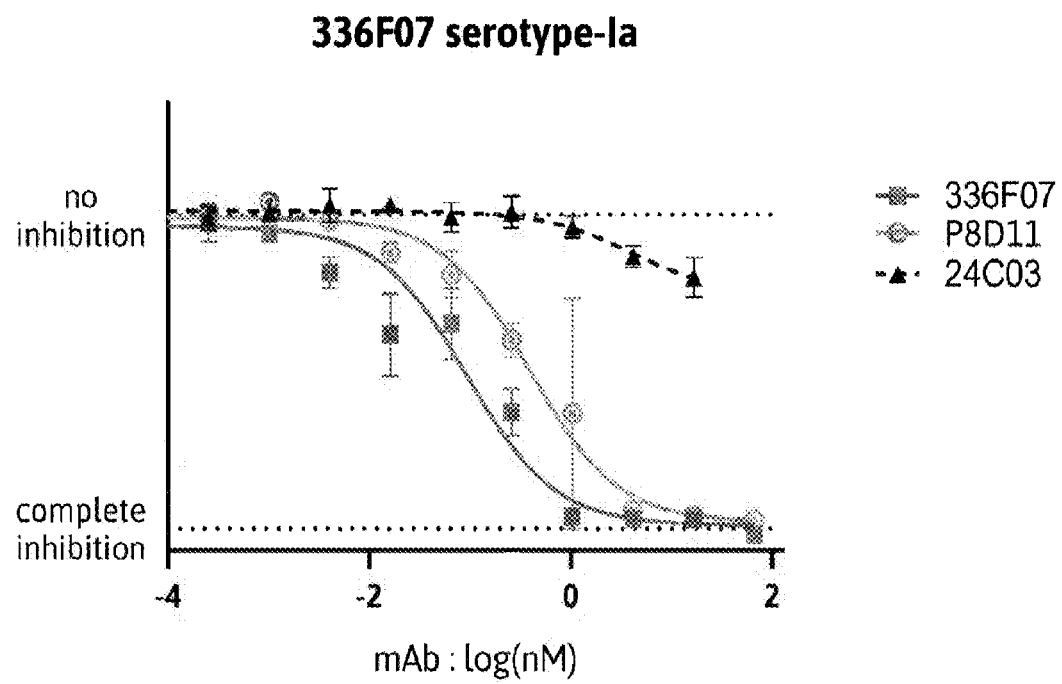
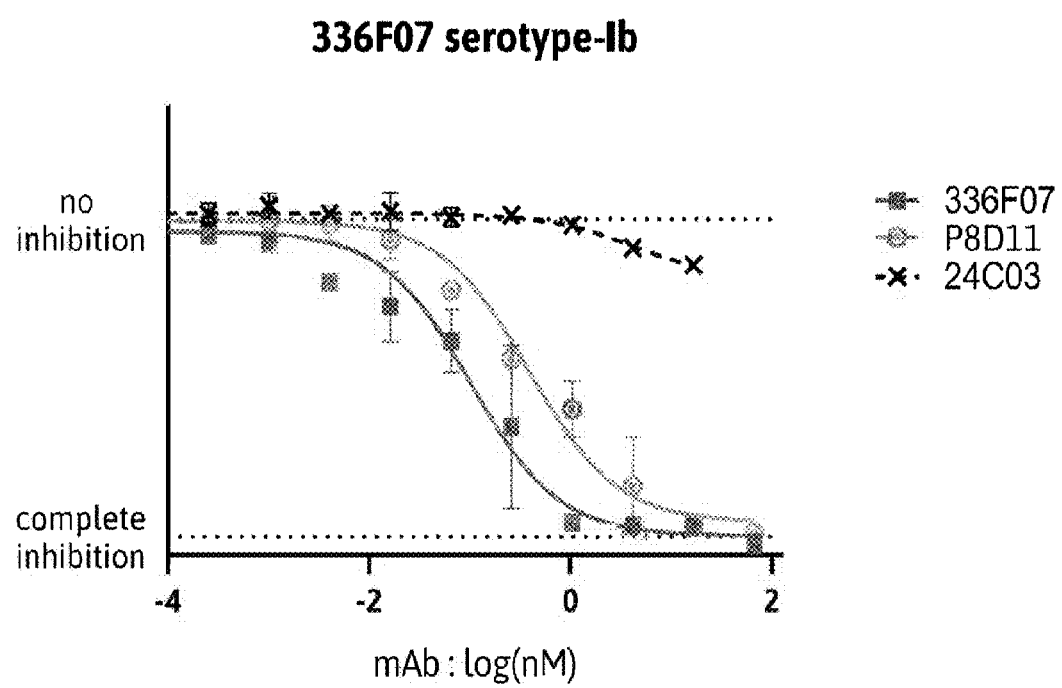

Figure 2 - continued
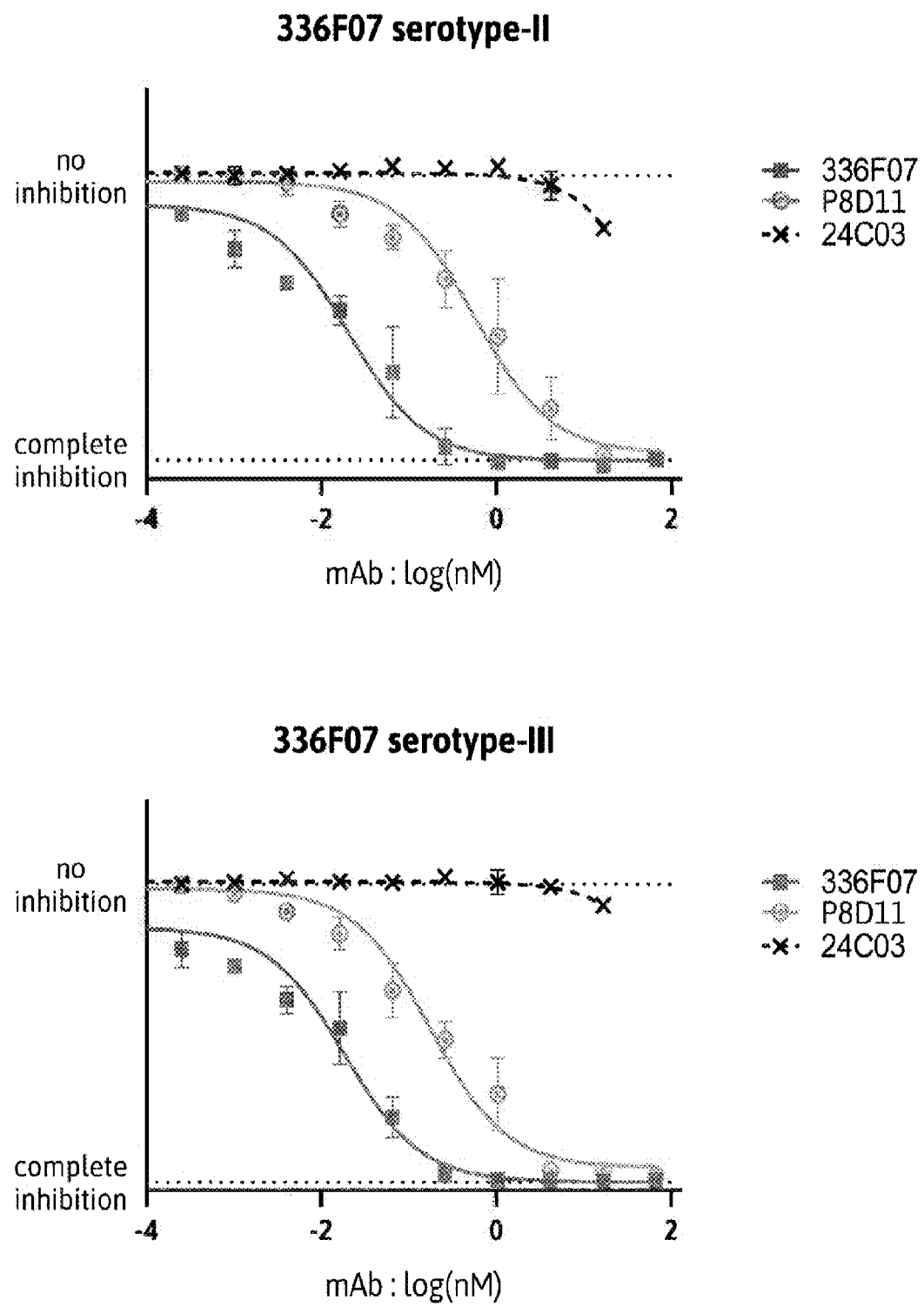

Figure 2 - continued
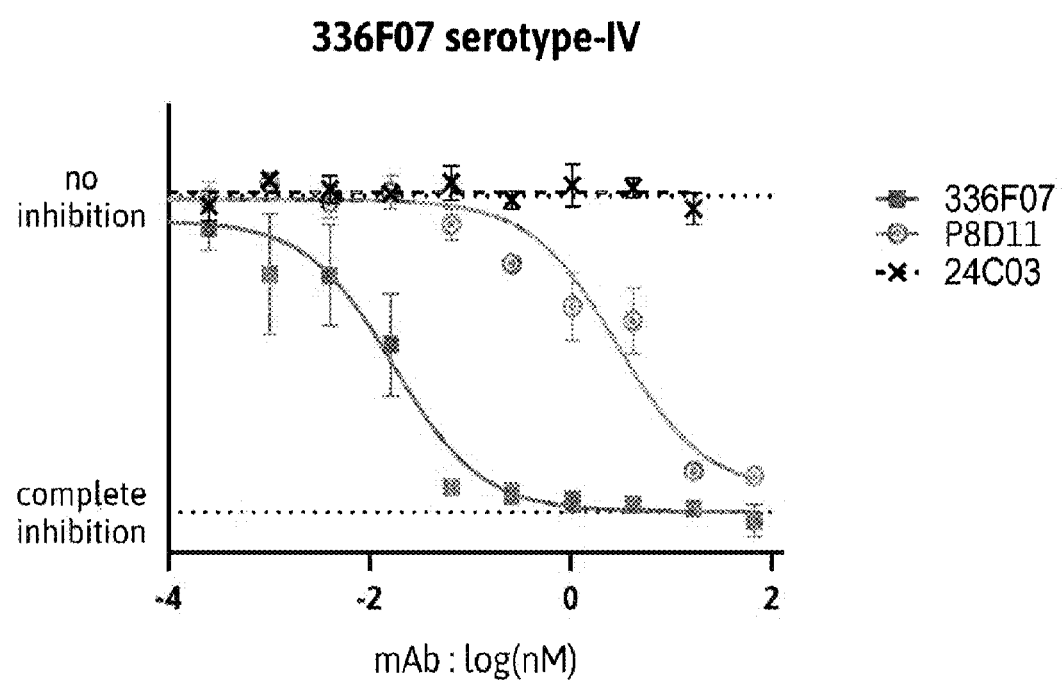

Figure 3
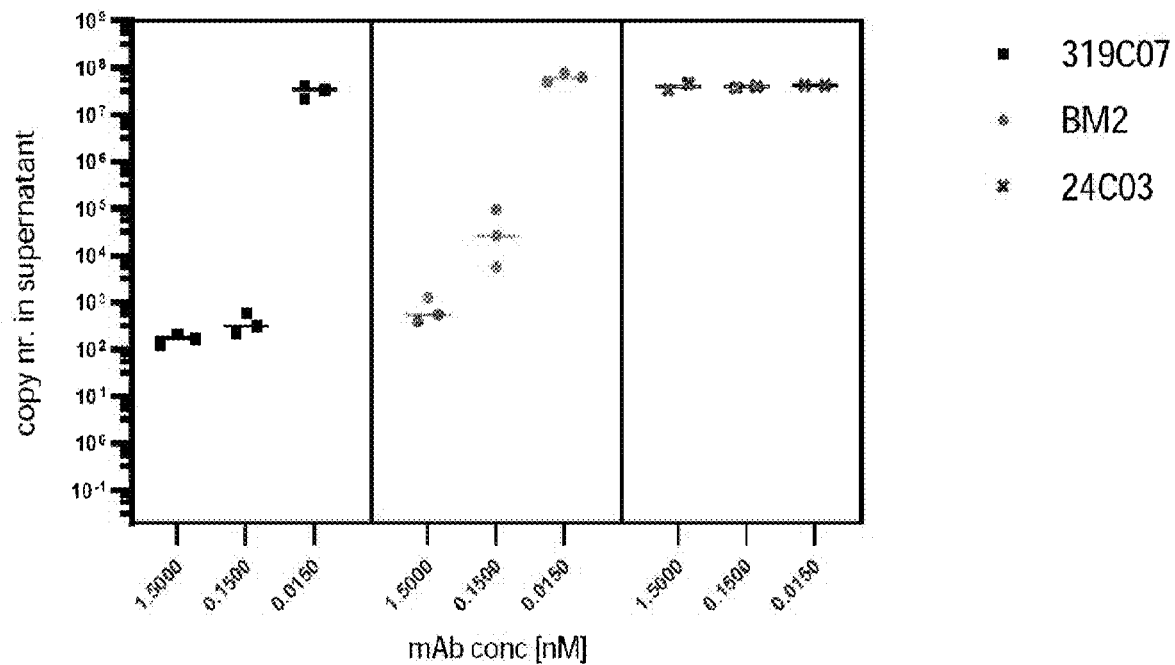
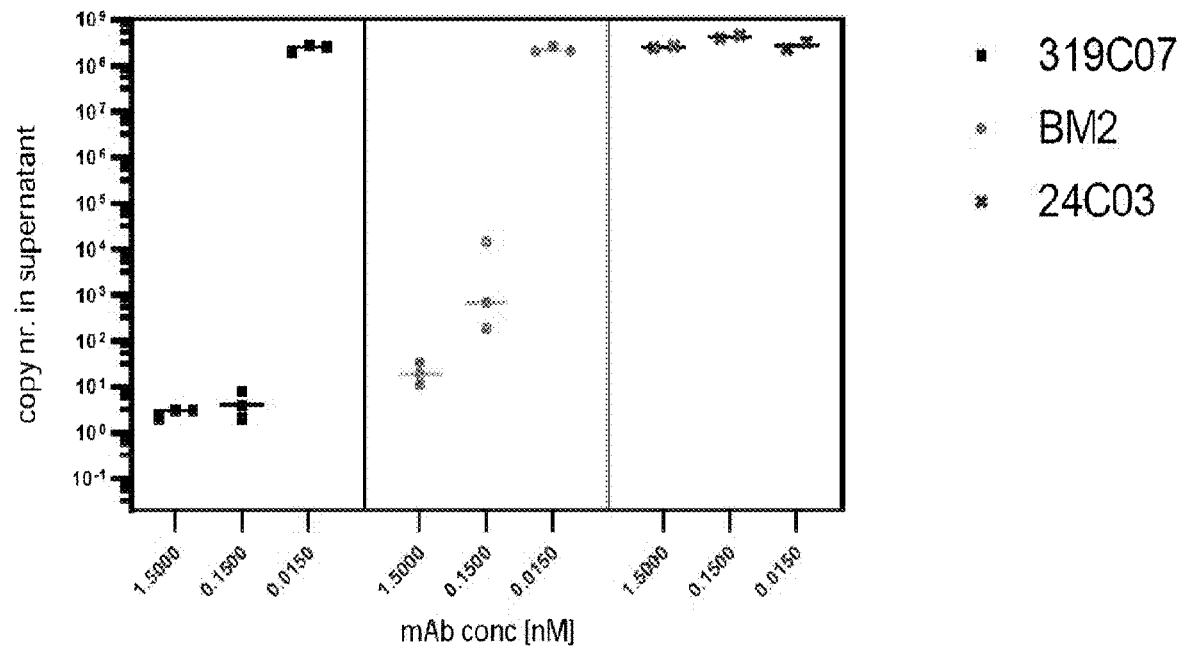

Figure 3 - continued
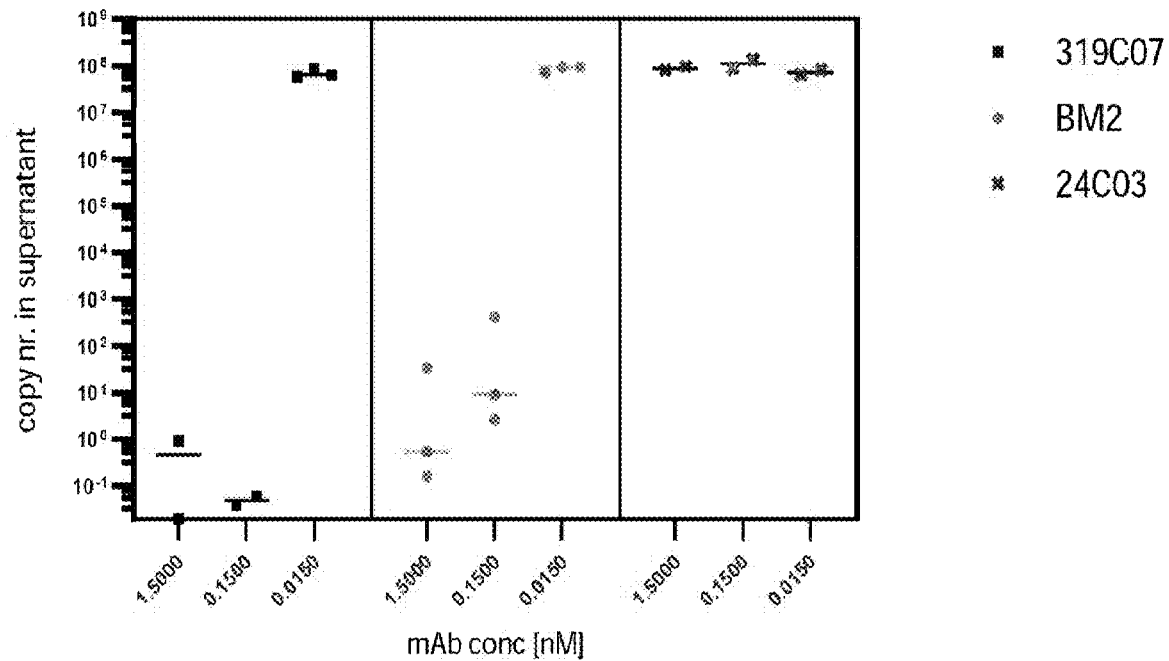
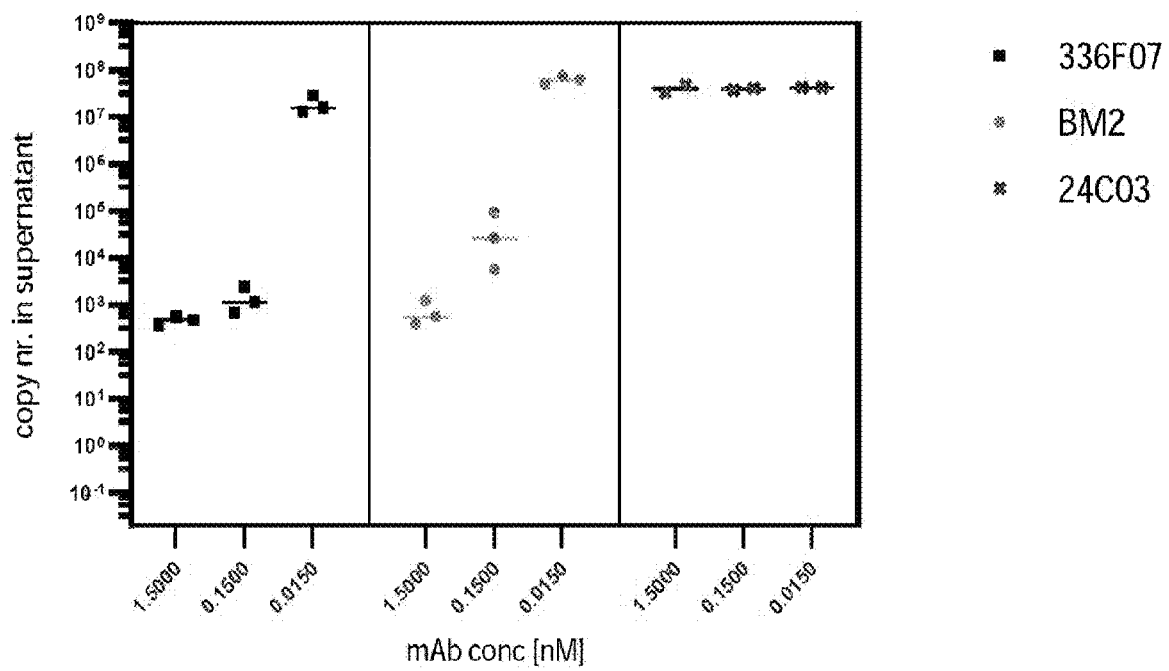

Figure 3 - continued
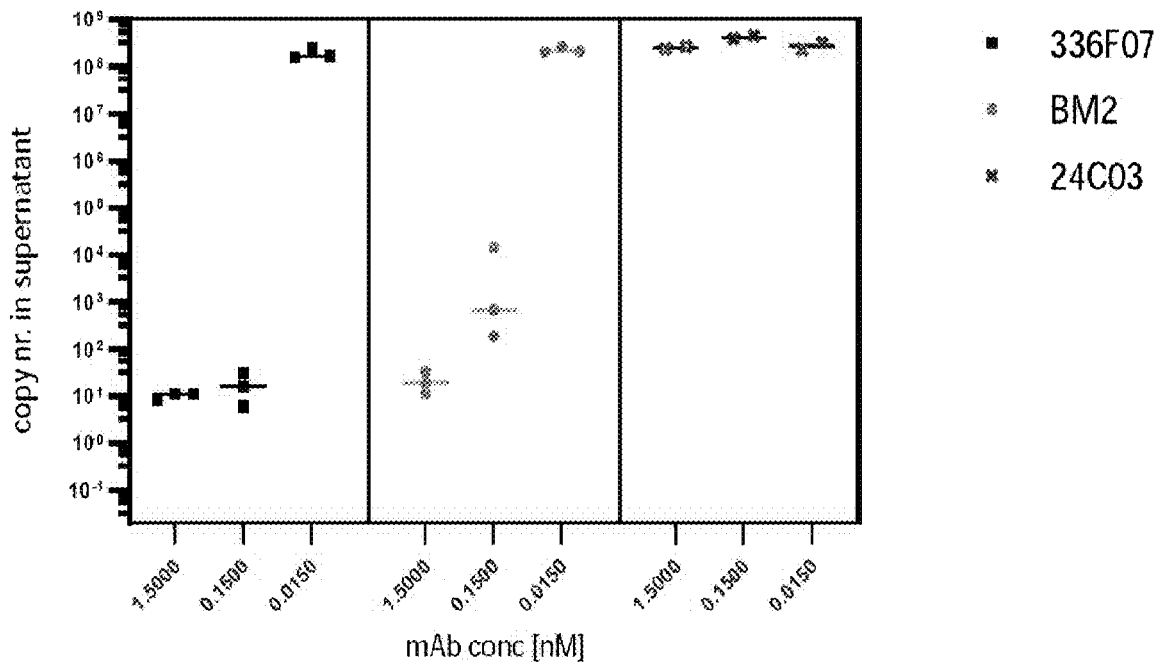
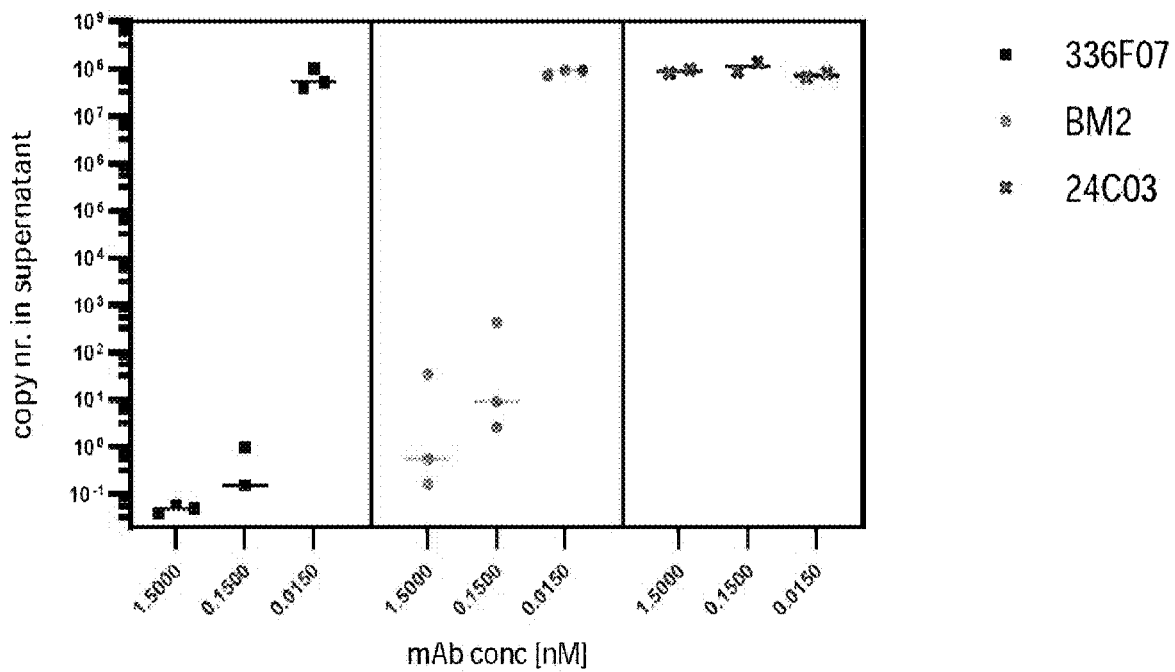

Figure 4

| mAb | AB Det. | VP1-I-His Denat. / native | VP1-II-His Denat. / native | VP1-III-His Denat. / native | VP1-IV-His Denat. / native |
|---|---|---|---|---|---|
| 319C07 | Anti-human HRP | | | | |
| P8D11 (pos. ctrl mAb) | | | | | |
| 24C3 (neg. ctrl mAb) | | | | | |
| PBS (no mAb) | | | | | |
| Ab53977 (pos. ctrl mAb) | Anti-rabbit HRP | | | | |
| PBS (no mAb) | | | | | |

| mAb | AB Det. | VP1-I-His Denat. / native | VP1-II-His Denat. / native | VP1-III-His Denat. / native | VP1-IV-His Denat. / native |
|---|---|---|---|---|---|
| 336F07 | Anti-human HRP | | | | |
| P8D11 (pos. ctrl mAb) | | | | | |
| 24C3 (neg. ctrl mAb) | | | | | |
| PBS (no mAb) | | | | | |
| Ab53977 (pos. ctrl mAb) | Anti-rabbit HRP | | | | |
| PBS (no mAb) | | | | | |

Figure 5
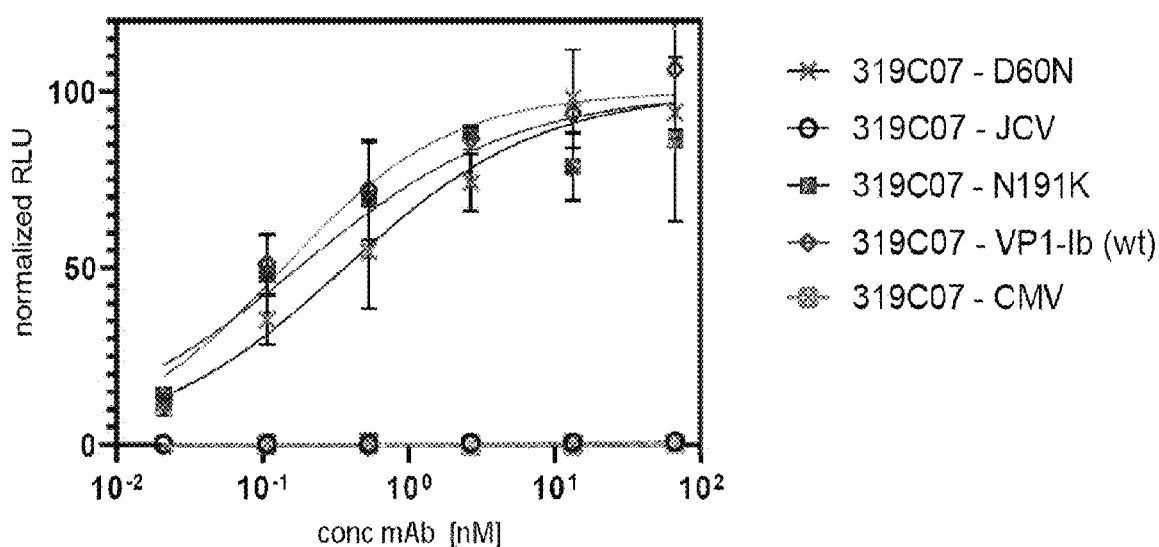
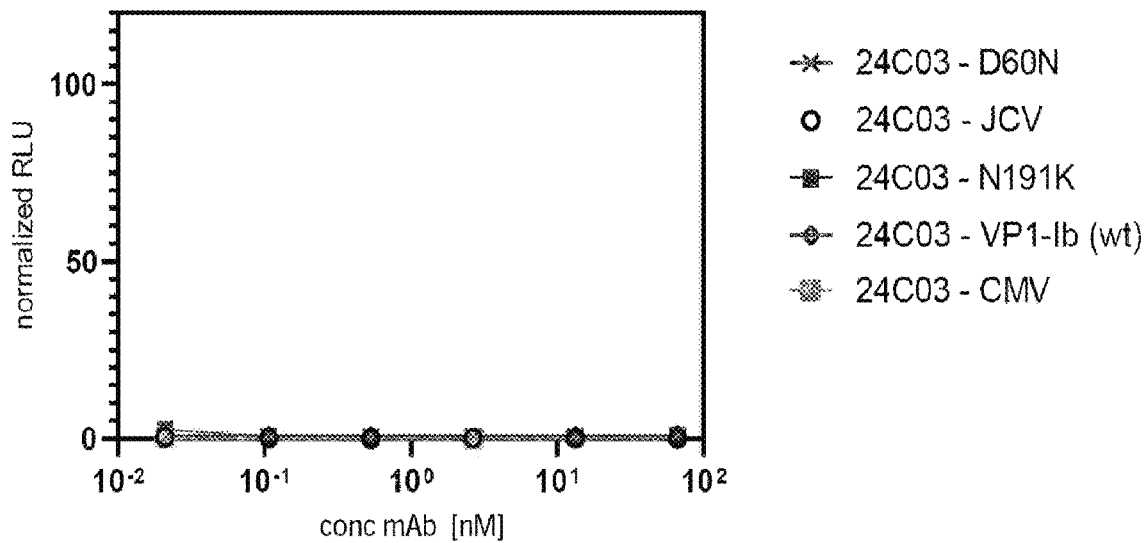

Figure 5 - continued
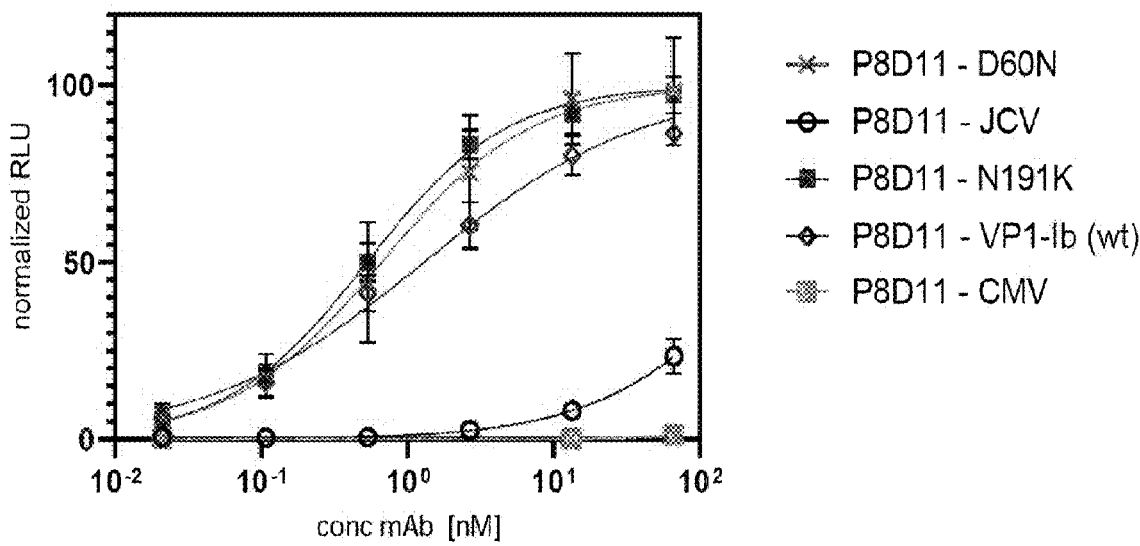
ELISA on VP1-I with mutations
|  | D60N | N62A | E73Q | S77A | E83A | E138D | K172A | Y173A | D175A | N191K | S275A | | JCV |
|---|---|---|---|---|---|---|---|---|---|---|---|---|---|
| 319C07 | + | red | + | + | + | + | + | + | red | + | red | | red |
| P8D11 | + | + | + | + | + | + | red | + | + | + | + | | red |
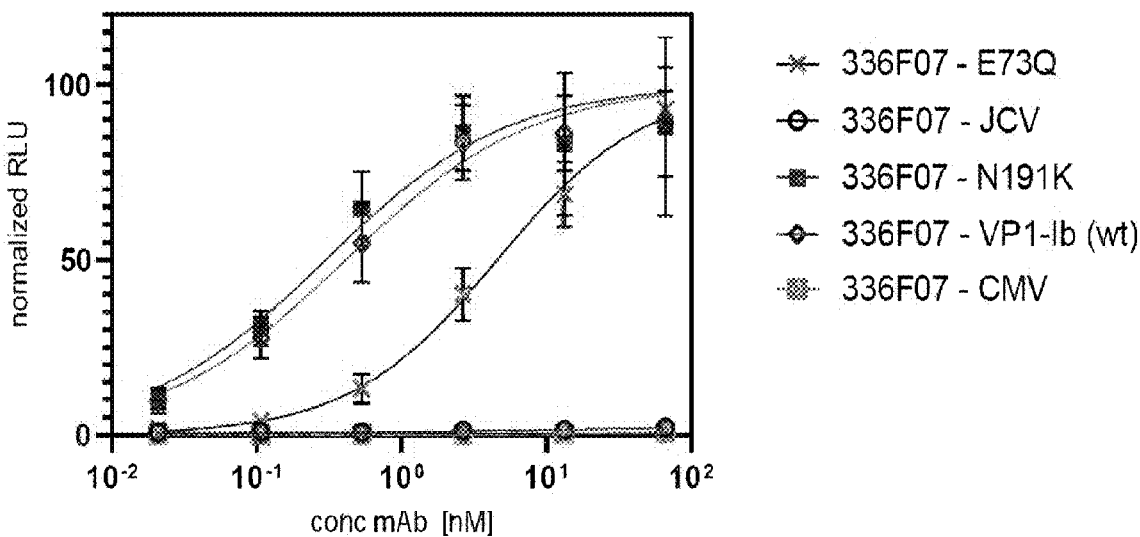
ELISA on VP1-I with mutations

Figure 5 - continued

ELISA on VP1-I with mutations

- 24C03 - E73Q
- 24C03 - JCV
- 24C03 - N191K
- 24C03 - VP1-Ib (wt)
- 24C03 - CMV

ELISA on VP1-I with mutations

- P8D11 - E73Q
- P8D11 - JCV
- P8D11 - N191K
- P8D11 - VP1-Ib (wt)
- P8D11 - CMV

| | D60N | N62A | E73Q | S77A | E83A | E138D | K172A | Y173A | D175A | N191K | S275A | | JCV |
|---|---|---|---|---|---|---|---|---|---|---|---|---|---|
| 336F07 | + | red | red | + | + | + | + | + | + | + | + | | red |
| P8D11 | + | + | + | + | + | + | red | + | + | + | + | | red |

Figure 6
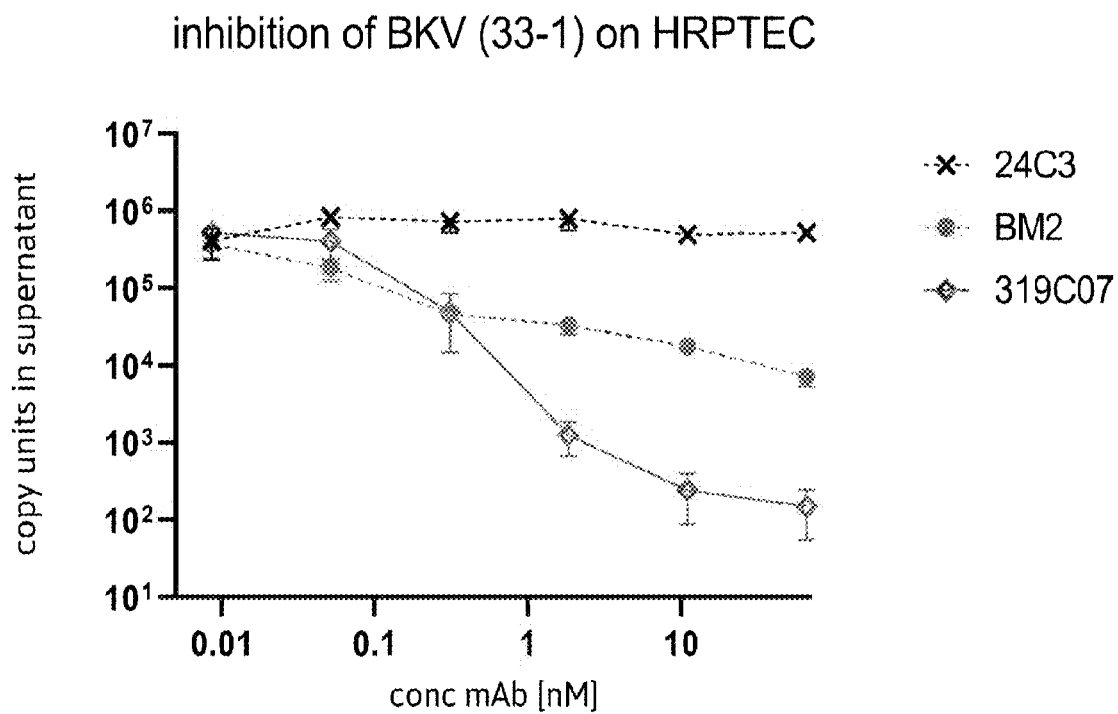
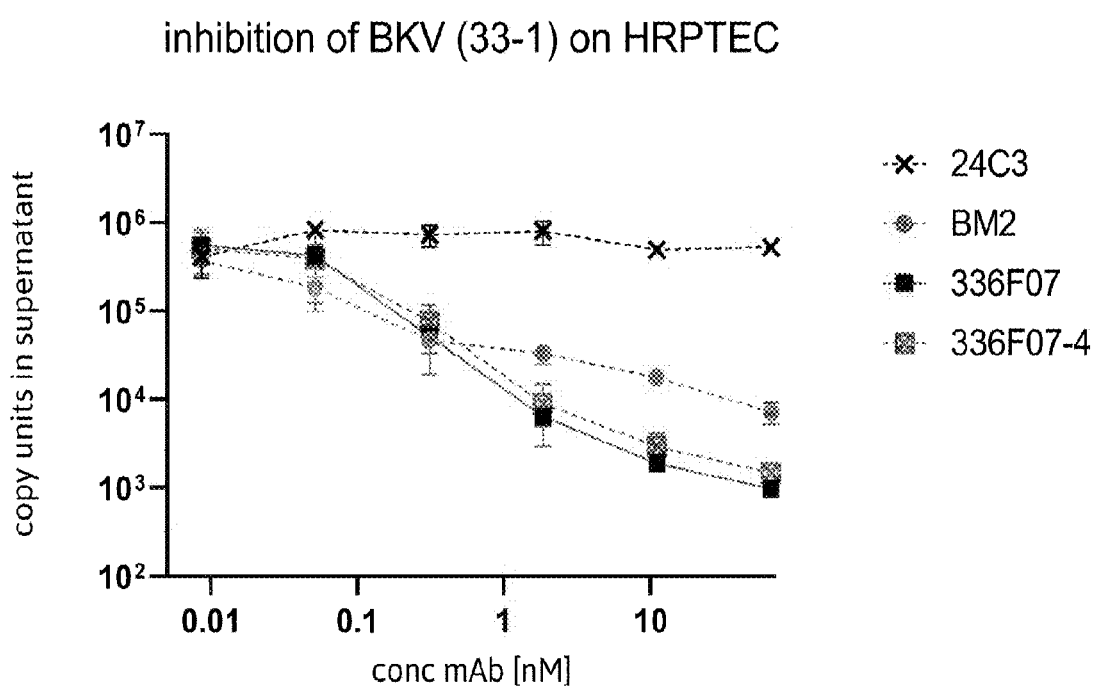

Figure 7 - continued
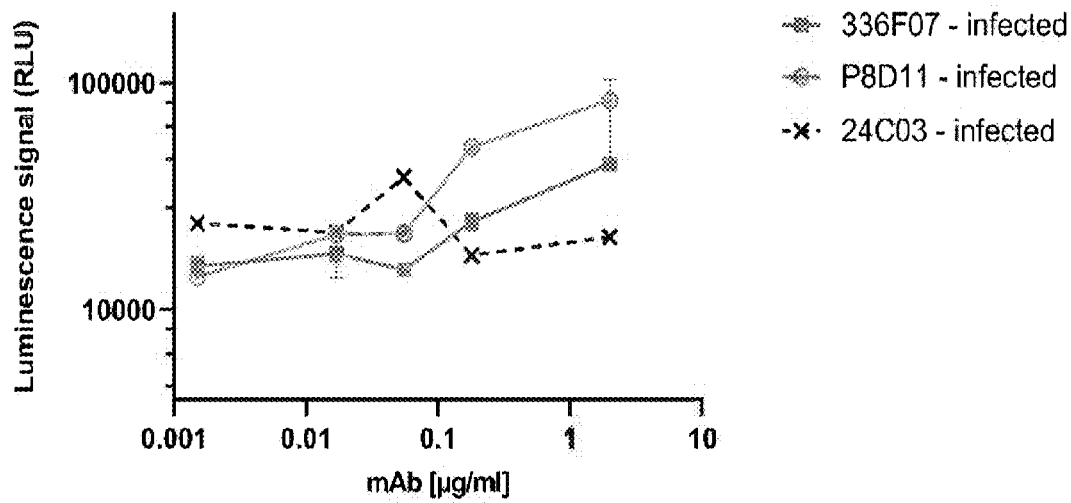
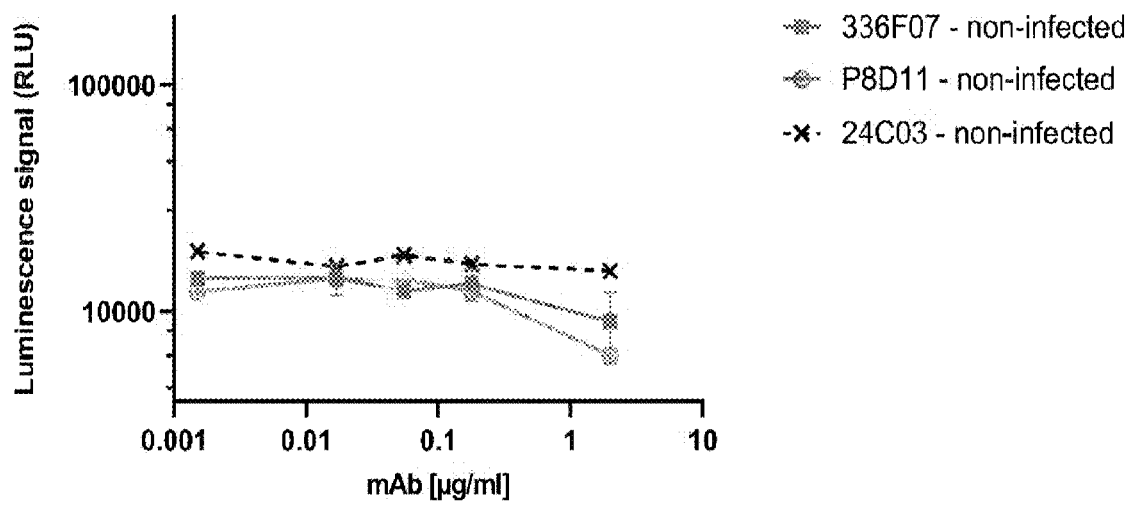

Figure 8
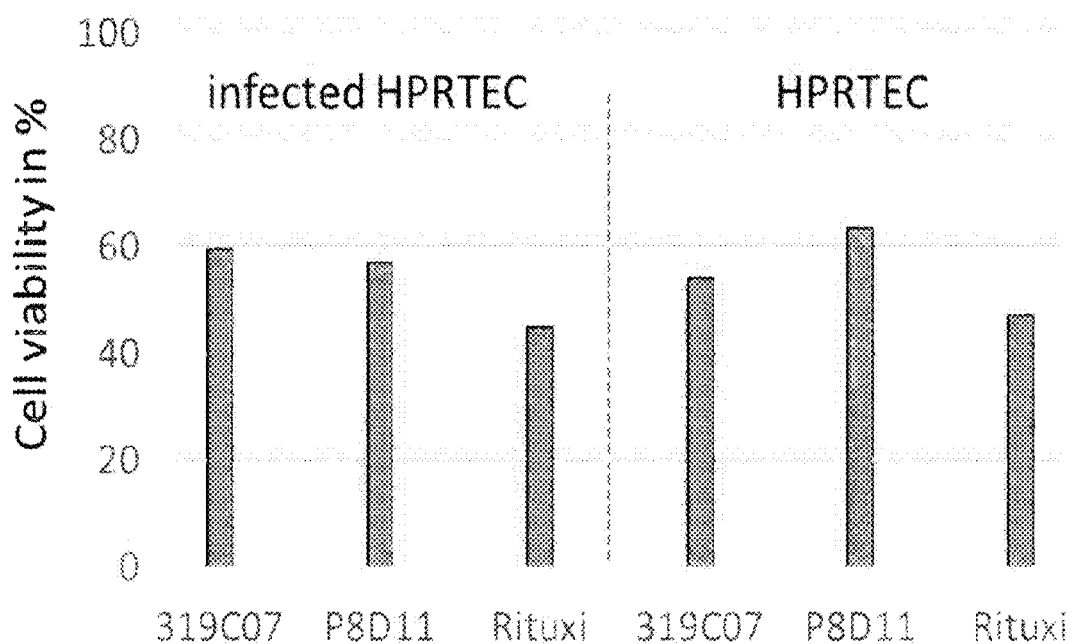
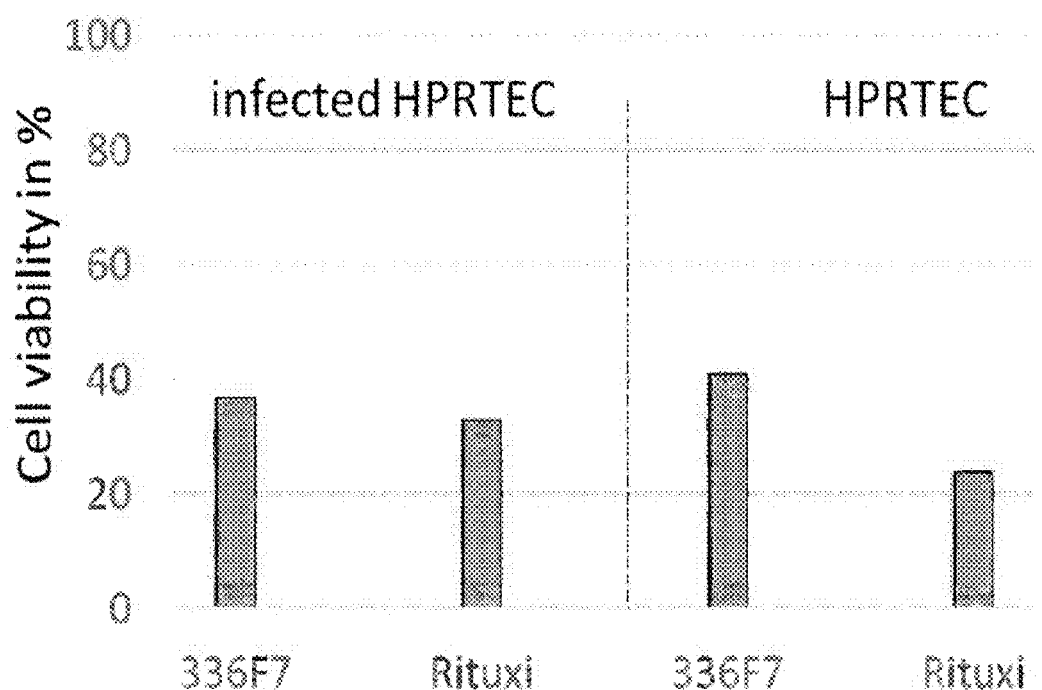

```
SEQUENCE LISTING

Sequence total quantity: 55
SEQ ID NO: 1            moltype = AA  length = 270
FEATURE                 Location/Qualifiers
source                  1..270
                        mol_type = protein
                        note = polyomavirus 1
                        organism = Homo sapiens
SEQUENCE: 1
GGVEVLEVKT GVDAITEVEC FLNPEMGDPD ENLRGFSLKL SAENDFSSDS PERKMLPCYS   60
TARIPLPNLN EDLTCGNLLM WEAVTVQTEV IGITSMLNLH AGSQKVHEHG GGKPIQGSNF  120
HFFAVGGDPL EMQGVLMNYR TKYPDGTITP KNPTAQSQVM NTDHKAYLDK NNAYPVECWV  180
PDPSRNENTR YFGTFTGGEN VPPVLHVTNT ATTVLLDEQG VGPLCKADSL YVSAADICGL  240
FTNSSGTQQW RGLARYFKIR LRKRSVKNPY                                   270

SEQ ID NO: 2            moltype = AA  length = 362
FEATURE                 Location/Qualifiers
source                  1..362
                        mol_type = protein
                        note = BK pseudovirus, VP1-Ia
                        organism = synthetic construct
SEQUENCE: 2
MAPTKRKGEC PGAAPKKPKE PVQVPKLLIK GGVEVLEVKT GVDAITEVEC FLNPEMGDPD   60
ENLRGFSLKL SAENDFSSDS PERKMLPCYS TARIPLPNLN EDLTCGNLLM WEAVTVQTEV  120
IGITSMLNLH AGSQKVHEHG GGKPIQGSNF HFFAVGGDPL EMQGVLMNYR TKYPDGTITP  180
KNPTAQSQVM NTDHKAYLDK NNAYPVECWV PDPSRNENTR YFGTFTGGEN VPPVLHVTNT  240
ATTVLLDEQG VGPLCKADSL YVSAADICGL FTNSSGTQQW RGLARYFKIR LRKRSVKNPY  300
PISFLLSDLI NRRTQRVDGQ PMYGMESQVE EVRVFDGTER LPGDPDMIRY IDKQGQLQTK  360
ML                                                                 362

SEQ ID NO: 3            moltype = AA  length = 362
FEATURE                 Location/Qualifiers
source                  1..362
                        mol_type = protein
```

```
                        note = BK pseudovirus, VP1-Ib
                        organism = synthetic construct
SEQUENCE: 3
MAPTKRKGEC  PGAAPKKPKE  PVQVPKLLIK  GGVEVLEVKT  GLDAITEVEC  FLNPEMGDPD   60
ENLRGFSLKL  SAENDFSSDS  PDRKMLPCYS  TARIPLPNLN  EDLTCGNLLM  WEAVTVQTEV  120
IGITSMLNLH  AGSQKVHEHG  GGKPIQGSNF  HFFAVGGDPL  EMQGVLMNYR  TKYPEGTITP  180
KNPTAQSQVM  NTDHKAYLDK  NNAYPVECWI  PDPSRNENTR  YFGTFTGGEN  VPPVLHVTNT  240
ATTVLLDEQG  VGPLCKADSL  YVSAADICGL  FTNSSGTQQW  RGLARYFKIR  LRKRSVKNPY  300
PISFLLSDLI  NRRTQRVDGQ  PMYGMESQVE  EVRVFDGTER  LPGDPDMIRY  IDKQGQLQTK  360
ML                                                                     362

SEQ ID NO: 4            moltype = AA  length = 270
FEATURE                 Location/Qualifiers
source                  1..270
                        mol_type = protein
                        note = polyomavirus 1
                        organism = Homo sapiens
SEQUENCE: 4
GGVEVLEVKT  GVDAITEVEC  FLNPEMGDPD  DNLRGYSLKL  TAENAFDSDS  PDKKMLPCYS   60
TARIPLPNLN  EDLTCGNLLM  WEAVTVKTEV  IGITSMLNLH  AGSQKVHENG  GGKPVQGSNF  120
HFFAVGGDPL  EMQGVLMNYR  TKYPQGTITP  KNPTAQSQVM  NTDHKAYLDK  NNAYPVECWI  180
PDPSRNENTR  YFGTYTGGEN  VPPVLHVTNT  ATTVLLDEQG  VGPLCKADSL  YVSAADICGL  240
FTNSSGTQQW  RGLARYFKIR  LRKRSVKNPY                                     270

SEQ ID NO: 5            moltype = AA  length = 362
FEATURE                 Location/Qualifiers
source                  1..362
                        mol_type = protein
                        note = BK pseudovirus, VP1-II
                        organism = synthetic construct
SEQUENCE: 5
MAPTKRKGEC  PGAAPKKPKE  PVQVPKLLIK  GGVEVLEVKT  GVDAITEVEC  FLNPEMGDPD   60
DNLRGYSLKL  TAENAFDSDS  PDKKMLPCYS  TARIPLPNLN  EDLTCGNLLM  WEAVTVKTEV  120
IGITSMLNLH  AGSQKVHENG  GGKPVQGSNF  HFFAVGGDPL  EMQGVLMNYR  TKYPQGTITP  180
KNPTAQSQVM  NTDHKAYLDK  NNAYPVECWI  PDPSRNENTR  YFGTYTGGEN  VPPVLHVTNT  240
ATTVLLDEQG  VGPLCKADSL  YVSAADICGL  FTNSSGTQQW  RGLARYFKIR  LRKRSVKNPY  300
PISFLLSDLI  NRRTQRVDGQ  PMYGMESQVE  EVRVFDGTEQ  LPGDPDMIRY  IDRQGQLQTK  360
MV                                                                     362

SEQ ID NO: 6            moltype = AA  length = 362
FEATURE                 Location/Qualifiers
source                  1..362
                        mol_type = protein
                        note = polyomavirus 1
                        organism = Homo sapiens
SEQUENCE: 6
MAPTKRKGEC  PGAAPKKPKE  PVQVPKLLIK  GGVEVLEVKT  GVDAITEVEC  FLNPEMGDPD   60
DNLRGYSQHL  SAENAFESDS  PDRKMLPCYS  TARIPLPNLN  EDLTCGNLLM  WEAVTVKTEV  120
IGITSMLNLH  AGSQKVHENG  GGKPVQGSNF  HFFAVGGDPL  EMQGVLMNYR  TKYPQGTITP  180
KNPTAQSQVM  NTDHKAYLDK  NNAYPVECWI  PDPSRNENTR  YFGTYTGGEN  VPPVLHVTNT  240
ATTVLLDEQG  VGPLCKADSL  YVSAADICGL  FTNSSGTQQW  RGLARYFKIR  LRKRSVKNPY  300
PISFLLSDLI  NRRTQKVDGQ  PMYGMESQVE  EVRVFDGTEQ  LPGDPDMIRY  IDRQGQLQTK  360
MV                                                                     362

SEQ ID NO: 7            moltype = AA  length = 362
FEATURE                 Location/Qualifiers
source                  1..362
                        mol_type = protein
                        note = BK pseudovirus, VP1-III
                        organism = synthetic construct
SEQUENCE: 7
MAPTKRKGEC  PGAAPKKPKE  PVQVPKLLIK  GGVEVLEVKT  GVDAITEVEC  FLNPEMGDPD   60
DNLRGYSQHL  SAENAFESDS  PDRKMLPCYS  TARIPLPNLN  EDLTCGNLLM  WEAVTVKTEV  120
IGITSMLNLH  AGSQKVHENG  GGKPVQGSNF  HFFAVGGDPL  EMQGVLMNYR  TKYPQGTITP  180
KNPTAQSQVM  NTDHKAYLDK  NNAYPVECWI  PDPSRNENTR  YFGTYTGGEN  VPPVLHVTNT  240
ATTVLLDEQG  VGPLCKADSL  YVSAADICGL  FTNSSGTQQW  RGLARYFKIR  LRKRSVKNPY  300
PISFLLSDLI  NRRTQRVDGQ  PMYGMESQVE  EVRVFDGTEQ  LPGDPDMIRY  IDRQGQLQTK  360
MV                                                                     362

SEQ ID NO: 8            moltype = AA  length = 270
FEATURE                 Location/Qualifiers
source                  1..270
                        mol_type = protein
                        note = polyomavirus 1
                        organism = Homo sapiens
SEQUENCE: 8
GGVEVLEVKT  GVDAITEVEC  FLNPEMGDPD  NDLRGYSLRL  TAETAFDSDS  PDRKMLPCYS   60
TARIPLPNLN  EDLTCGNLLM  WEAVTVKTEV  IGITSMLNLH  AGSQKVHENG  GGKPIQGSNF  120
HFFAVGGDPL  EMQGVLMNYR  TKYPEGTVTP  KNPTAQSQVM  NTDHKAYLDK  NNAYPVECWI  180
```

```
PDPSRNENTR YFGTYTGGEN VPPVLHVTNT ATTVLLDEQG VGPLCKADSL YVSAADICGL   240
FTNSSGTQQW RGLPRYFKIR MRKRSVKNPY                                   270

SEQ ID NO: 9             moltype = AA  length = 362
FEATURE                  Location/Qualifiers
source                   1..362
                         mol_type = protein
                         note = BK pseudovirus, VP1-IVc
                         organism = synthetic construct
SEQUENCE: 9
MAPTKRKGEC PGAAPKKPKE PVQVPKLLIK GGVEVLEVKT GVDAITEVEC FLNPEMGDPD    60
NDLRGYSLRL TAETAFDSDS PDRKMLPCYS TARIPLPNLN EDLTCGNLLM WEAVTVKTEV   120
IGITSMLNLH AGSQKVHENG GGKPIQGSNF HFFAVGGDPL EMQGVLMNYR TKYPEGTVTP   180
KNPTAQSQVM NTDHKAYLDK NNAYPVECWI PDPSKNENTR YFGTYTGGEN VPPVLHVTNT   240
ATTVLLDEQG VGPLCKADSL YVSAADICGL FTNSSGTQQW RGLPRYFKIR LRKRSVKNPY   300
PISFLLSDLI NRRTQRVDGQ PMYGMESQVE EVRVFDGTEQ LPGDPDMIRY IDRQGQLQTK   360
MV                                                                 362

SEQ ID NO: 10            moltype = AA  length = 270
FEATURE                  Location/Qualifiers
source                   1..270
                         mol_type = protein
                         note = JC polyomavirus
                         organism = Homo sapiens
SEQUENCE: 10
GGVEVLEVKT GVDSITEVEC FLTPEMGDPD EHLRGFSKSI SISDTFESDS PNRDMLPCYS    60
VARIPLPNLN EDLTCGNILM WEAVTLKTEV IGVTSLMNVH SNGQATHDNG AGKPVQGTSF   120
HFFSVGGEAL ELQGVLFNYR TKYPDGTIFP KNATVQSQVM NTEHKAYLDK NKAYPVECWV   180
PDPTRNENTR YFGTLTGGEN VPPVLHITNT ATTVLLDEFG VGPLCKGDNL YLSAVDVCGM   240
FTNRSGSQQW RGLSRYFKVQ LRKRRVKNPY                                   270

SEQ ID NO: 11            moltype = AA  length = 5
FEATURE                  Location/Qualifiers
source                   1..5
                         mol_type = protein
                         note = heavy chain complementarity determining region 1
                         organism = synthetic construct
SEQUENCE: 11
NYWMT                                                                5

SEQ ID NO: 12            moltype = AA  length = 17
FEATURE                  Location/Qualifiers
source                   1..17
                         mol_type = protein
                         note = heavy chain complementarity determining region 2
                         organism = synthetic construct
SEQUENCE: 12
NIKKDGSEKY YVDSVRG                                                  17

SEQ ID NO: 13            moltype = AA  length = 11
FEATURE                  Location/Qualifiers
source                   1..11
                         mol_type = protein
                         note = heavy chain complementarity determining region 3
                         organism = synthetic construct
SEQUENCE: 13
VRSGRYFALD D                                                        11

SEQ ID NO: 14            moltype = AA  length = 11
FEATURE                  Location/Qualifiers
source                   1..11
                         mol_type = protein
                         note = light chain complementarity determining region 1
                         organism = synthetic construct
SEQUENCE: 14
GGDNIGSRPV H                                                        11

SEQ ID NO: 15            moltype = AA  length = 7
FEATURE                  Location/Qualifiers
source                   1..7
                         mol_type = protein
                         note = light chain complementarity determining region 2
                         organism = synthetic construct
SEQUENCE: 15
DDSNRPS                                                              7

SEQ ID NO: 16            moltype = AA  length = 10
FEATURE                  Location/Qualifiers
source                   1..10
```

```
                              mol_type = protein
                              note = light chain complementarity determining region 3
                              organism = synthetic construct
SEQUENCE: 16
QVWSSSTDHP                                                                     10

SEQ ID NO: 17             moltype = AA   length = 120
FEATURE                   Location/Qualifiers
source                    1..120
                          mol_type = protein
                          note = heavy chain variable region
                          organism = synthetic construct
SEQUENCE: 17
QVQLVESGGT LVQPGGSLRL SCAASGFTFN NYWMTWVRQA PGKGLEWVAN IKKDGSEKYY        60
VDSVRGRFTI SRDNAKNSLF LQMNSLRPED TAVYFCATVR SGRYFALDDW GQGTLVTVSS       120

SEQ ID NO: 18             moltype = AA   length = 107
FEATURE                   Location/Qualifiers
source                    1..107
                          mol_type = protein
                          note = light chain variable region
                          organism = synthetic construct
SEQUENCE: 18
QSVLTQPPSV SVAPGKTARI TCGGDNIGSR PVHWYQQKPG QAPILVVYDD SNRPSGIPER        60
FSGSNSGNTA TLTISRVEAG DEADYYCQVW SSSTDHPFGG GTKVTVL                     107

SEQ ID NO: 19             moltype = AA   length = 450
FEATURE                   Location/Qualifiers
source                    1..450
                          mol_type = protein
                          note = full length heavy chain
                          organism = synthetic construct
SEQUENCE: 19
QVQLVESGGT LVQPGGSLRL SCAASGFTFN NYWMTWVRQA PGKGLEWVAN IKKDGSEKYY        60
VDSVRGRFTI SRDNAKNSLF LQMNSLRPED TAVYFCATVR SGRYFALDDW GQGTLVTVSS       120
ASTKGPSVFP LAPSSKSTSG GTAALGCLVK DYFPEPVTVS WNSGALTSGV HTFPAVLQSS       180
GLYSLSSVVT VPSSSLGTQT YICNVNHKPS NTKVDKKVEP KSCDKTHTCP PCPAPELLGG       240
PSVFLFPPKP KDTLMISRTP EVTCVVVDVS HEDPEVKFNW YVDGVEVHNA KTKPREEQYN       300
STYRVVSVLT VLHQDWLNGK EYKCKVSNKA LPAPIEKTIS KAKGQPREPQ VYTLPPSREE       360
MTKNQVSLTC LVKGFYPSDI AVEWESNGQP ENNYKTTPPV LDSDGSFFLY SKLTVDKSRW       420
QQGNVFSCSV MHEALHNHYT QKSLSLSPGK                                       450

SEQ ID NO: 20             moltype = AA   length = 213
FEATURE                   Location/Qualifiers
source                    1..213
                          mol_type = protein
                          note = full length light chain
                          organism = synthetic construct
SEQUENCE: 20
QSVLTQPPSV SVAPGKTARI TCGGDNIGSR PVHWYQQKPG QAPILVVYDD SNRPSGIPER        60
FSGSNSGNTA TLTISRVEAG DEADYYCQVW SSSTDHPFGG GTKVTVLGQP KAAPSVTLFP       120
PSSEELQANK ATLVCLISDF YPGAVTVAWK ADSSPVKAGV ETTTPSKQSN NKYAASSYLS       180
LTPEQWKSHR SYSCQVTHEG STVEKTVAPT ECS                                   213

SEQ ID NO: 21             moltype = AA   length = 5
FEATURE                   Location/Qualifiers
source                    1..5
                          mol_type = protein
                          note = heavy chain complementarity determining region 1
                          organism = synthetic construct
SEQUENCE: 21
AYYWT                                                                           5

SEQ ID NO: 22             moltype = AA   length = 16
FEATURE                   Location/Qualifiers
source                    1..16
                          mol_type = protein
                          note = heavy chain complementarity determining region 2
                          organism = synthetic construct
SEQUENCE: 22
EINHRGYTNY NPSLRG                                                              16

SEQ ID NO: 23             moltype = AA   length = 13
FEATURE                   Location/Qualifiers
source                    1..13
                          mol_type = protein
                          note = heavy chain complementarity determining region 3
                          organism = synthetic construct
SEQUENCE: 23
```

```
LRSTSGWHDY FDY                                                                   13

SEQ ID NO: 24             moltype = AA  length = 12
FEATURE                   Location/Qualifiers
source                    1..12
                          mol_type = protein
                          note = light chain complementarity determining region 1
                          organism = synthetic construct
SEQUENCE: 24
RASQSVSSSY LA                                                                    12

SEQ ID NO: 25             moltype = AA  length = 7
FEATURE                   Location/Qualifiers
source                    1..7
                          mol_type = protein
                          note = light chain complementarity determining region 2
                          organism = synthetic construct
SEQUENCE: 25
GASSRAT                                                                          7

SEQ ID NO: 26             moltype = AA  length = 9
FEATURE                   Location/Qualifiers
source                    1..9
                          mol_type = protein
                          note = light chain complementarity determining region 3
                          organism = synthetic construct
SEQUENCE: 26
LQYGSSPLT                                                                        9

SEQ ID NO: 27             moltype = AA  length = 121
FEATURE                   Location/Qualifiers
source                    1..121
                          mol_type = protein
                          note = heavy chain variable region
                          organism = synthetic construct
SEQUENCE: 27
QVQLQQWGAG LLKPSETLSL TCAVYRGSFS AYYWTWFRQP PGKGLEWIGE INHRGYTNYN                 60
PSLRGRVSIS VDTSKKQFSL KLRSVNAADT AVYYCATLRS TSGWHDYFDY WGQGTLVTVS                120
S                                                                               121

SEQ ID NO: 28             moltype = AA  length = 108
FEATURE                   Location/Qualifiers
source                    1..108
                          mol_type = protein
                          note = light chain variable region
                          organism = synthetic construct
SEQUENCE: 28
EIVLTQSPGT LSLSPGERAT LSCRASQSVS SSYLAWYQQT PGQAPRLLIY GASSRATGIP                 60
DRFSGSGSGT DFTLTISRLE PEDFVVYFCL QYGSSPLTFG PGTKVDIK                            108

SEQ ID NO: 29             moltype = AA  length = 451
FEATURE                   Location/Qualifiers
source                    1..451
                          mol_type = protein
                          note = full length heavy chain
                          organism = synthetic construct
SEQUENCE: 29
QVQLQQWGAG LLKPSETLSL TCAVYRGSFS AYYWTWFRQP PGKGLEWIGE INHRGYTNYN                 60
PSLRGRVSIS VDTSKKQFSL KLRSVNAADT AVYYCATLRS TSGWHDYFDY WGQGTLVTVS                120
SASTKGPSVF PLAPSSKSTS GGTAALGCLV KDYFPEPVTV SWNSGALTSG VHTFPAVLQS                180
SGLYSLSSVV TVPSSSLGTQ TYICNVNHKP SNTKVDKKVE PKSCDKTHTC PPCPAPELLG                240
GPSVFLFPPK PKDTLMISRT PEVTCVVVDV SHEDPEVKFN WYVDGVEVHN AKTKPREEQY                300
NSTYRVVSVL TVLHQDWLNG KEYKCKVSNK ALPAPIEKTI SKAKGQPREP QVYTLPPSRE                360
EMTKNQVSLT CLVKGFYPSD IAVEWESNGQ PENNYKTTPP VLDSDGSFFL YSKLTVDKSR                420
WQQGNVFSCS VMHEALHNHY TQKSLSLSPG K                                              451

SEQ ID NO: 30             moltype = AA  length = 215
FEATURE                   Location/Qualifiers
source                    1..215
                          mol_type = protein
                          note = full length light chain
                          organism = synthetic construct
SEQUENCE: 30
EIVLTQSPGT LSLSPGERAT LSCRASQSVS SSYLAWYQQT PGQAPRLLIY GASSRATGIP                 60
DRFSGSGSGT DFTLTISRLE PEDFVVYFCL QYGSSPLTFG PGTKVDIKRT VAAPSVFIFP                120
PSDEQLKSGT ASVVCLLNNF YPREAKVQWK VDNALQSGNS QESVTEQDSK DSTYSLSSTL                180
TLSKADYEKH KVYACEVTHQ GLSSPVTKSF NRGEC                                          215

SEQ ID NO: 31             moltype = AA  length = 108
```

```
FEATURE                 Location/Qualifiers
source                  1..108
                        mol_type = protein
                        note = light chain variable region
                        organism = synthetic construct
SEQUENCE: 31
EIVLTQSPGT LSLSPGERAT LSCRASQSVS SSYLAWYQQK PGQAPRLLIY GASSRATGIP    60
DRFSGSGSGT DFTLTISRLE PEDFAVYFCL QYGSSPLTFG PGTKVDIK                108

SEQ ID NO: 32           moltype = AA   length = 451
FEATURE                 Location/Qualifiers
source                  1..451
                        mol_type = protein
                        note = full length heavy chain
                        organism = synthetic construct
SEQUENCE: 32
QVQLQQWGAG LLKPSETLSL TCAVYRGSFS AYYWTWFRQP PGKGLEWIGE INHRGYTNYN    60
PSLRGRVSIS VDTSKKQFSL KLRSVNAADT AVYYCATLRS TSGWHDYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 33           moltype = AA   length = 215
FEATURE                 Location/Qualifiers
source                  1..215
                        mol_type = protein
                        note = full length light chain
                        organism = synthetic construct
SEQUENCE: 33
EIVLTQSPGT LSLSPGERAT LSCRASQSVS SSYLAWYQQK PGQAPRLLIY GASSRATGIP    60
DRFSGSGSGT DFTLTISRLE PEDFAVYFCL QYGSSPLTFG PGTKVDIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 34           moltype = AA   length = 5
FEATURE                 Location/Qualifiers
source                  1..5
                        mol_type = protein
                        note = heavy chain complementarity determining region 1
                        organism = synthetic construct
SEQUENCE: 34
LYAMN                                                                5

SEQ ID NO: 35           moltype = AA   length = 17
FEATURE                 Location/Qualifiers
source                  1..17
                        mol_type = protein
                        note = heavy chain complementarity determining region 2
                        organism = synthetic construct
SEQUENCE: 35
LISGSGTATY YADSVTG                                                  17

SEQ ID NO: 36           moltype = AA   length = 15
FEATURE                 Location/Qualifiers
source                  1..15
                        mol_type = protein
                        note = heavy chain complementarity determining region 3
                        organism = synthetic construct
SEQUENCE: 36
TYPTWGGVVI GAIDV                                                    15

SEQ ID NO: 37           moltype = AA   length = 11
FEATURE                 Location/Qualifiers
source                  1..11
                        mol_type = protein
                        note = light chain complementarity determining region 1
                        organism = synthetic construct
SEQUENCE: 37
RASQSIQRWL A                                                        11

SEQ ID NO: 38           moltype = AA   length = 7
FEATURE                 Location/Qualifiers
source                  1..7
                        mol_type = protein
                        note = light chain complementarity determining region 2
                        organism = synthetic construct
```

```
SEQUENCE: 38
DASTLES                                                                              7

SEQ ID NO: 39            moltype = AA   length = 9
FEATURE                  Location/Qualifiers
source                   1..9
                         mol_type = protein
                         note = light chain complementarity determining region 3
                         organism = synthetic construct
SEQUENCE: 39
QQYNGHAST                                                                            9

SEQ ID NO: 40            moltype = AA   length = 124
FEATURE                  Location/Qualifiers
source                   1..124
                         mol_type = protein
                         note = heavy chain variable region
                         organism = synthetic construct
SEQUENCE: 40
EEPLLESGGG LVQPGGSLRL SCAASGFTFR LYAMNWVRQA PGKGLEWVSL ISGSGTATYY    60
ADSVTGRFSI SRDNYKNRVY LQMDSLRADD TATYYCAKTY PTWGGVVIGA IDVWGQGTTV   120
TVSS                                                               124

SEQ ID NO: 41            moltype = AA   length = 107
FEATURE                  Location/Qualifiers
source                   1..107
                         mol_type = protein
                         note = light chain variable region
                         organism = synthetic construct
SEQUENCE: 41
DIQMTQSPST LSASVGDRVT ITCRASQSIQ RWLAWHQQKP GRAPKVLIHD ASTLESGVPS    60
RFSGSGSGTE FTLTISSLQP DDFATYYCQQ YNGHASTFGP GTKVDIK                107

SEQ ID NO: 42            moltype = AA   length = 454
FEATURE                  Location/Qualifiers
source                   1..454
                         mol_type = protein
                         note = full length heavy chain
                         organism = synthetic construct
SEQUENCE: 42
EEPLLESGGG LVQPGGSLRL SCAASGFTFR LYAMNWVRQA PGKGLEWVSL ISGSGTATYY    60
ADSVTGRFSI SRDNYKNRVY LQMDSLRADD TATYYCAKTY PTWGGVVIGA IDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                              454

SEQ ID NO: 43            moltype = AA   length = 214
FEATURE                  Location/Qualifiers
source                   1..214
                         mol_type = protein
                         note = full length light chain
                         organism = synthetic construct
SEQUENCE: 43
DIQMTQSPST LSASVGDRVT ITCRASQSIQ RWLAWHQQKP GRAPKVLIHD ASTLESGVPS    60
RFSGSGSGTE FTLTISSLQP DDFATYYCQQ YNGHASTFGP GTKVDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 44            moltype = AA   length = 17
FEATURE                  Location/Qualifiers
source                   1..17
                         mol_type = protein
                         note = heavy chain complementarity determining region 2
                         organism = synthetic construct
SEQUENCE: 44
LISGSGTATY YADSVKG                                                  17

SEQ ID NO: 45            moltype = AA   length = 124
FEATURE                  Location/Qualifiers
source                   1..124
                         mol_type = protein
                         note = heavy chain variable region
                         organism = synthetic construct
SEQUENCE: 45
EEPLLESGGG LVQPGGSLRL SCAASGFTFR LYAMNWVRQA PGKGLEWVSL ISGSGTATYY    60
ADSVKGRFSI SRDNSKNRVY LQMSSLRADD TATYYCAKTY PTWGGVVIGA IDVWGQGTTV   120
```

```
TVSS                                                                    124

SEQ ID NO: 46           moltype = AA  length = 454
FEATURE                 Location/Qualifiers
source                  1..454
                        mol_type = protein
                        note = full length heavy chain
                        organism = synthetic construct
SEQUENCE: 46
EEPLLESGGG LVQPGGSLRL SCAASGFTFR LYAMNWVRQA PGKGLEWVSL ISGSGTATYY       60
ADSVKGRFSI SRDNSKNRVY LQMSSLRADD TATYYCAKTY PTWGGVVIGA IDVWGQGTTV       120
TVSSASTKGP SVFPLAPSSK STSGGTAALG CLVKDYFPEP VTVSWNSGAL TSGVHTFPAV       180
LQSSGLYSLS SVVTVPSSSL GTQTYICNVN HKPSNTKVDK KVEPKSCDKT HTCPPCPAPE       240
LLGGPSVFLF PPKPKDTLMI SRTPEVTCVV VDVSHEDPEV KFNWYVDGVE VHNAKTKPRE       300
EQYNSTYRVV SVLTVLHQDW LNGKEYKCKV SNKALPAPIE KTISKAKGQP REPQVYTLPP       360
SREEMTKNQV SLTCLVKGFY PSDIAVEWES NGQPENNYKT TPPVLDSDGS FFLYSKLTVD       420
KSRWQQGNVF SCSVMHEALH NHYTQKSLSL SPGK                                  454

SEQ ID NO: 47           moltype = AA  length = 214
FEATURE                 Location/Qualifiers
source                  1..214
                        mol_type = protein
                        note = full length light chain
                        organism = synthetic construct
SEQUENCE: 47
DIQMTQSPST LSASVGDRVT ITCRASQSIQ RWLAWHQQKP GRAPKVLIHD ASTLESGVPS       60
RFSGSGSGTE FTLTISSLQP DDFATYYCQQ YNGHASTFGP GTKVDIKRTV AAPSVFIFPP       120
SDEQLKSGTA SVVCLLNNFY PREAKVQWKV DNALQSGNSQ ESVTEQDSKD STYSLSSTLT       180
LSKADYEKHK VYACEVTHQG LSSPVTKSFN RGEC                                  214

SEQ ID NO: 48           moltype = AA  length = 9
FEATURE                 Location/Qualifiers
source                  1..9
                        mol_type = protein
                        note = light chain complementarity determining region 3
                        organism = synthetic construct
SEQUENCE: 48
QQYSGHAST                                                              9

SEQ ID NO: 49           moltype = AA  length = 124
FEATURE                 Location/Qualifiers
source                  1..124
                        mol_type = protein
                        note = heavy chain variable region
                        organism = synthetic construct
SEQUENCE: 49
EEPLLESGGG LVQPGGSLRL SCAASGFTFR LYAMNWVRQA PGKGLEWVSL ISGSGTATYY       60
ADSVKGRFTI SRDNSKNRVY LQMSSLRADD TAVYYCAKTY PTWGGVVIGA IDVWGQGTTV       120
TVSS                                                                   124

SEQ ID NO: 50           moltype = AA  length = 107
FEATURE                 Location/Qualifiers
source                  1..107
                        mol_type = protein
                        note = light chain variable region
                        organism = synthetic construct
SEQUENCE: 50
DIQMTQSPST LSASVGDRVT ITCRASQSIQ RWLAWHQQKP GKAPKLLIHD ASTLESGVPS       60
RFSGSGSGTE FTLTISSLQP DDFATYYCQQ YSGHASTFGP GTKVDIK                    107

SEQ ID NO: 51           moltype = AA  length = 454
FEATURE                 Location/Qualifiers
source                  1..454
                        mol_type = protein
                        note = full length heavy chain
                        organism = synthetic construct
SEQUENCE: 51
EEPLLESGGG LVQPGGSLRL SCAASGFTFR LYAMNWVRQA PGKGLEWVSL ISGSGTATYY       60
ADSVKGRFTI SRDNSKNRVY LQMSSLRADD TAVYYCAKTY PTWGGVVIGA IDVWGQGTTV       120
TVSSASTKGP SVFPLAPSSK STSGGTAALG CLVKDYFPEP VTVSWNSGAL TSGVHTFPAV       180
LQSSGLYSLS SVVTVPSSSL GTQTYICNVN HKPSNTKVDK KVEPKSCDKT HTCPPCPAPE       240
LLGGPSVFLF PPKPKDTLMI SRTPEVTCVV VDVSHEDPEV KFNWYVDGVE VHNAKTKPRE       300
EQYNSTYRVV SVLTVLHQDW LNGKEYKCKV SNKALPAPIE KTISKAKGQP REPQVYTLPP       360
SREEMTKNQV SLTCLVKGFY PSDIAVEWES NGQPENNYKT TPPVLDSDGS FFLYSKLTVD       420
KSRWQQGNVF SCSVMHEALH NHYTQKSLSL SPGK                                  454

SEQ ID NO: 52           moltype = AA  length = 214
FEATURE                 Location/Qualifiers
source                  1..214
```

```
                        mol_type = protein
                        note = full length light chain
                        organism = synthetic construct
SEQUENCE: 52
DIQMTQSPST LSASVGDRVT  ITCRASQSIQ RWLAWHQQKP  GKAPKLLIHD ASTLESGVPS   60
RFSGSGSGTE FTLTISSLQP  DDFATYYCQQ YSGHASTFGP  GTKVDIKRTV AAPSVFIFPP  120
SDEQLKSGTA SVVCLLNNFY  PREAKVQWKV DNALQSGNSQ  ESVTEQDSKD STYSLSSTLT  180
LSKADYEKHK VYACEVTHQG  LSSPVTKSFN RGEC                               214

SEQ ID NO: 53           moltype = DNA  length = 20
FEATURE                 Location/Qualifiers
source                  1..20
                        mol_type = other DNA
                        note = qPCR primer
                        organism = synthetic construct
SEQUENCE: 53
ggatgggcag cctatgtatg                                                 20

SEQ ID NO: 54           moltype = DNA  length = 20
FEATURE                 Location/Qualifiers
source                  1..20
                        mol_type = other DNA
                        note = qPCR primer
                        organism = synthetic construct
SEQUENCE: 54
tcatatctgg gtcccctgga                                                 20

SEQ ID NO: 55           moltype = DNA  length = 20
FEATURE                 Location/Qualifiers
source                  1..20
                        mol_type = other DNA
                        note = qPCR probe
                        organism = synthetic construct
SEQUENCE: 55
agggtgtttg atggcacaga                                                 20
```

ANTI-BK VIRUS ANTIBODY MOLECULES

CROSS-REFERENCE TO RELATED APPLICATIONS

This application is a continuation of International Application No. PCT/EP2021/065462, filed Jun. 9, 2021, which is incorporated herein by reference in its entirety.

REFERENCE TO A SEQUENCE LISTING SUBMITTED ELECTRONICALLY VIA EFS-WEB

The content of the electronically submitted sequence listing in ASCII text file (Name: 4650_0030003_Seqlisting_ST26.xml; Size: 67,569 bytes; and Date of Creation: Oct. 5, 2022) filed with the application is herein incorporated by reference in its entirety.

FIELD

The present disclosure relates to anti-BK virus antibody molecules or binding fragments thereof. The present disclosure further relates to nucleic acids encoding the antibody molecules or binding fragments thereof, expression vectors, host cells and methods for making the antibody molecules or binding fragments thereof. Pharmaceutical compositions comprising the antibody molecules or binding fragments thereof are also provided. The anti-BK virus antibody molecules or binding fragments thereof of the present disclosure can be used (alone or in combination with other agents or therapeutic modalities) to treat or prevent a BK virus infection and/or a BK virus associated disorder. Thus, the present disclosure further relates to anti-BK virus antibody molecules or binding fragments thereof, or pharmaceutical compositions comprising anti-BK virus antibody molecules or binding fragments thereof, for use in treatment or prevention of a BK virus infection and/or a BK virus associated disorder. Diagnostic composition comprising the antibody molecule or binding fragment thereof are also provided.

BACKGROUND

Immunosuppressive drugs are the standard of care treatment for transplant recipients to allow engraftment and to prevent graft rejection. Immunosuppression may trigger reactivation of the human BK polyomavirus e.g. in 40 to 50% of kidney transplant recipients (Hurdiss et al., Structure, 2016 Apr. 5; 24(4):528-536) and in up to 10% of cases this leads to BK virus (BKV) associated nephropathy (BK-VAN)(Bennett et al., Microbes Infect, 2012 August; 14(9): 672-83, Rinaldo et al, APMIS, 2013 August; 121(8):728-45). BKVAN is a serious threat and may result in a loss of graft function or even graft loss (Ramos et al., Transplantation, 2009 Mar. 15; 87(5):621-30). The use of antivirals has been met with inconsistent efficacy results and is not considered a valuable treatment option (Santeusanio et al. Am J Health Syst Pharm, 2017 Dec. 15; 74(24):2037-2045; Kable et al., Transplant Direct, 2017 Mar. 10; 3(4):e142).

The standard of care for an acute viremia is thus to lower immunosuppression to allow the immune system to control the virus. However, this leads to a significant risk of short- and long-term graft dysfunction due to host vs graft immune reactions such as the formation of donor-specific antibodies.

In view of the ongoing need for improved strategies for a prophylactic or curative therapy in immunosuppressed patients, new compositions for neutralizing BK virus activity are highly desirable.

SUMMARY

Aspect A

In one aspect A1, the present disclosure relates to an anti-BK virus antibody molecule or an anti-BK virus binding fragment thereof.

Structural Properties

In some embodiments of aspect A1, the present disclosure relates to an anti-BK virus antibody molecule or an anti-BK virus binding fragment thereof, wherein the antibody molecule or binding fragment comprises at least one, two, three, four, five or six complementarity determining regions (CDRs) (or collectively all of the CDRs) from a heavy chain variable region (VH) and/or a light chain variable region (VL) comprising an amino acid sequence shown in Table 3, wherein one or more of the CDRs (or collectively all of the CDRs) may have one, two, three, four, five, six or more changes, e.g., amino acid substitutions (e.g., conservative amino acid substitutions), insertions or deletions, relative to an amino acid sequence shown in Table 3.

In some embodiments of aspect A1, the present disclosure relates to an anti-BK virus antibody molecule or an anti-BK virus binding fragment thereof, comprising:
  a heavy chain variable region (VH) comprising one, two, or three of: a heavy chain complementarity determining region 1 (VHCDR1) amino acid sequence of SEQ ID NO: 21 or a sequence having one, two, three, or four amino acid substitutions (e.g., conservative amino acid substitutions), insertions or deletions, a heavy chain complementarity determining region 2 (VHCDR2) amino acid sequence of SEQ ID NO: 22 or a sequence having one, two, three, or four amino acid substitutions (e.g., conservative amino acid substitutions), insertions or deletions, and a heavy chain complementarity determining region 3 (VHCDR3) amino acid sequence of SEQ ID NO: 23 or a sequence having one, two, three, or four amino acid substitutions (e.g., conservative amino acid substitutions), insertions or deletions; and/or a light chain variable region (VL) comprising one, two, or three of: a light chain complementarity determining region 1 (VLCDR1) amino acid sequence of SEQ ID NO: 24 or a sequence having one, two, three, or four amino acid substitutions (e.g., conservative amino acid substitutions), insertions or deletions, a light chain complementarity determining region 2 (VLCDR2) amino acid sequence of SEQ ID NO: 25 or a sequence having one, two, three, or four amino acid substitutions (e.g., conservative amino acid substitutions), insertions or deletions, and a light chain complementarity determining region 3 (VLCDR3) amino acid sequence of SEQ ID NO: 26 or a sequence having one, two, three, or four amino acid substitutions (e.g., conservative amino acid substitutions), insertions or deletions.

In some embodiments of aspect A1, the present disclosure relates to an anti-BK virus antibody molecule or an anti-BK virus binding fragment thereof comprising:
  a heavy chain variable region (VH) comprising a heavy chain complementarity determining region 3 (VHCDR3) amino acid sequence of SEQ ID NO: 23, or a sequence having one, two, three, or four amino acid substitutions (e.g., conservative amino acid substitutions); and/or a light chain variable region (VL) comprising a light chain complementarity determining region 3 (VLCDR3) amino acid sequence of SEQ ID NO: 26, or a sequence having one, two, three, or four amino acid substitutions (e.g., conservative amino acid substitutions).

In some embodiments of aspect A1, the present disclosure relates to an anti-BK virus antibody molecule or an anti-BK virus binding fragment thereof, comprising:

a heavy chain variable region (VH) comprising a heavy chain complementarity determining region 1 (VHCDR1) amino acid sequence of SEQ ID NO: 21 or a sequence having one, two, three, or four amino acid substitutions (e.g., conservative amino acid substitutions), a heavy chain complementarity determining region 2 (VHCDR2) amino acid sequence of SEQ ID NO: 22 or a sequence having one, two, three, or four amino acid substitutions (e.g., conservative amino acid substitutions), and a heavy chain complementarity determining region 3 (VHCDR3) amino acid sequence of SEQ ID NO: 23 or a sequence having one, two, three, or four amino acid substitutions (e.g., conservative amino acid substitutions); and/or a light chain variable region (VL) comprising a light chain complementarity determining region 1 (VLCDR1) amino acid sequence of SEQ ID NO: 24 or a sequence having one, two, three, or four amino acid substitutions (e.g., conservative amino acid substitutions), a light chain complementarity determining region 2 (VLCDR2) amino acid sequence of SEQ ID NO: 25 or a sequence having one, two, three, or four amino acid substitutions (e.g., conservative amino acid substitutions), and a light chain complementarity determining region 3 (VLCDR3) amino acid sequence of SEQ ID NO: 26 or a sequence having one, two, three, or four amino acid substitutions (e.g., conservative amino acid substitutions).

In some embodiments of aspect A1, the present disclosure relates to an anti-BK virus antibody molecule or an anti-BK virus binding fragment thereof, comprising:

a heavy chain variable region (VH) comprising a heavy chain complementarity determining region 1 (VHCDR1) amino acid sequence of SEQ ID NO: 21, a heavy chain complementarity determining region 2 (VHCDR2) amino acid sequence of SEQ ID NO: 22 or a sequence having one, two, or three amino acid substitutions, and a heavy chain complementarity determining region 3 (VHCDR3) amino acid sequence of SEQ ID NO: 23; and/or a light chain variable region (VL) comprising a light chain complementarity determining region 1 (VLCDR1) amino acid sequence of SEQ ID NO: 24 or a sequence having one, or two amino acid substitutions, a light chain complementarity determining region 2 (VLCDR2) amino acid sequence of SEQ ID NO: 25, and a light chain complementarity determining region 3 (VLCDR3) amino acid sequence of SEQ ID NO: 26 or a sequence having one, two, three, or four amino acid substitutions.

In some embodiments of aspect A1, the anti-BK virus antibody molecule or an anti-BK virus binding fragment thereof comprises:

a heavy chain variable region (VH) comprising a heavy chain complementarity determining region 1 (VHCDR1) amino acid sequence of SEQ ID NO: 21, a heavy chain complementarity determining region 2 (VHCDR2) amino acid sequence of SEQ ID NO: 22, and a heavy chain complementarity determining region 3 (VHCDR3) amino acid sequence of SEQ ID NO: 23; and a light chain variable region (VL) comprising a light chain complementarity determining region 1 (VLCDR1) amino acid sequence of SEQ ID NO: 24, a light chain complementarity determining region 2 (VLCDR2) amino acid sequence of SEQ ID NO: 25, and a light chain complementarity determining region 3 (VLCDR3) amino acid sequence of SEQ ID NO: 26, wherein one or two amino acids within a CDR have been inserted, deleted or substituted.

In some embodiments of aspect A1, the anti-BK virus antibody molecule or an anti-BK virus binding fragment thereof comprises:

a heavy chain variable region (VH) comprising a heavy chain complementarity determining region 1 (VHCDR1) amino acid sequence of SEQ ID NO: 21, a heavy chain complementarity determining region 2 (VHCDR2) amino acid sequence of SEQ ID NO: 22, and a heavy chain complementarity determining region 3 (VHCDR3) amino acid sequence of SEQ ID NO: 23; and a light chain variable region (VL) comprising a light chain complementarity determining region 1 (VLCDR1) amino acid sequence of SEQ ID NO: 24, a light chain complementarity determining region 2 (VLCDR2) amino acid sequence of SEQ ID NO: 25, and a light chain complementarity determining region 3 (VLCDR3) amino acid sequence of SEQ ID NO: 26.

In some embodiments of aspect A1, the anti-BK virus antibody molecule or an anti-BK virus binding fragment thereof comprises a heavy chain variable region (VH) comprising the amino acid sequence of SEQ ID NO: 27, or an amino acid sequence having at least about 85%, 90%, 95%, or 99% sequence identity to SEQ ID NO: 27.

In some embodiments of aspect A1, the anti-BK virus antibody molecule or an anti-BK virus binding fragment thereof comprises (i) a light chain variable region (VL) comprising the amino acid sequence of SEQ ID NO: 28, or an amino acid sequence having at least about 85%, 90%, 95%, or 99% sequence identity to SEQ ID NO: 28; or (ii) a light chain variable region (VL) comprising the amino acid sequence of SEQ ID NO: 31, or an amino acid sequence having at least about 85%, 90%, 95%, or 99% sequence identity to SEQ ID NO: 31.

In some embodiments of aspect A1, the anti-BK virus antibody molecule or an anti-BK virus binding fragment thereof comprises (i) a heavy chain variable region (VH) comprising the amino acid sequence of SEQ ID NO: 27, or an amino acid sequence having at least about 85%, 90%, 95%, or 99% sequence identity to SEQ ID NO: 27; and a light chain variable region (VL) comprising the amino acid sequence of SEQ ID NO: 28, or an amino acid sequence having at least about 85%, 90%, 95%, or 99% sequence identity to SEQ ID NO: 28; or (ii) a heavy chain variable region (VH) comprising the amino acid sequence of SEQ ID NO: 27, or an amino acid sequence having at least about 85%, 90%, 95%, or 99% sequence identity to SEQ ID NO: 27; and a light chain variable region (VL) comprising the amino acid sequence of SEQ ID NO: 31, or an amino acid sequence having at least about 85%, 90%, 95%, or 99% sequence identity to SEQ ID NO: 31.

In some embodiments of aspect A1, the anti-BK virus antibody molecule or an anti-BK virus binding fragment thereof comprises
(i) a heavy chain variable region (VH) comprising the amino acid sequence of SEQ ID NO: 27, and a light chain variable region (VL) comprising the amino acid sequence of SEQ ID NO: 28; or
(ii) a heavy chain variable region (VH) comprising the amino acid sequence of SEQ ID NO: 27, and a light chain variable region (VL) comprising the amino acid sequence of SEQ ID NO: 31.

Functional Properties

In some embodiments of aspect A1, the anti-BK virus antibody molecule or an anti-BK virus binding fragment thereof comprises one or more (e.g., 2, 3, 4, 5, 6, 7, 8 or 9) of the following properties:
(i) binds to BK virus serotype I VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(ii) binds to BK virus serotype II VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(iii) binds to BK virus serotype III VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(iv) binds to BK virus serotype IV VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(v) does not bind to JC virus VP1; e.g., as described in Example 6;
(vi) neutralizes BK virus serotype I;
(vii) neutralizes BK virus serotype II;
(viii) neutralizes BK virus serotype III;
(ix) neutralizes BK virus serotype IV.

In one aspect A2, the present disclosure relates to an antibody molecule or a binding fragment thereof that competes for binding to BK virus serotype I VP1, BK virus serotype II VP1, BK virus serotype III VP1, and/or BK virus serotype IV VP1 with an antibody molecule or a binding fragment thereof described herein. In some embodiments of aspect A2, the present disclosure relates to an antibody molecule or a binding fragment thereof that competes for binding to BK virus genotype I VP1, BK virus genotype II VP1, BK virus genotype III VP1, and/or BK virus genotype IV VP1 with an antibody molecule or a binding fragment thereof that comprises a heavy chain variable region (VH) comprising a heavy chain complementarity determining region 1 (VHCDR1) amino acid sequence of SEQ ID NO: 21, a heavy chain complementarity determining region 2 (VHCDR2) amino acid sequence of SEQ ID NO: 22, and a heavy chain complementarity determining region 3 (VHCDR3) amino acid sequence of SEQ ID NO: 23; and
a light chain variable region (VL) comprising a light chain complementarity determining region 1 (VLCDR1) amino acid sequence of SEQ ID NO: 24, a light chain complementarity determining region 2 (VLCDR2) amino acid sequence of SEQ ID NO: 25, and a light chain complementarity determining region 3 (VLCDR3) amino acid sequence of SEQ ID NO: 26.

In some embodiments of aspect A2, the present disclosure relates to an antibody molecule or a binding fragment thereof that competes for binding to BK virus genotype I VP1, BK virus genotype II VP1, BK virus genotype III VP1, and/or BK virus genotype IV VP1 with an antibody molecule or a binding fragment thereof that comprises (i) a heavy chain variable region (VH) comprising the amino acid sequence of SEQ ID NO: 27, and a light chain variable region (VL) comprising the amino acid sequence of SEQ ID NO: 28; or
(ii) a heavy chain variable region (VH) comprising the amino acid sequence of SEQ ID NO: 27, and a light chain variable region (VL) comprising the amino acid sequence of SEQ ID NO: 31.

In one aspect A3, the present disclosure relates to a pharmaceutical composition comprising the antibody molecule or binding fragment thereof described herein and a pharmaceutically acceptable carrier, excipient or stabilizer.

In one aspect A4, the present disclosure relates to anti-BK virus antibody molecules or binding fragments thereof described herein, or pharmaceutical compositions comprising anti-BK virus antibody molecules or binding fragments thereof described herein, for use in the treatment or prevention of a BK virus infection and/or a BK virus associated disorder. In some embodiments of aspect A4, the BK virus associated disorder is selected from the group consisting of nephropathy, BK virus associated nephropathy (BKVAN), hemorrhagic cystitis (HC).

In one aspect A5, the present disclosure relates to a nucleic acid encoding the antibody heavy and/or light chain variable region of the antibody molecule or binding fragment thereof described herein.

In one aspect A6, the present disclosure relates to an expression vector comprising the nucleic acid described herein.

In one aspect A7, the present disclosure relates to a host cell comprising the nucleic acid described herein or the expression vector described herein.

In one aspect A8, the present disclosure relates to a method of producing an antibody molecule, the method comprising culturing the host cell described herein under conditions suitable for gene expression.

In one aspect A9, the present disclosure relates to a diagnostic composition comprising the antibody molecule or binding fragment thereof described herein.

Aspect B

In one aspect B1, the present disclosure relates to an anti-BK virus antibody molecule or an anti-BK virus binding fragment thereof.

Structural Properties

In some embodiments of aspect B1, the present disclosure relates to an anti-BK virus antibody molecule or an anti-BK virus binding fragment thereof, wherein the antibody molecule or binding fragment comprises at least one, two, three, four, five or six complementarity determining regions (CDRs) (or collectively all of the CDRs) from a heavy chain variable region (VH) and/or a light chain variable region (VL) comprising an amino acid sequence shown in Table 4, wherein one or more of the CDRs (or collectively all of the CDRs) may have one, two, three, four, five, six or more changes, e.g., amino acid substitutions (e.g., conservative amino acid substitutions), insertions or deletions, relative to an amino acid sequence shown in Table 4.

In some embodiments of aspect B1, the present disclosure relates to an anti-BK virus antibody molecule or an anti-BK virus binding fragment thereof, comprising:
(i) a heavy chain variable region (VH) comprising one, two, or three of: a heavy chain complementarity determining region 1 (VHCDR1) amino acid sequence of SEQ ID NO: 34 or a sequence having one, two, three, or four amino acid substitutions (e.g., conservative amino acid substitutions), insertions or deletions, a heavy chain complementarity determining region 2 (VHCDR2) amino acid sequence of SEQ ID NO: 35 or a sequence having one, two, three, or four amino acid substitutions (e.g., conservative amino acid substitutions), insertions or deletions, and a heavy chain complementarity determining region 3 (VHCDR3) amino acid sequence of SEQ ID NO: 36 or a sequence having one, two, three, or four amino acid substitutions (e.g., conservative amino acid substitutions), insertions or deletions; and/or a light chain variable region (VL) comprising one, two, or three of: a light chain complementarity determining region 1 (VLCDR1) amino acid sequence of SEQ ID NO: 37 or a sequence having one, two, three, or four amino acid substitutions (e.g., conservative amino acid substitutions), insertions or deletions, a light chain complementarity determining region 2 (VLCDR2) amino acid sequence of SEQ ID NO: 38 or a sequence having one, two, three, or four amino acid substitutions (e.g., conservative amino acid substitutions), insertions or deletions, and a light chain complementarity determining region 3 (VLCDR3) amino acid sequence of SEQ ID NO: 39 or a sequence having one, two, three, or four amino acid substitutions (e.g., conservative amino acid substitutions), insertions or deletions; or
(ii) a heavy chain variable region (VH) comprising one, two, or three of: a heavy chain complementarity determining region 1 (VHCDR1) amino acid sequence of SEQ ID NO: 34 or a sequence having one, two, three, or four amino acid substitutions (e.g., conservative amino acid substitutions), insertions or deletions, a heavy chain complementarity determining region 2 (VHCDR2) amino acid sequence of SEQ ID NO: 44 or a sequence having one, two, three, or four amino acid substitutions (e.g., conservative amino acid substitutions), insertions or deletions, and a heavy chain complementarity determining region 3 (VHCDR3) amino acid sequence of SEQ ID NO: 36 or a sequence having one, two, three, or four amino acid substitutions (e.g., conservative amino acid substitutions), insertions or deletions; and/or a light chain variable region (VL) comprising one, two, or three of: a light chain complementarity determining region 1 (VLCDR1) amino acid sequence of SEQ ID NO: 37 or a sequence having one, two, three, or four amino acid substitutions (e.g., conservative amino acid substitutions), insertions or deletions, a light chain complementarity determining region 2 (VLCDR2) amino acid sequence of SEQ ID NO: 38 or a sequence having one, two, three, or four amino acid substitutions (e.g., conservative amino acid substitutions), insertions or deletions, and a light chain complementarity determining region 3 (VLCDR3) amino acid sequence of SEQ ID NO: 39 or a sequence having one, two, three, or four amino acid substitutions (e.g., conservative amino acid substitutions), insertions or deletions; or
(iii) a heavy chain variable region (VH) comprising one, two, or three of: a heavy chain complementarity determining region 1 (VHCDR1) amino acid sequence of SEQ ID NO: 34 or a sequence having one, two, three, or four amino acid substitutions (e.g., conservative amino acid substitutions), insertions or deletions, a heavy chain complementarity determining region 2 (VHCDR2) amino acid sequence of SEQ ID NO: 44 or a sequence having one, two, three, or four amino acid substitutions (e.g., conservative amino acid substitutions), insertions or deletions, and a heavy chain complementarity determining region 3 (VHCDR3) amino acid sequence of SEQ ID NO: 36 or a sequence having one, two, three, or four amino acid substitutions (e.g., conservative amino acid substitutions), insertions or deletions; and/or a light chain variable region (VL) comprising one, two, or three of: a light chain complementarity determining region 1 (VLCDR1) amino acid sequence of SEQ ID NO: 37 or a sequence having one, two, three, or four amino acid substitutions (e.g., conservative amino acid substitutions), insertions or deletions, a light chain complementarity determining region 2 (VLCDR2) amino acid sequence of SEQ ID NO: 38 or a sequence having one, two, three, or four amino acid substitutions (e.g., conservative amino acid substitutions), insertions or deletions, and a light chain complementarity determining region 3 (VLCDR3) amino acid sequence of SEQ ID NO: 48 or a sequence having one, two, three, or four amino acid substitutions (e.g., conservative amino acid substitutions), insertions or deletions.

In some embodiments of aspect B1, the present disclosure relates to an anti-BK virus antibody molecule or an anti-BK virus binding fragment thereof comprising:
(i) a heavy chain variable region (VH) comprising a heavy chain complementarity determining region 3 (VHCDR3) amino acid sequence of SEQ ID NO: 36, or a sequence having one, two, three, or four amino acid substitutions (e.g., conservative amino acid substitutions); and/or
a light chain variable region (VL) comprising a light chain complementarity determining region 3 (VLCDR3) amino acid sequence of SEQ ID NO: 39, or a sequence having one, two, three, or four amino acid substitutions (e.g., conservative amino acid substitutions); or
(ii) a heavy chain variable region (VH) comprising a heavy chain complementarity determining region 3 (VHCDR3) amino acid sequence of SEQ ID NO: 36, or a sequence having one, two, three, or four amino acid substitutions (e.g., conservative amino acid substitutions); and/or
a light chain variable region (VL) comprising a light chain complementarity determining region 3 (VLCDR3) amino acid sequence of SEQ ID NO: 48, or a sequence having one, two, three, or four amino acid substitutions (e.g., conservative amino acid substitutions).

In some embodiments of aspect B1, the present disclosure relates to an anti-BK virus antibody molecule or an anti-BK virus binding fragment thereof, comprising:
- (i) a heavy chain variable region (VH) comprising a heavy chain complementarity determining region 1 (VHCDR1) amino acid sequence of SEQ ID NO: 34 or a sequence having one, two, three, or four amino acid substitutions (e.g., conservative amino acid substitutions), a heavy chain complementarity determining region 2 (VHCDR2) amino acid sequence of SEQ ID NO: 35 or a sequence having one, two, three, or four amino acid substitutions (e.g., conservative amino acid substitutions), and a heavy chain complementarity determining region 3 (VHCDR3) amino acid sequence of SEQ ID NO: 36 or a sequence having one, two, three, or four amino acid substitutions (e.g., conservative amino acid substitutions); and/or
- a light chain variable region (VL) comprising a light chain complementarity determining region 1 (VLCDR1) amino acid sequence of SEQ ID NO: 37 or a sequence having one, two, three, or four amino acid substitutions (e.g., conservative amino acid substitutions), a light chain complementarity determining region 2 (VLCDR2) amino acid sequence of SEQ ID NO: 38 or a sequence having one, two, three, or four amino acid substitutions (e.g., conservative amino acid substitutions), and a light chain complementarity determining region 3 (VLCDR3) amino acid sequence of SEQ ID NO: 39 or a sequence having one, two, three, or four amino acid substitutions (e.g., conservative amino acid substitutions); or
- (ii) a heavy chain variable region (VH) comprising a heavy chain complementarity determining region 1 (VHCDR1) amino acid sequence of SEQ ID NO: 34 or a sequence having one, two, three, or four amino acid substitutions (e.g., conservative amino acid substitutions), a heavy chain complementarity determining region 2 (VHCDR2) amino acid sequence of SEQ ID NO: 44 or a sequence having one, two, three, or four amino acid substitutions (e.g., conservative amino acid substitutions), and a heavy chain complementarity determining region 3 (VHCDR3) amino acid sequence of SEQ ID NO: 36 or a sequence having one, two, three, or four amino acid substitutions (e.g., conservative amino acid substitutions); and/or
- a light chain variable region (VL) comprising a light chain complementarity determining region 1 (VLCDR1) amino acid sequence of SEQ ID NO: 37 or a sequence having one, two, three, or four amino acid substitutions (e.g., conservative amino acid substitutions), a light chain complementarity determining region 2 (VLCDR2) amino acid sequence of SEQ ID NO: 38 or a sequence having one, two, three, or four amino acid substitutions (e.g., conservative amino acid substitutions), and a light chain complementarity determining region 3 (VLCDR3) amino acid sequence of SEQ ID NO: 39 or a sequence having one, two, three, or four amino acid substitutions (e.g., conservative amino acid substitutions); or or
- (iii) a heavy chain variable region (VH) comprising a heavy chain complementarity determining region 1 (VHCDR1) amino acid sequence of SEQ ID NO: 34 or a sequence having one, two, three, or four amino acid substitutions (e.g., conservative amino acid substitutions), a heavy chain complementarity determining region 2 (VHCDR2) amino acid sequence of SEQ ID NO: 44 or a sequence having one, two, three, or four amino acid substitutions (e.g., conservative amino acid substitutions), and a heavy chain complementarity determining region 3 (VHCDR3) amino acid sequence of SEQ ID NO: 36 or a sequence having one, two, three, or four amino acid substitutions (e.g., conservative amino acid substitutions); and/or
- a light chain variable region (VL) comprising a light chain complementarity determining region 1 (VLCDR1) amino acid sequence of SEQ ID NO: 37 or a sequence having one, two, three, or four amino acid substitutions (e.g., conservative amino acid substitutions), a light chain complementarity determining region 2 (VLCDR2) amino acid sequence of SEQ ID NO: 38 or a sequence having one, two, three, or four amino acid substitutions (e.g., conservative amino acid substitutions), and a light chain complementarity determining region 3 (VLCDR3) amino acid sequence of SEQ ID NO: 48 or a sequence having one, two, three, or four amino acid substitutions (e.g., conservative amino acid substitutions).

In some embodiments of aspect B1, the present disclosure relates to an anti-BK virus antibody molecule or an anti-BK virus binding fragment thereof, comprising:
- (i) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 35 or a sequence having one, two, or three amino acid substitutions, and a heavy chain complementarity determining region 3 (VHCDR3) amino acid sequence of SEQ ID NO: 36; and/or
- a light chain variable region (VL) comprising a light chain complementarity determining region 1 (VLCDR1) amino acid sequence of SEQ ID NO: 37 or a sequence having one, or two amino acid substitutions, a light chain complementarity determining region 2 (VLCDR2) amino acid sequence of SEQ ID NO: 38, and a light chain complementarity determining region 3 (VLCDR3) amino acid sequence of SEQ ID NO: 39 or a sequence having one, two, three, or four amino acid substitutions; or
- (ii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44 or a sequence having one, two, or three amino acid substitutions, and a heavy chain complementarity determining region 3 (VHCDR3) amino acid sequence of SEQ ID NO: 36; and/or
- a light chain variable region (VL) comprising a light chain complementarity determining region 1 (VLCDR1) amino acid sequence of SEQ ID NO: 37 or a sequence having one, or two amino acid substitutions, a light chain complementarity determining region 2 (VLCDR2) amino acid sequence of SEQ ID NO: 38, and a light chain complementarity determining region 3 (VLCDR3) amino acid sequence of SEQ ID NO: 39 or a sequence having one, two, three, or four amino acid substitutions; or
- (iii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44 or a sequence having one, two, or three amino acid substitutions, and a heavy chain complementarity determining region 3 (VHCDR3) amino acid sequence of SEQ ID NO: 36; and/or a light chain variable region (VL) comprising a light chain complementarity determining region 1 (VLCDR1) amino acid sequence of SEQ ID NO: 37 or a sequence having one, or two amino acid substitutions, a light chain complementarity determining region 2 (VLCDR2) amino acid sequence of SEQ ID NO: 38, and a light chain complementarity determining region 3 (VLCDR3) amino acid sequence of SEQ ID NO: 48 or a sequence having one, two, three, or four amino acid substitutions.

In some embodiments of aspect B1, the anti-BK virus antibody molecule or an anti-BK virus binding fragment thereof comprises:
- (i) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 35, and a heavy chain complementarity determining region 3 (VHCDR3) amino acid sequence of SEQ ID NO: 36; and
- a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39;
- wherein one or two amino acids within a CDR have been inserted, deleted or substituted;
- or
- (ii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and
- a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39;
- wherein one or two amino acids within a CDR have been inserted, deleted or substituted;
- or
- (iii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and
- a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 48;
- wherein one or two amino acids within a CDR have been inserted, deleted or substituted;

In some embodiments of aspect B1, the anti-BK virus antibody molecule or an anti-BK virus binding fragment thereof comprises:
- (i) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 35, and a heavy chain complementarity determining region 3 (VHCDR3) amino acid sequence of SEQ ID NO: 36; and
- a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39; or
- (ii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and
- a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39; or
- (iii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and
- a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 48.

In some embodiments of aspect B1, the anti-BK virus antibody molecule or an anti-BK virus binding fragment thereof comprises (i) a heavy chain variable region (VH) comprising the amino acid sequence of SEQ ID NO: 40, or an amino acid sequence having at least about 85%, 90%, 95%, or 99% sequence identity to SEQ ID NO: 40; or (ii) a heavy chain variable region (VH) comprising the amino acid sequence of SEQ ID NO: 45, or an amino acid sequence having at least about 85%, 90%, 95%, or 99% sequence identity to SEQ ID NO: 45; or (iii) a heavy chain variable region (VH) comprising the amino acid sequence of SEQ ID NO: 49, or an amino acid sequence having at least about 85%, 90%, 95%, or 99% sequence identity to SEQ ID NO: 49.

In some embodiments of aspect B1, the anti-BK virus antibody molecule or an anti-BK virus binding fragment thereof comprises (i) a light chain variable region (VL) comprising the amino acid sequence of SEQ ID NO: 41, or an amino acid sequence having at least about 85%, 90%, 95%, or 99% sequence identity to SEQ ID NO: 41; or (ii) a light chain variable region (VL) comprising the amino acid sequence of SEQ ID NO: 50, or an amino acid sequence having at least about 85%, 90%, 95%, or 99% sequence identity to SEQ ID NO: 50.

In some embodiments of aspect B1, the anti-BK virus antibody molecule or an anti-BK virus binding fragment thereof comprises
- (i) a heavy chain variable region (VH) comprising the amino acid sequence of SEQ ID NO: 40, or an amino acid sequence having at least about 85%, 90%, 95%, or 99% sequence identity to SEQ ID NO: 40; and a light chain variable region (VL) comprising the amino acid sequence of SEQ ID NO: 41, or an amino acid sequence having at least about 85%, 90%, 95%, or 99% sequence identity to SEQ ID NO: 41; or
- (ii) a heavy chain variable region (VH) comprising the amino acid sequence of SEQ ID NO: 45, or an amino acid sequence having at least about 85%, 90%, 95%, or 99% sequence identity to SEQ ID NO: 45; and a light chain variable region (VL) comprising the amino acid sequence of SEQ ID NO: 41, or an amino acid sequence having at least about 85%, 90%, 95%, or 99% sequence identity to SEQ ID NO: 41; or
- (iii) a heavy chain variable region (VH) comprising the amino acid sequence of SEQ ID NO: 49, or an amino acid sequence having at least about 85%, 90%, 95%, or 99% sequence identity to SEQ ID NO: 49; and a light chain variable region (VL) comprising the amino acid sequence of SEQ ID NO: 50, or an amino acid sequence having at least about 85%, 90%, 95%, or 99% sequence identity to SEQ ID NO: 50.

In some embodiments of aspect B1, the anti-BK virus antibody molecule or an anti-BK virus binding fragment thereof comprises
- (i) a heavy chain variable region (VH) comprising the amino acid sequence of SEQ ID NO: 40, and a light chain variable region (VL) comprising the amino acid sequence of SEQ ID NO: 41; or
- (ii) a heavy chain variable region (VH) comprising the amino acid sequence of SEQ ID NO: 45, and a light chain variable region (VL) comprising the amino acid sequence of SEQ ID NO: 41; or
- (iii) a heavy chain variable region (VH) comprising the amino acid sequence of SEQ ID NO: 49, and a light chain variable region (VL) comprising the amino acid sequence of SEQ ID NO: 50.

Functional Properties

In some embodiments of aspect B1, the anti-BK virus antibody molecule or an anti-BK virus binding fragment thereof comprises one or more (e.g., 2, 3, 4, 5, 6, 7, 8 or 9) of the following properties:
- (i) binds to BK virus serotype I VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
- (ii) binds to BK virus serotype II VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
- (iii) binds to BK virus serotype III VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
- (iv) binds to BK virus serotype IV VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
- (v) does not bind to JC virus VP1; e.g., as described in Example 6;
- (vi) neutralizes BK virus serotype I;
- (vii) neutralizes BK virus serotype II;
- (viii) neutralizes BK virus serotype III;
- (ix) neutralizes BK virus serotype IV.

In one aspect B2, the present disclosure relates to an antibody molecule or a binding fragment thereof that competes for binding to BK virus serotype I VP1, BK virus serotype II VP1, BK virus serotype III VP1, and/or BK virus serotype IV VP1 with an antibody molecule or a binding fragment thereof described herein. In some embodiments of aspect B2, the present disclosure relates to an antibody molecule or a binding fragment thereof that competes for binding to BK virus genotype I VP1, BK virus genotype II VP1, BK virus genotype III VP1, and/or BK virus genotype IV VP1 with an antibody molecule or a binding fragment thereof that comprises
- (i) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 35, and a heavy chain complementarity determining region 3 (VHCDR3) amino acid sequence of SEQ ID NO: 36; and
  a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39; or
- (ii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39; or (iii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 48.

In some embodiments of aspect B2, the present disclosure relates to an antibody molecule or a binding fragment thereof that competes for binding to BK virus genotype I VP1, BK virus genotype II VP1, BK virus genotype III VP1, and/or BK virus genotype IV VP1 with an antibody molecule or a binding fragment thereof that comprises (i) a heavy chain variable region (VH) comprising the amino acid sequence of SEQ ID NO: 40, and a light chain variable region (VL) comprising the amino acid sequence of SEQ ID NO: 41; or (ii) a heavy chain variable region (VH) comprising the amino acid sequence of SEQ ID NO: 45, and a light chain variable region (VL) comprising the amino acid sequence of SEQ ID NO: 41; or (iii) a heavy chain variable region (VH) comprising the amino acid sequence of SEQ ID NO: 49, and a light chain variable region (VL) comprising the amino acid sequence of SEQ ID NO: 50.

In one aspect B3, the present disclosure relates to a pharmaceutical composition comprising the antibody molecule or binding fragment thereof described herein and a pharmaceutically acceptable carrier, excipient or stabilizer.

In one aspect B4, the present disclosure relates to anti-BK virus antibody molecules or binding fragments thereof described herein, or pharmaceutical compositions comprising anti-BK virus antibody molecules or binding fragments thereof described herein, for use in the treatment or prevention of a BK virus infection and/or a BK virus associated disorder. In some embodiments of aspect B4, the BK virus associated disorder is selected from the group consisting of nephropathy, BK virus associated nephropathy (BKVAN), hemorrhagic cystitis (HC).

In one aspect B5, the present disclosure relates to a nucleic acid encoding the antibody heavy and/or light chain variable region of the antibody molecule or binding fragment thereof described herein.

In one aspect B6, the present disclosure relates to an expression vector comprising the nucleic acid described herein.

In one aspect B7, the present disclosure relates to a host cell comprising the nucleic acid described herein or the expression vector described herein.

In one aspect B8, the present disclosure relates to a method of producing an antibody molecule, the method comprising culturing the host cell described herein under conditions suitable for gene expression.

In one aspect B9, the present disclosure relates to a diagnostic composition comprising the antibody molecule or binding fragment thereof described herein.

BRIEF DESCRIPTION OF THE DRAWINGS

FIG. 1. Binding of anti-BK virus antibodies to BKV-VP1 serotypes I-IV in ELISA. These Data were used to determine the $EC50_E$ values by three-parameter analysis in GraphPad Prism Software.

FIG. 2. Quantitative assessment of antibody-mediated neutralization of BKV strains (serotype Ia, Ib, II, III and IV). 293TT cells were used as target for infection by luciferase expressing BK-pseudovirus formed with either serotype Ia, Ib, II, III and IV VP1. Anti-BK virus antibodies were used in the indicated concentrations.

FIG. 3. Long-term virus neutralization of wild type BKV on human primary renal tubular epithelial cells by anti-BK virus antibodies. Residual virus load after long term co-incubation of cells, BK virus and anti-BK virus antibodies at the indicated concentrations is indicated. Antibody concentrations correspond to EC 95 (1.500), EC50 (0.15) and EC5 (0.015). P8D11 is labelled with "BM2" in this figure.

FIG. 4. Binding of anti-BK virus antibodies to a conformational epitope.

FIG. 5. Assessment of binding strength in ELISA to VP1-mutants and JCV- of antibody 319C07 and antibody 336F07 compared to antibody P8D11. EC50 values to the various mutant forms of VP1 and JC-VP1 were determined in comparison to wild type VP1. VP1 mutants are designated in standard format where the number refers to position in the VP1-STI sequence that was changed from the amino acid left from the number to the amino acid right of the number.

Figure 7:
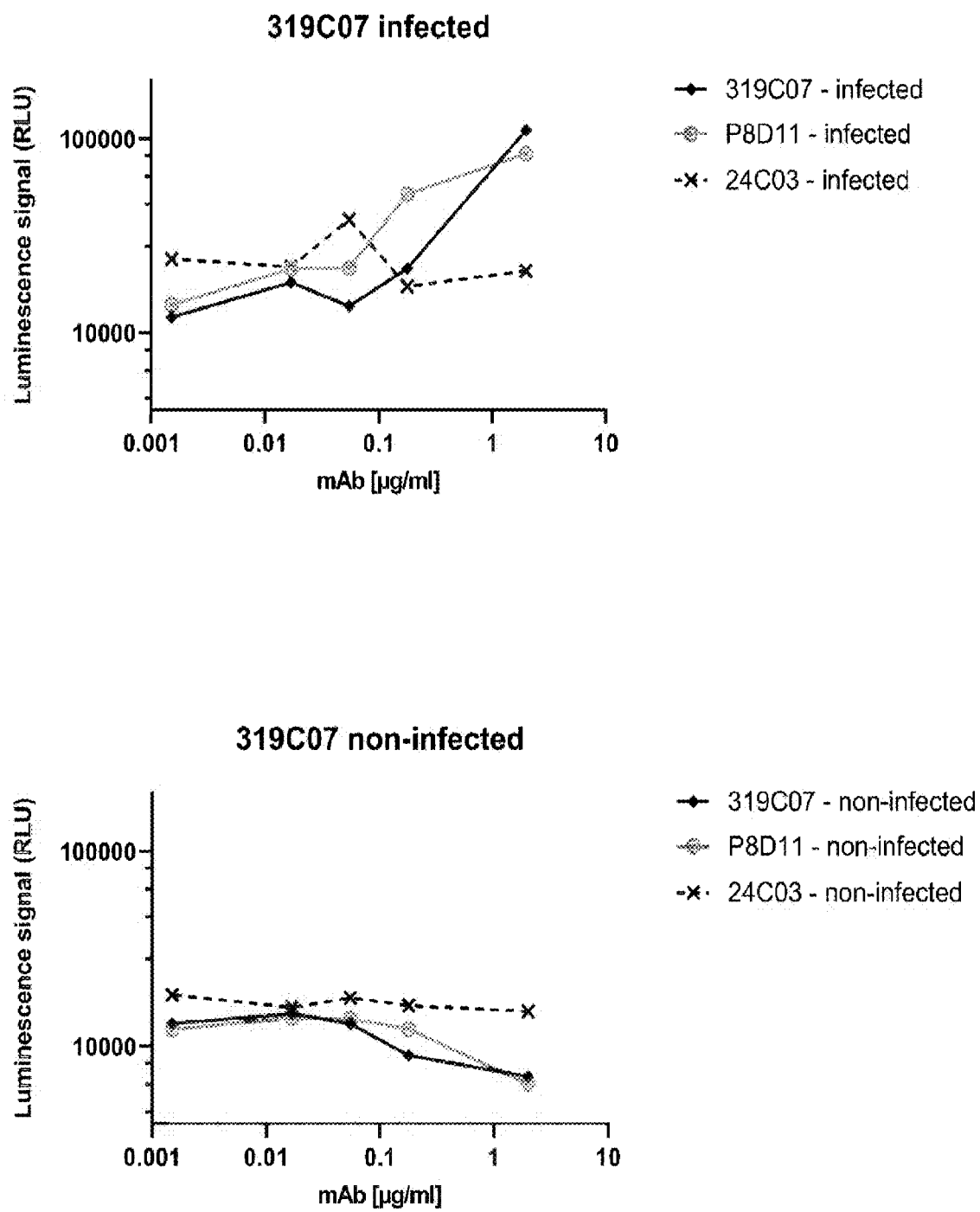

The graphs show binding of antibody 319C07, antibody 336F07, isotype control antibody 24C03 and antibody P8D11 with a selection of BKV-VP1 mutants and JCV-VP1 and as irrelevant antigen CMV-gH pentamers.

The table shows data for all BKV-VP1 mutants tested and JCV-VP1. "+" is used to designate that no difference in binding affinity observed between original sequence and mutated sequence. "red" designates a reduced binding "−" designates that no binding was observed.

FIG. 6. Inhibition of BKV spread on HRPTEC by anti-BK virus antibodies (P8D11 is labelled with "BM2" in this figure).

FIG. 7. ADCC activity of anti-BKV antibodies on infected and non-infected HPRTEC.

FIG. 8. CDC activity of anti-BKV antibodies on infected and non-infected HPRTEC in the presence of human serum.

DETAILED DESCRIPTION

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term indicates deviation from the indicated numerical value of ±20%, preferably ±10%, and more preferably of ±5%.

Technical terms are used in their common meaning. If a specific meaning is conveyed to certain terms, definitions of terms will be given in the following in the context of which the terms are used.

Certain aspects of the present disclosure are based, at least in part, on the identification of anti-BK virus antibody molecules or binding fragments thereof that
  bind to and neutralize BK virus serotype I; and/or
  bind to and neutralize neutralizes BK virus serotype II; and/or
  bind to and neutralize neutralizes BK virus serotype III; and/or
  bind to and neutralize neutralizes BK virus serotype IV; and/or
  do not bind to JC virus VP1.

In a preferred embodiment, the anti-BK virus antibody molecules or binding fragments thereof neutralize BK virus serotypes I, II, Ill, and IV.

In another preferred embodiment, the anti-BK virus antibody molecules or binding fragments thereof do not bind to JC virus VP1. Increased specificity is manifested by the absence of binding to the closely related JC virus VP1. Increased specificity is considered as better safety due to lower risk for off target reactivity.

As mentioned above, the present disclosure considers anti-BK virus antibody molecules or binding fragments thereof. A full-length antibody includes a constant domain and a variable domain. The constant region need not be present in an antigen-binding fragment of an antibody.

Binding fragments may thus include portions of an intact full-length antibody, such as an antigen binding or variable region of the complete antibody. Examples of antibody fragments include Fab, F(ab')2, Id and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), binding-domain immunoglobulin fusion proteins; camelized antibodies; VHH containing antibodies; and any other polypeptides formed from antibody fragments. The skilled person is aware that the antigen-binding function of an antibody can be performed by fragments of a full-length antibody.

Disclosed herein are polypeptides having the sequences specified, or sequences substantially identical or similar thereto, e.g. sequences having at least about 85%, 90%, 95%, or 99% sequence identity to the sequence specified.

The determination of percent identity between two sequences is preferably accomplished using the mathematical algorithm of Karlin and Altschul (1993) Proc. Natl. Acad. Sci USA 90: 5873-5877. Such an algorithm is incorporated into the BLASTp (Protein BLAST) program of Altschul et al. (1990) J. Mol. Biol. 215: 403-410 available at NCBI. The determination of percent identity may be performed with the standard parameters of the BLASTp program. For the general parameters, the "Max Target Sequences" box may be set to 100, the "Short queries" box may be ticked, the "Expect threshold" box may be set to 10, the "Word Size" box may be set to "3" and the "Max matches in a query range" may be set to "0". For the scoring parameters the "Matrix" box may be set to "BLOSUM62", the "Gap Costs" Box may be set to "Existence: 11 Extension:1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

According to the disclosure, a "conservative amino acid substitution" is an amino acid substitution in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As mentioned, the disclosure also relates in some embodiments to a nucleic acid encoding antibody molecules or binding fragments thereof, vectors comprising such nucleic acids and host cells comprising such nucleic acids or vectors.

The antibody molecules or binding fragments thereof may be encoded by a single nucleic acid (e.g., a single nucleic acid comprising nucleotide sequences that encode the light and heavy chain polypeptides of the antibody), or by two or more separate nucleic acids, each of which encode a different part of the antibody molecule or antibody fragment. The nucleic acids may be DNA, cDNA, RNA and the like.

The nucleic acids described herein can be inserted into vectors. A "vector" is any molecule or composition that has the ability to carry a nucleic acid sequence into a suitable cell where synthesis of the encoded polypeptide can take place.

The present disclosure in some aspects further provides a host cell (e.g., an isolated or purified cell) comprising a nucleic acid or vector of the invention. The host cell can be any type of cell capable of being transformed with the nucleic acid or vector of the invention so as to produce a polypeptide encoded thereby.

The anti-BK virus antibody molecules or anti-BK virus binding fragments thereof can be formulated in compositions, especially pharmaceutical compositions. Such compositions comprise a therapeutically effective amount of an antibody or binding fragment thereof in admixture with a pharmaceutically acceptable carrier, excipient or stabilizer.

Further, the anti-BK virus antibody molecules or anti-BK virus binding fragments thereof and the pharmaceutical compositions as described herein can be administered in methods of treating or preventing a BK virus infection and/or a BK virus associated disorder.

Preferred embodiments of aspects B1 to B9 of the present invention relate to:
1. An anti-BK virus antibody molecule or an anti-BK virus binding fragment thereof comprising:
   (i) a heavy chain variable region (VH) comprising a heavy chain complementarity determining region 1 (VHCDR1) amino acid sequence of SEQ ID NO: 34 or a sequence having one or two amino acid substitutions, a heavy chain complementarity determining region 2 (VHCDR2) amino acid sequence of SEQ ID NO: 35 or a sequence having one or two amino acid substitutions, and a heavy chain complementarity determining region 3 (VHCDR3) amino acid sequence of SEQ ID NO: 36 or a sequence having one or two amino acid substitutions; and
   a light chain variable region (VL) comprising a light chain complementarity determining region 1 (VLCDR1) amino acid sequence of SEQ ID NO: 37 or a sequence having one or two amino acid substitutions, a light chain complementarity determining region 2 (VLCDR2) amino acid sequence of SEQ ID NO: 38 or a sequence having one or two amino acid substitutions, and a light chain complementarity determining region 3 (VLCDR3) amino acid sequence of SEQ ID NO: 39 or a sequence having one or two amino acid substitutions; or
   (ii) a heavy chain variable region (VH) comprising a heavy chain complementarity determining region 1 (VHCDR1) amino acid sequence of SEQ ID NO: 34 or a sequence having one or two amino acid substitutions, a heavy chain complementarity determining region 2 (VHCDR2) amino acid sequence of SEQ ID NO: 44 or a sequence having one or two amino acid substitutions, and a heavy chain complementarity determining region 3 (VHCDR3) amino acid sequence of SEQ ID NO: 36 or a sequence having one or two amino acid substitutions; and
   a light chain variable region (VL) comprising a light chain complementarity determining region 1 (VLCDR1) amino acid sequence of SEQ ID NO: 37 or a sequence having one or two amino acid substitutions, a light chain complementarity determining region 2 (VLCDR2) amino acid sequence of SEQ ID NO: 38 or a sequence having one or two amino acid substitutions, and a light chain complementarity determining region 3 (VLCDR3) amino acid sequence of SEQ ID NO: 39 or a sequence having one or two amino acid substitutions; or
   (iii) a heavy chain variable region (VH) comprising a heavy chain complementarity determining region 1 (VHCDR1) amino acid sequence of SEQ ID NO: 34 or a sequence having one or two amino acid substitutions, a heavy chain complementarity determining region 2 (VHCDR2) amino acid sequence of SEQ ID NO: 44 or a sequence having one or two amino acid substitutions, and a heavy chain complementarity determining region 3 (VHCDR3) amino acid sequence of SEQ ID NO: 36 or a sequence having one or two amino acid substitutions; and
   a light chain variable region (VL) comprising a light chain complementarity determining region 1 (VLCDR1) amino acid sequence of SEQ ID NO: 37 or a sequence having one or two amino acid substitutions, a light chain complementarity determining region 2 (VLCDR2) amino acid sequence of SEQ ID NO: 38 or a sequence having one or two amino acid substitutions, and a light chain complementarity determining region 3 (VLCDR3) amino acid sequence of SEQ ID NO: 48 or a sequence having one or two amino acid substitutions.
2. The antibody molecule or binding fragment thereof of item 1, comprising:
   (i) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 35, and a heavy chain complementarity determining region 3 (VHCDR3) amino acid sequence of SEQ ID NO: 36; and
   a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39; or
   (ii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and
   a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 39; or
   (iii) a heavy chain variable region (VH) comprising a heavy chain complementarity determining region 1 (VHCDR1) amino acid sequence of SEQ ID NO: 34, a heavy chain complementarity determining region 2 (VHCDR2) amino acid sequence of SEQ ID NO: 44, and a heavy chain complementarity determining region 3 (VHCDR3) amino acid sequence of SEQ ID NO: 36; and
   a light chain variable region (VL) comprising a light chain complementarity determining region 1 (VLCDR1) amino acid sequence of SEQ ID NO: 37, a light chain complementarity determining region 2 (VLCDR2) amino acid sequence of SEQ ID NO: 38, and a light chain complementarity determining region 3 (VLCDR3) amino acid sequence of SEQ ID NO: 48.
3. The antibody molecule or binding fragment thereof of items 1 or 2, comprising
   (i) a heavy chain variable region (VH) comprising the amino acid sequence of SEQ ID NO: 40, or an amino acid sequence having at least about 85%, 90%, 95%, or 99% sequence identity to SEQ ID NO: 40, and a light chain variable region (VL) comprising the amino acid sequence of SEQ ID NO: 41, or an amino acid sequence having at least about 85%, 90%, 95%, or 99% sequence identity to SEQ ID NO: 41; or
   (ii) a heavy chain variable region (VH) comprising the amino acid sequence of SEQ ID NO: 45, or an amino acid sequence having at least about 85%, 90%, 95%, or 99% sequence identity to SEQ ID NO: 45, and a light chain variable region (VL) comprising the amino acid sequence of SEQ ID NO: 41, or an amino acid sequence having at least about 85%, 90%, 95%, or 99% sequence identity to SEQ ID NO: 41; or
(iii) a heavy chain variable region (VH) comprising the amino acid sequence of SEQ ID NO: 49, or an amino acid sequence having at least about 85%, 90%, 95%, or 99% sequence identity to SEQ ID NO: 49, and a light chain variable region (VL) comprising the amino acid sequence of SEQ ID NO: 50, or an amino acid sequence having at least about 85%, 90%, 95%, or 99% sequence identity to SEQ ID NO: 50.

4. The antibody molecule or binding fragment thereof of any one of items 1-3, comprising
(i) a heavy chain variable region (VH) comprising the amino acid sequence of SEQ ID NO: 40, and a light chain variable region (VL) comprising the amino acid sequence of SEQ ID NO: 41; or
(ii) a heavy chain variable region (VH) comprising the amino acid sequence of SEQ ID NO: 45, and a light chain variable region (VL) comprising the amino acid sequence of SEQ ID NO: 41; or
(iii) a heavy chain variable region (VH) comprising the amino acid sequence of SEQ ID NO: 49, and a light chain variable region (VL) comprising the amino acid sequence of SEQ ID NO: 50.

5. The antibody molecule or binding fragment thereof of any one of items 1-4, comprising one or more one or more (e.g., 2, 3, 4, 5, 6, 7, 8 or 9) of the following properties:
(i) binds to BK virus serotype I VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(ii) binds to BK virus serotype II VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(iii) binds to BK virus serotype III VP1 with a EC50 of less than about 10 nM, 1 nM, 0.9 nM, 0.8 nM. 0.7 nM, 0.6 nM. 0.5 nM. 0.4 nM. 0.3 nM. 0.2 nM. 0.19 nM. 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(iv) binds to BK virus serotype IV VP1 with a EC50 of less than about 10 nM, 1 nM, 0.9 nM, 0.8 nM, 0.7 nM, 0.6 nM, 0.5 nM, 0.4 nM, 0.3 nM, 0.2 nM, 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, 0.07 nM, 0.06 nM, 0.05 nM, 0.04 nM, 0.03 nM or 0.02 nM e.g., when the antibody molecule or binding fragment thereof is tested as a bivalent molecule using ELISA, e.g., as described in Example 2;
(v) does not bind to JC virus VP1;
(vi) neutralizes BK virus serotype I;
(vii) neutralizes BK virus serotype II;
(viii) neutralizes BK virus serotype III;
(ix) neutralizes BK virus serotype IV.

6. An antibody molecule or a binding fragment thereof that competes for binding to BK virus serotype I VP1, BK virus serotype II VP1, BK virus serotype III VP1, and/or BK virus serotype IV VP1 with the antibody molecule or binding fragment thereof of any one of items 1-5.

7. A pharmaceutical composition comprising the antibody molecule or binding fragment thereof of any one of items 1-6 and a pharmaceutically acceptable carrier, excipient or stabilizer.

8. An antibody molecule or binding fragment thereof according to any one of items 1-6 or a pharmaceutical composition according to item 7 for use in the treatment or prevention of a BK virus infection and/or a BK virus associated disorder.

9. A nucleic acid encoding the antibody heavy and/or light chain variable region of the antibody molecule or binding fragment thereof of any one of items 1-6.

10. An expression vector comprising the nucleic acid of item 9.

11. A host cell comprising the nucleic acid of item 9 or the expression vector of item 10.

12. A method of producing an antibody molecule, the method comprising culturing the host cell of item 11 under conditions suitable for gene expression.

13. A diagnostic composition comprising the antibody molecule or binding fragment thereof of any one of items 1-6.

EXAMPLES

Introductory Comments

The amino acid sequences of the VP1 protein constructs used in the following examples are summarized in Table 1 below.

TABLE 1

| Amino acid sequences of VP1 protein constructs | | | |
|---|---|---|---|
| BKV serotype I | | | |
| SEQ ID NO: 1 | VP1-I | VP1-Pentamer | GGVEVLEVKTGVDAITEVECFLNPEMGDPD ENLRGFSLKLSAENDFSSDSPERKMLPCYS TARIPLPNLNEDLTCGNLLMWEAVTVQTEVI GITSMLNLHAGSQKVHEHGGGKPIQGSNFH FFAVGGDPLEMQGVLMNYRTKYPDGTITPK NPTAQSQVMNTDHKAYLDKNNAYPVECWV PDPSRNENTRYFGTFTGGENVPPVLHVTNT ATTVLLDEQGVGPLCKADSLYVSAADICGL FTNSSGTQQWRGLARYFKIRLRKRSVKNPY |

TABLE 1-continued

Amino acid sequences of VP1 protein constructs

| SEQ ID NO: 2 | VP1-Ia | BK pseudovirus | MAPTKRKGECPGAAPKKPKEPVQVPKLLIK GGVEVLEVKTGVDAITEVECFLNPEMGDPD ENLRGFSLKLSAENDFSSDSPERKMLPCYS TARIPLPNLNEDLTCGNLLMWEAVTVQTEVI GITSMLNLHAGSQKVHEHGGGKPIQGSNFH FFAVGGDPLEMQGVLMNYRTKYPDGTITPK NPTAQSQVMNTDHKAYLDKNNAYPVECWV PDPSRNENTRYFGTFTGGENVPPVLHVTNT ATTVLLDEQGVGPLCKADSLYVSAADICGL FTNSSGTQQWRGLARYFKIRLRKRSVKNPY PISFLLSDLINRRTQRVDGQPMYGMESQVE EVRVFDGTERLPGDPDMIRYIDKQGQLQTK ML |
| --- | --- | --- | --- |
| SEQ ID NO: 3 | VP1-Ib | BK pseudovirus | MAPTKRKGECPGAAPKKPKEPVQVPKLLIK GGVEVLEVKTGLDAITEVECFLNPEMGDPD ENLRGFSLKLSAENDFSSDSPDRKMLPCYS TARIPLPNLNEDLTCGNLLMWEAVTVQTEVI GITSMLNLHAGSQKVHEHGGGKPIQGSNFH FFAVGGDPLEMQGVLMNYRTKYPEGTITPK NPTAQSQVMNTDHKAYLDKNNAYPVECWI PDPSRNENTRYFGTFTGGENVPPVLHVTNT ATTVLLDEQGVGPLCKADSLYVSAADICGL FTNSSGTQQWRGLARYFKIRLRKRSVKNPY PISFLLSDLINRRTQRVDGQPMYGMESQVE EVRVFDGTERLPGDPDMIRYIDKQGQLQTK ML |

BKV serotype II

| SEQ ID NO: 4 | VP1-II | VP1-pentamer | GGVEVLEVKTGVDAITEVECFLNPEMGDPD DNLRGYSLKLTAENAFDSDSPDKKMLPCYS TARIPLPNLNEDLTCGNLLMWEAVTVKTEV IGITSMLNLHAGSQKVHENGGGKPVQGSNF HFFAVGGDPLEMQGVLMNYRTKYPQGTIT PKNPTAQSQVMNTDHKAYLDKNNAYPVEC WIPDPSRNENTRYFGTYTGGENVPPVLHVT NTATTVLLDEQGVGPLCKADSLYVSAADIC GLFTNSSGTQQWRGLARYFKIRLRKRSVKN PY |
| --- | --- | --- | --- |
| SEQ ID NO: 5 | VP1-II | BK pseudovirus | MAPTKRKGECPGAAPKKPKEPVQVPKLLIK GGVEVLEVKTGVDAITEVECFLNPEMGDPD DNLRGYSLKLTAENAFDSDSPDKKMLPCYS TARIPLPNLNEDLTCGNLLMWEAVTVKTEV IGITSMLNLHAGSQKVHENGGGKPVQGSNF HFFAVGGDPLEMQGVLMNYRTKYPQGTIT PKNPTAQSQVMNTDHKAYLDKNNAYPVEC WIPDPSRNENTRYFGTYTGGENVPPVLHVT NTATTVLLDEQGVGPLCKADSLYVSAADIC GLFTNSSGTQQWRGLARYFKIRLRKRSVKN PYPISFLLSDLINRRTQRVDGQPMYGMESQ VEEVRVFDGTEQLPGDPDMIRYIDRQGQLQ TKMV |

BKV serotype III

| SEQ ID NO: 6 | VP1-III | VP1-pentamer | MAPTKRKGECPGAAPKKPKEPVQVPKLLIK GGVEVLEVKTGVDAITEVECFLNPEMGDPD DNLRGYSQHLSAENAFESDSPDRKMLPCY STARIPLPNLNEDLTCGNLLMWEAVTVKTE VIGITSMLNLHAGSQKVHENGGGKPVQGSN FHFFAVGGDPLEMQGVLMNYRTKYPQGTIT PKNPTAQSQVMNTDHKAYLDKNNAYPVEC WIPDPSRNENTRYFGTYTGGENVPPVLHVT NTATTVLLDEQGVGPLCKADSLYVSAADIC GLFTNSSGTQQWRGLARYFKIRLRKRSVKN PYPISFLLSDLINRRTQKVDGQPMYGMESQ VEEVRVFDGTEQLPGDPDMIRYIDRQGQLQ TKMV |
| --- | --- | --- | --- |
| SEQ ID NO: 7 | VP1-III | BK pseudovirus | MAPTKRKGECPGAAPKKPKEPVQVPKLLIK GGVEVLEVKTGVDAITEVECFLNPEMGDPD DNLRGYSQHLSAENAFESDSPDRKMLPCY STARIPLPNLNEDLTCGNLLMWEAVTVKTE VIGITSMLNLHAGSQKVHENGGGKPVQGSN FHFFAVGGDPLEMQGVLMNYRTKYPQGTIT PKNPTAQSQVMNTDHKAYLDKNNAYPVEC |

TABLE 1-continued

| Amino acid sequences of VP1 protein constructs | | | |
|---|---|---|---|
| | | | WIPDPSRNENTRYFGTYTGGENVPPVLHVT<br>NTATTVLLDEQGVGPLCKADSLYVSAADIC<br>GLFTNSSGTQQWRGLARYFKIRLRKRSVKN<br>PYPISFLLSDLINRRTQRVDGQPMYGMESQ<br>VEEVRVFDGTEQLPGDPDMIRYIDRQGQLQ<br>TKMV |
| BKV serotype IV | | | |
| SEQ ID NO: 8 | VP1-IV | VP1-Pentamer | GGVEVLEVKTGVDAITEVECFLNPEMGDPD<br>NDLRGYSLRLTAETAFDSDSPDRKMLPCYS<br>TARIPLPNLNEDLTCGNLLMWEAVTVKTEVI<br>GITSMLNLHAGSQKVHENGGGKPIQGSNFH<br>FFAVGGDPLEMQGVLMNYRTKYPEGTVTP<br>KNPTAQSQVMNTDHKAYLDKNNAYPVECW<br>IPDPSRNENTRYFGTYTGGENVPPVLHVTN<br>TATTVLLDEQGVGPLCKADSLYVSAADICGL<br>FTNSSGTQQWRGLPRYFKIRMRKRSVKNP<br>Y |
| SEQ ID NO: 9 | VP1-IVc | BK pseudovirus | MAPTKRKGECPGAAPKKPKEPVQVPKLLIK<br>GGVEVLEVKTGVDAITEVECFLNPEMGDPD<br>NDLRGYSLRLTAETAFDSDSPDRKMLPCYS<br>TARIPLPNLNEDLTCGNLLMWEAVTVKTEVI<br>GITSMLNLHAGSQKVHENGGGKPIQGSNFH<br>FFAVGGDPLEMQGVLMNYRTKYPEGTVTP<br>KNPTAQSQVMNTDHKAYLDKNNAYPVECW<br>IPDPSKNENTRYFGTYTGGENVPPVLHVTN<br>TATTVLLDEQGVGPLCKADSLYVSAADICGL<br>FTNSSGTQQWRGLPRYFKIRLRKRSVKNPY<br>PISFLLSDLINRRTQRVDGQPMYGMESQVE<br>EVRVFDGTEQLPGDPDMIRYIDRQGQLQTK<br>MV |
| JCV | | | |
| SEQ ID NO: 10 | VP1 | VP1-Pentamer | GGVEVLEVKTGVDSITEVECFLTPEMGDPD<br>EHLRGFSKSISISDTFESDSPNRDMLPCYSV<br>ARIPLPNLNEDLTCGNILMWEAVTLKTEVIG<br>VTSLMNVHSNGQATHDNGAGKPVQGTSFH<br>FFSVGGEALELQGVLFNYRTKYPDGTIFPK<br>NATVQSQVMNTEHKAYLDKNKAYPVECWV<br>PDPTRNENTRYFGTLTGGENVPPVLHITNT<br>ATTVLLDEFGVGPLCKGDNLYLSAVDVCGM<br>FTNRSGSQQWRGLSRYFKVQLRKRRVKNP<br>Y |

Comparative Antibodies

P8D11 (WO 2017/046676) was cloned as described for the other antibodies. VH and VL of P8D11 as described in WO 2017/046676 was fused to the identical constant domains of IgG as described below. Amino acid sequences for comparative antibody P8D11 are summarized in Table 2 below.

Negative control 24C3 is an antibody derived from healthy humans against Tetanus toxoid. The variable fragments were fused to the identical constant domains of IgG as described below.

TABLE 2

| Amino acid sequences for comparative antibody P8D11 (WO 2017/046676) | | |
|---|---|---|
| P8D11 (WO 2017/046676) | | |
| SEQ ID NO: 11 | VHCDR1 (Kabat) | NYWMT |
| SEQ ID NO: 12 | VHCDR2 (Kabat) | NIKKDGSEKYYVDSVRG |
| SEQ ID NO: 13 | VHCDR3 (Kabat) | VRSGRYFALDD |

TABLE 2-continued

Amino acid sequences for comparative
antibody P8D11 (WO 2017/046676)
P8D11 (WO 2017/046676)

| SEQ ID NO: 14 | VLCDR1 (Kabat) | GGDNIGSRPVH |
|---|---|---|
| SEQ ID NO: 15 | VLCDR2 (Kabat) | DDSNRPS |
| SEQ ID NO: 16 | VLCDR3 (Kabat) | QVWSSSTDHP |
| SEQ ID NO: 17 | VH | QVQLVESGGTLVQPGGSLRLSCAASGFTFNNYWMTWV RQAPGKGLEWVANIKKDGSEKYYVDSVRGRFTISRDN AKNSLFLQMNSLRPEDTAVYFCATVRSGRYFALDDWG QGTLVTVSS |
| SEQ ID NO: 18 | VL | QSVLTQPPSVSVAPGKTARITCGGDNIGSRPVHWYQQ KPGQAPILVVYDDSNRPSGIPERFSGSNSGNTATLTI SRVEAGDEADYYCQVWSSSTDHPFGGGTKVTVL |
| SEQ ID NO: 19 | Full length heavy chain | QVQLVESGGTLVQPGGSLRLSCAASGFTFNNYWMTWV RQAPGKGLEWVANIKKDGSEKYYVDSVRGRFTISRDN AKNSLFLQMNSLRPEDTAVYFCATVRSGRYFALDDWG QGTLVTVSSASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKKVEPKSCDK THTCPPCPAPELLGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPAPIEKTI SKAKGQPREPQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPGK |
| SEQ ID NO: 20 | Full length light chain | QSVLTQPPSVSVAPGKTARITCGGDNIGSRPVHWYQQK PGQAPILVVYDDSNRPSGIPERFSGSNSGNTATLTISR VEAGDEADYYCQVWSSSTDHPFGGGTKVTVLGQPKAAP SVTLFPPSSEELQANKATLVCLISDFYPGAVTVAWKAD SSPVKAGVETTTPSKQSNNKYAASSYLSLTPEQWKSH RSYSCQVTHEGSTVEKTVAPTECS |

Antibody Discovery

Example 1

Peripheral blood memory B cells from healthy human donors or kidney transplant recipients were used to prepare antibody repertoire expression libraries by cloning the immunoglobulin light chain and heavy chain variable regions into an expression cassette providing the human immunoglobulin constant heavy region combined with a transmembrane domain derived from human CD8 to allow for mammalian cell display of the antibodies. Screening of the antibody libraries was performed after transduction of the library in HEK 293T cells by antigen-specific sorting using fluorescently labelled VP1-pentamers of BK-Virus.

This sort yielded BK-Virus-specific-antibody-expressing HEK cell clones which were further propagated to upscale antibody production for downstream analysis of antibody properties such as additional binding assays in ELISA or BK-virus neutralization. The neutralizing capacity of the antibodies was tested using BK pseudoviruses (BK-PsV) carrying a luciferase expressing reporter plasmid and wild type BKV. BK-virus-specific antibodies with high affinity and virus neutralizing capacity were then sub-cloned into expression vectors for soluble antibody expression and expressed after transient transfection in HEK 293F or CHO cells. Antibodies were then purified over protein G or Protein A for characterization in the various assays. Amino acid sequences relating to identified antibody 319C07 are summarized in Table 3 below. In addition, variants were prepared and the corresponding amino acid sequences are also summarized in Table 3 below. Amino acid sequences relating to identified antibody 336F07 are summarized in Table 4 below. In addition, variants were prepared and the corresponding amino acid sequences are also summarized in Table 4 below.

TABLE 3

Amino acid sequences for anti-BK virus
antibodies 319C07 and 319C07-var1.

319C07

| SEQ ID NO: 21 | VHCDR1 (Kabat) | AYYWT |
|---|---|---|
| SEQ ID NO: 22 | VHCDR2 | EINHRGYTNYNPSLRG |

TABLE 3-continued

Amino acid sequences for anti-BK virus antibodies 319C07 and 319C07-var1.

| SEQ ID NO: 23 | VHCDR3 (Kabat) | LRSTSGWHDYFDY |
|---|---|---|
| SEQ ID NO: 24 | VLCDR1 (Kabat) | RASQSVSSSYLA |
| SEQ ID NO: 25 | VLCDR2 (Kabat) | GASSRAT |
| SEQ ID NO: 26 | VLCDR3 (Kabat) | LQYGSSPLT |
| SEQ ID NO: 27 | VH | QVQLQQWGAGLLKPSETLSLTCAVYRGSFSAYYWTWFRQPPGKGLEWIGEINHRGYTNYNPSLRGRVSISVDTSKKQFSLKLRSVNAADTAVYYCATLRSTSGWHDYFDYWGQGTLVTVSS |
| SEQ ID NO: 28 | VL | EIVLTQSPGTLSLSPGERATLSCRASQSVSSSYLAWYQQTPGQAPRLLIYGASSRATGIPDRFSGSGSGTDFTLTISRLEPEDFVVYFCLQYGSSPLTFGPGTKVDIK |
| SEQ ID NO: 29 | Full length heavy chain | QVQLQQWGAGLLKPSETLSLTCAVYRGSFSAYYWTWFRQPPGKGLEWIGEINHRGYTNYNPSLRGRVSISVDTSKKQFSLKLRSVNAADTAVYYCATLRSTSGWHDYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 30 | Full length light chain | EIVLTQSPGTLSLSPGERATLSCRASQSVSSSYLAWYQQTPGQAPRLLIYGASSRATGIPDRFSGSGSGTDFTLTISRLEPEDFVVYFCLQYGSSPLTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

319C07-var1

| SEQ ID NO: 21 | VHCDR1 (Kabat) | AYYWT |
|---|---|---|
| SEQ ID NO: 22 | VHCDR2 | EINHRGYTNYNPSLRG |
| SEQ ID NO: 23 | VHCDR3 (Kabat) | LRSTSGWHDYFDY |
| SEQ ID NO: 24 | VLCDR1 (Kabat) | RASQSVSSSYLA |
| SEQ ID NO: 25 | VLCDR2 (Kabat) | GASSRAT |
| SEQ ID NO: 26 | VLCDR3 (Kabat) | LQYGSSPLT |
| SEQ ID NO: 27 | VH | QVQLQQWGAGLLKPSETLSLTCAVYRGSFSAYYWTWFRQPPGKGLEWIGEINHRGYTNYNPSLRGRVSISVDTSKKQFSLKLRSVNAADTAVYYCATLRSTSGWHDYFDYWGQGTLVTVSS |
| SEQ ID NO: 31 | VL | EIVLTQSPGTLSLSPGERATLSCRASQSVSSSYLAWYQQKPGQAPRLLIYGASSRATGIPDRFSGSGSGTDFTLTISRLEPEDFAVYFCLQYGSSPLTFGPGTKVDIK |
| SEQ ID NO: 32 | Full length heavy chain | QVQLQQWGAGLLKPSETLSLTCAVYRGSFSAYYWTWFRQPPGKGLEWIGEINHRGYTNYNPSLRGRVSISVDTSKKQFSLKLRSVNAADTAVYYCATLRSTSGWHDYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTH |

TABLE 3-continued

Amino acid sequences for anti-BK virus
antibodies 319C07 and 319C07-var1.

|  |  |  |
|---|---|---|
|  |  | TCPPCPAPELLGGPSVFLFPPKPKDTLMISRTPEVTCV<br>VVDVSHEDPEVKFNWYVDGVEVHNAKTKPREEQYNSTY<br>RVVSVLTVLHQDWLNGKEYKCKVSNKALPAPIEKTISK<br>AKGQPREPQVYTLPPSREEMTKNQVSLTCLVKGFYPSD<br>IAVEWESNGQPENNYKTTPPVLDSDGSFFLYSKLTVDK<br>SRWQQGNVFSCSVMHEALHNHYTQKSLSLSPGK |
| SEQ ID<br>NO: 33 | Full length<br>light chain | EIVLTQSPGTLSLSPGERATLSCRASQSVSSSYLAWYQQ<br>KPGQAPRLLIYGASSRATGIPDRFSGSGSGTDFTLTISR<br>LEPEDFAVYFCLQYGSSPLTFGPGTKVDIKRTVAAPSVF<br>IFPPSDEQLKSGTASVVCLLNNFYPREAKVQWKVDNALQ<br>SGNSQESVTEQDSKDSTYSLSSTLTLSKADYEKHKVYAC<br>EVTHQGLSSPVTKSFNRGEC |

TABLE 4

Amino acid sequences for anti-BK virus antibodies 336F07, 336F07-
var1 and 336F07-var4.

| 336F07 |  |  |
|---|---|---|
| SEQ ID<br>NO: 34 | VHCDR1<br>(Kabat) | LYAMN |
| SEQ ID<br>NO: 35 | VHCDR2<br>(Kabat) | LISGSGTATYYADSVTG |
| SEQ ID<br>NO: 36 | VHCDR3<br>(Kabat) | TYPTWGGVVIGAIDV |
| SEQ ID<br>NO: 37 | VLCDR1<br>(Kabat) | RASQSIQRWLA |
| SEQ ID<br>NO: 38 | VLCDR2<br>(Kabat) | DASTLES |
| SEQ ID<br>NO: 39 | VLCDR3<br>(Kabat) | QQYNGHAST |
| SEQ ID<br>NO: 40 | VH | EEPLLESGGGLVQPGGSLRLSCAASGFTFRLYAMNWVR<br>QAPGKGLEWVSLISGSGTATYYADSVTGRFSISRDNYK<br>NRVYLQMDSLRADDTATYYCAKTYPTWGGVVIGAIDVW<br>GQGTTVTVSS |
| SEQ ID<br>NO: 41 | VL | DIQMTQSPSTLSASVGDRVTITCRASQSIQRWLAWHQQ<br>KPGRAPKVLIHDASTLESGVPSRFSGSGSGTEFTLTIS<br>SLQPDDFATYYCQQYNGHASTFGPGTKVDIK |
| SEQ ID<br>NO: 42 | Full length<br>heavy<br>chain | EEPLLESGGGLVQPGGSLRLSCAASGFTFRLYAMNWVR<br>QAPGKGLEWVSLISGSGTATYYADSVTGRFSISRDNYK<br>NRVYLQMDSLRADDTATYYCAKTYPTWGGVVIGAIDVW<br>GQGTTVTVSSASTKGPSVFPLAPSSKSTSGGTAALGCL<br>VKDYFPEPVTVSWNSGALTSGVHTFPAVLQSSGLYSLS<br>SWTVPSSSLGTQTYICNVNHKPSNTKVDKKVEPKSCDK<br>THTCPPCPAPELLGGPSVFLFPPKPKDTLMISRTPEVT<br>CVVVDVSHEDPEVKFNWYVDGVEVHNAKTKPREEQYNS<br>TYRVVSVLTVLHQDWLNGKEYKCKVSNKALPAPIEKTI<br>SKAKGQPREPQVYTLPPSREEMTKNQVSLTCLVKGFYP<br>SDIAVEWESNGQPENNYKTTPPVLDSDGSFFLYSKLTV<br>DKSRWQQGNVFSCSVMHEALHNHYTQKSLSLSPGK |
| SEQ ID<br>NO: 43 | Full length<br>light chain | DIQMTQSPSTLSASVGDRVTITCRASQSIQRWLAWHQQ<br>KPGRAPKVLIHDASTLESGVPSRFSGSGSGTEFTLTIS<br>SLQPDDFATYYCQQYNGHASTFGPGTKVDIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC |
| 336F07-var1 |  |  |
| SEQ ID<br>NO: 34 | VHCDR1<br>(Kabat) | LYAMN |
| SEQ ID<br>NO: 44 | VHCDR2<br>(Kabat) | LISGSGTATYYADSVKG |

TABLE 4-continued

Amino acid sequences for anti-BK virus antibodies 336F07, 336F07-var1 and 336F07-var4.

| SEQ ID NO: 36 | VHCDR3 (Kabat) | TYPTWGGVVIGAIDV |
|---|---|---|
| SEQ ID NO: 37 | VLCDR1 (Kabat) | RASQSIQRWLA |
| SEQ ID NO: 38 | VLCDR2 (Kabat) | DASTLES |
| SEQ ID NO: 39 | VLCDR3 (Kabat) | QQYNGHAST |
| SEQ ID NO: 45 | VH | EEPLLESGGGLVQPGGSLRLSCAASGFTFRLYAMNWVRQAPGKGLEWVSLISGSGTATYYADSVKGRFSISRDNSKNRVYLQMSSLRADDTATYYCAKTYPTWGGVVIGAIDVWGQGTTVTVSS |
| SEQ ID NO: 41 | VL | DIQMTQSPSTLSASVGDRVTITCRASQSIQRWLAWHQQKPGRAPKVLIHDASTLESGVPSRFSGSGSGTEFTLTISSLQPDDFATYYCQQYNGHASTFGPGTKVDIK |
| SEQ ID NO: 46 | Full length heavy chain | EEPLLESGGGLVQPGGSLRLSCAASGFTFRLYAMNWVRQAPGKGLEWVSLISGSGTATYYADSVKGRFSISRDNSKNRVYLQMSSLRADDTATYYCAKTYPTWGGVVIGAIDVWGQGTTVTVSSASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 47 | Full length light chain | DIQMTQSPSTLSASVGDRVTITCRASQSIQRWLAWHQQKPGRAPKVLIHDASTLESGVPSRFSGSGSGTEFTLTISSLQPDDFATYYCQQYNGHASTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

336F07-var4

| SEQ ID NO: 34 | VHCDR1 (Kabat) | LYAMN |
|---|---|---|
| SEQ ID NO: 44 | VHCDR2 (Kabat) | LISGSGTATYYADSVKG |
| SEQ ID NO: 36 | VHCDR3 (Kabat) | TYPTWGGVVIGAIDV |
| SEQ ID NO: 37 | VLCDR1 (Kabat) | RASQSIQRWLA |
| SEQ ID NO: 38 | VLCDR2 (Kabat) | DASTLES |
| SEQ ID NO: 48 | VLCDR3 (Kabat) | QQYSGHAST |
| SEQ ID NO: 49 | VH | EEPLLESGGGLVQPGGSLRLSCAASGFTFRLYAMNWVRQAPGKGLEWVSLISGSGTATYYADSVKGRFTISRDNSKNRVYLQMSSLRADDTAVYYCAKTYPTWGGVVIGAIDVWGQGTTVTVSS |
| SEQ ID NO: 50 | VL | DIQMTQSPSTLSASVGDRVTITCRASQSIQRWLAWHQQKPGKAPKLLIHDASTLESGVPSRFSGSGSGTEFTLTISSLQPDDFATYYCQQYSGHASTFGPGTKVDIK |
| SEQ ID NO: 51 | Full length heavy chain | EEPLLESGGGLVQPGGSLRLSCAASGFTFRLYAMNWVRQAPGKGLEWVSLISGSGTATYYADSVKGRFTISRDNSKNRVYLQMSSLRADDTAVYYCAKTYPTWGGVVIGAIDVWGQGTTVTVSSASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKKVEPKSCDKTHTCPPCPAPELLGGPSVFLFPPKPKDTLMISRTPEVT |

TABLE 4-continued

Amino acid sequences for anti-BK virus antibodies 336F07, 336F07-var1 and 336F07-var4.

|  |  |  |
|---|---|---|
|  |  | CVVVDVSHEDPEVKFNWYVDGVEVHNAKTKPREEQYNS<br>TYRVVSVLTVLHQDWLNGKEYKCKVSNKALPAPIEKTI<br>SKAKGQPREPQVYTLPPSREEMTKNQVSLTCLVKGFYP<br>SDIAVEWESNGQPENNYKTTPPVLDSDGSFFLYSKLTV<br>DKSRWQQGNVFSCSVMHEALHNHYTQKSLSLSPGK |
| SEQ ID<br>NO: 52 | Full length<br>light chain | DIQMTQSPSTLSASVGDRVTITCRASQSIQRWLAWHQQ<br>KPGKAPKLLIHDASTLESGVPSRFSGSGSGTEFTLTIS<br>SLQPDDFATYYCQQYSGHASTFGPGTKVDIKRTVAAPS<br>VFIFPPSDEQLKSGTASVVCLLNNFYPREAKVQWKVDN<br>ALQCEVTHQGLSSPVTKSFNRGEC |

Assays

Example 2—Binding to VP1-Pentamer in ELISA

Material and Methods

The binding of anti-BK virus antibodies to BKV-VP1 pentamers was analyzed by ELISA. Briefly, Costar® 96 well Assay Plates, half area high binding plates (Corning Inc. #3690) were coated with 30 µl/well of 1 µg/ml BKV-VP1 pentamers overnight at 4° C. Subsequently, the plate was blocked using 5% skim milk powder (Rapilait, Migros #7610200017598) diluted in PBS. Antibodies were serially diluted in PBS with 0.5% skim milk powder and added to the antigen-coated plates for 1.5 h. Then, plates were washed with PBS 0.05% Tween20 (AppliChem, A4974) and incubated with enzyme-labelled secondary antibody (HRP-conjugated goat anti-human IgG, Jackson-Immuno #109-035-098) diluted 1:10'000 in PBS with 0.5% skim milk powder for 45 min. Plates were washed three times with PBS containing 0.05% Tween 20. The reaction was developed using 30 µl/well TMB liquid substrate (Sigma-Aldrich, #T0440) and stopped with 15 µl/well $H_2SO_4$. Absorbance was detected at 450 nm (Tecan, CM INFINITE MONO 200). Data were fitted and apparent EC50 ELISA values ($EC50_E$) were determined by three-parameter analysis in GraphPad Prism (GraphPad Software).

Results

The antibody 319C07 showed strong and selective binding to all BKV-VP1 serotypes (FIG. 1, $EC50_E$ values below). Compared to comparative antibody P8D11, antibody 319C07 showed higher affinity for serotype I, II and IV and showed a comparable affinity on BKV-VP1-serotype III.

| $EC50_E$ (nM) | VP1-I | VP1-II | VP1-III | VP1-IV |
|---|---|---|---|---|
| 319C07 | 0.05 | 0.06 | 0.06 | 0.06 |
| P8D11 | 0.14 | 0.19 | 0.07 | 0.12 |

Also the antibody 336F07 showed strong and selective binding to all BKV-VP1 serotypes (FIG. 1, $EC50_E$ values below). Compared to comparative antibody P8D11, antibody 336F07 showed higher affinity on all four serotypes.

| $EC50_E$ (nM) | VP1-I | VP1-II | VP1-III | VP1-IV |
|---|---|---|---|---|
| 336F07 | 0.07 | 0.03 | 0.02 | 0.03 |
| P8D11 | 0.14 | 0.19 | 0.07 | 0.12 |

Example 3—Neutralization of BK-Pseudovirus by Anti-BK Virus Antibodies

Material and Methods

BK Pseudovirus (BK-PsV) carrying the NanoLuc reporter gene was produced as described (Pastrana et al, J Virol, 2013 September; 87(18):10105-13). Five different genotypes were produced: BKV-la (BK-D; JF894228), BKV-Ib2 (Pit-tVR2; DQ989796) BKV-II (Q85238; CAA79596), BKV-III (QOPDA6; BAF03017) and BKV-IVc2 (A-66H; AB369093). VP1 was purified over Agarose gel beads as described (Buck et al, J Virol, 2008 June; 82(11):5190-7 and Buck et al, Curr Protoc Cell Biol, 2007 December; Chapter 26; 26.21). Infectious virus titer was determined on 293TT cells. Different dilutions of the BK-PsV were tested in a 96 well plate with and without inhibitor. The dilution selected for further assays resulted in a high luminescence signal in non-inhibited cells.

20'000 cells (293TT) were seeded in a 96 well plate using DMEM containing 9% FBS, HEPES and Penicillin/Streptavidin. After a 5 h incubation, antibodies in various concentrations and a fix amount of BK-Pseudovirus was added to each well and the plate was incubated at 37 C, 5% C02. After 3 days of incubation luciferase activity in the supernatant fluid was measured using the NanoGlo™ assay reagent (Promega, #N1130).

40 ul of cell culture or virus-cell-antibody-co-culture-supernatant was transferred into white bottom 96 well plates, 40 ul of NanoGlo™ substrate was added and incubated for 2 minutes before determination of luciferase activity using a luminescence reader (BioTek Synergy). Data were plotted on a Signal vs antibody concentration curve. IC50 values were determined by GraphPad Prism using non-linear regression (curve fit) and the formula "log(inhibitor) vs normalized response (variable slope)" (GraphPad Software).

Results

319C07 and the variant 319C07-var1 show strong inhibition of BK-Pseudovirus from all serotypes. 319C07 outperforms P8D11 significantly (FIG. 2, IC50 values below).

| IC50 (nM) | Ia | Ib | II | III | IV |
|---|---|---|---|---|---|
| 319C07 | 0.007 | 0.007 | 0.010 | 0.058 | 0.032 |
| P8D11 | 0.391 | 0.392 | 0.565 | 0.176 | 2.906 |

Also antibody 336F07 and the variants 336F07-var1 and 336F07-var4 show strong inhibition of BK-Pseudovirus from all serotypes. 336F07 outperforms P8D11 significantly (FIG. 2, IC50 values below).

| IC50 (nM) | Ia | Ib | II | III | IV |
|---|---|---|---|---|---|
| 336F07 | 0.094 | 0.103 | 0.020 | 0.019 | 0.018 |
| P8D11 | 0.391 | 0.392 | 0.565 | 0.176 | 2.906 |

Example 4—Long-Term Virus Neutralization by Anti-BK Virus Antibodies

Material and Methods

To address long-term virus neutralization by anti-BK virus antibodies in vitro, repetitive cycles of co-cultures of human primary renal proximal tubular epithelial cells (HPRTEC), wild type BK virus strain I (ATCC® VR-837™) and anti-BK virus antibodies were used. At the start of the study, anti-BK virus antibodies were added at three distinct concentrations corresponding to their EC95; EC50 and EC5 viral inhibition potency to cell-virus co-cultures for 1 week. After this period virus was harvested from the cells and remaining supernatant by 3 freeze thaw cycles. 10 ul of this virus extract was then added to freshly seeded HRPTEC cells in the presence of antibodies at the various concentrations. After 2 weeks of inoculation virus load was again quantified and virus extracts were generated to be used in the next infection cycle. This procedure was repeated 3 times resulting in a total of 8 weeks of co-culture.

The assay was performed in triplica in 96 well flat bottom cell culture plates. Quantification of viral load in the culture supernatant was performed by harvesting 15 µl of media which was then heat-inactivated at 95° C. for 10 min and used for qPCR with primers 5'-GGATGGGCAGCC-TATGTATG-3' (SEQ ID NO: 53), and 5'-TCATAT-CTGGGTCCCCTGGA-3' (SEQ ID NO: 54) and a TaqMan™ probe FAM-AGGGTGTTTGATGGCACAGA-TAMRA (SEQ ID NO: 55). PCR was performed using PerfeCTa qPCR ToughMix (Quantabio, #95140) with following conditions: 95° C. for 8 min and 40 cycles of 95° C. for 10 sec and 60° C. for 60 sec.

Results

Antibody 319C07 shows a more complete neutralization of the virus compared to P8D11. This becomes most apparent when looking at the last infection-neutralization cycle after 8 weeks where at concentrations corresponding to EC95 and EC50 no virus could be detected anymore whereas P8D11 shows measurable virus loads in both EC95 and EC50. (FIG. 3, P8D11 is labelled with "BM2" in this figure).

Also antibody 336F07 shows a more complete neutralization of the virus compared to P8D11. This becomes most apparent when looking at the last infection-neutralization cycle after 8 weeks (FIG. 3, P8D11 is labelled with "BM2" in this figure).

Example 5—Anti-BK Virus Antibodies Bind to a Conformational Epitope

Material and Methods

In order to determine whether the anti-BK virus antibodies are binding to a conformational epitope, dot blots of VP1 in native state and in denatured state were performed. BKV-VP1 pentamers of serotypes I, II, III and IV were spotted to a nitrocellulose membrane either in their native form or after chemical and thermal denaturation using Tris buffer containing SDS and β-Mercaptoethanol and heating at 85° C. for 5 min. Both membranes were incubated with the anti-BK virus antibodies and their binding was revealed using HRP-conjugated secondary antibodies directed against human Fc. Detection was done using a colorimetric substrate (Sigma Fast DAB).

Results

Antibody 319C07 and antibody 336F07 show selective binding to a conformational epitope (FIG. 4). Due to absence of staining of denatured antigen, binding to a linear epitope can be excluded. Commercially available control antibody (Ab53977, Abcam, rabbit-IgG) known to recognize a linear epitope, detected both the denatured and non-denatured VP1.

Example 6—Binding to Mutations of BKV-VP1-Pentamer and to JCV-VP1 Pentamer in ELISA Material and Methods The VP1-Serotype Ib wild type sequence was used as the basis for the introduction of mutations at various positions. Likewise, VP1 of the JC virus was used. The binding of anti-BK virus antibodies to wild type and variant VP1 pentamers was analyzed by ELISA. Briefly, Costar® Assay Plate 96 well, half area high binding plates (Corning Inc. #3690) were coated with 30 µl/well of 1 µg/ml BKV-VP1 pentamer variants overnight at 4° C. After 16 h, non-specific binding was blocked using 5% skim milk powder (Rapilait, Migros #7610200017598) diluted in PBS. Antibodies were serially diluted from 67 nM down to 0.02 nM in PBS containing 0.5% skim milk powder and incubated on the antigen-coated plates for 1.5 h. Plates were then washed three times with PBS 0.05% Tween20 (AppliChem, A4974) and then incubated with secondary antibody (HRP-conjugated goat anti-human IgG, Jackson-Immuno #109-035-098) diluted 1:10'000 in PBS with 0.5% skim milk powder for 45 min. HRP activity of the bound secondary antibodies was revealed using 30 µl/well TMB liquid substrate (Sigma-Aldrich, #T0440). The reaction was stopped after 2.5 min by addition of 15 µl/well 1M H2SO4. Absorbance was detected at 450 nm (Tecan, CM INFINITE MONO 200). Data were plotted and EC50 values were determined by three-parameter analysis in GraphPad Prism (GraphPad Software) and are referred to as EC50ELISA (EC50E).

Results

Binding to mutant forms of BKV VP1 in comparison to wild type VP1 and to VP1 of the closely related JC polyoma virus was tested for antibody 319C07 in comparison to antibody P8D11. Antibody 319C07 does not bind at all to VP1 of the JC virus whereas antibody P8D11 shows weak but significant binding. If amino acids at position N62, D175 or S275 is mutated to alanine, 319C07 shows a slightly reduced binding affinity. Changing amino acid K172 to alanine does not lower the binding. P8D11 on the other hand, shows reduced binding to the VP1-I-K172A mutant, while binding is not affected to N62A, D175A or S275A mutations. Compared to antibody P8D11, 319C07 shows here a clearly distinct pattern suggesting that it interacts with different amino acids of VP1 compared to P8D11 (FIG. 5).

Binding to mutant forms of BKV VP1 in comparison to wild type VP1 and to VP1 of the closely related JC polyoma virus was also tested for antibody 336F07 in comparison to antibody P8D11. Antibody 336F07 does not bind at all to VP1 of the JC virus whereas antibody P8D11 shows weak but significant binding. If amino acids at position N62 or E73 is mutated, 336FC07 shows a slightly reduced binding affinity. Changing amino acid K172 to alanine does not lower the binding. P8D11 on the other hand, shows reduced binding to the VP1-I-K172A mutant, while binding is not affected to N62A or E73Q mutations. Compared to antibody P8D11, 336F07 shows here a clearly distinct pattern suggesting that it interacts with different amino acids of VP1 compared to P8D11 (FIG. 5).

Example 7—Inhibition of Virus Spread from Infected HRPTEC Cells

Material and Methods

Primary Human Renal Proximal Tubule Epithelial Cells (HRPTEC) were infected with BKV (strain 33-1, ATCC® 45024™). After 5 days, cells were gently scratched with a cell scraper and extensively washed with PBS to remove all cell free virus. Cells were then added to wells containing adherent growing HRPTEC and various dilutions of BKV-neutralizing antibody. 8 days after inoculation of cells 10 µl of supernatant fluid was removed from each well and viral load was determined using quantitative PCR using primers 5'-GGATGGGCAGCCTATGTATG-3' (SEQ ID NO: 53), 5'-TCATATCTGGGTCCCCTGGA-3' (SEQ ID NO: 54) and probe FAM-5'-AGGGTGTTTGATGGCACAGA-3'-TAMRA (SEQ ID NO: 55) as described (Martelli et al., Viruses, 2018 Aug. 30; 10(9):466).

Results

Antibody 319C07 is showing around 100 fold superiority over P8D11 for inhibition of BKV spread among HRPTEC; also antibody 336F07 is showing significant superiority over P8D11 for inhibition of BKV spread among HRPTEC (FIG. 6, P8D11 is labelled with "BM2" in this figure).

Example 8—Antibody-Dependent-Cellular-Cytotoxicity (ADCC)

Material and Methods

HRPTEC seeded in flat bottom 96 well plates either infected with wild type BK virus strain I (ATCC® VR-837™) or left uninfected were used as target cells. As effector cells, engineered Jurkat cells, components of the ADCC Reporter Bioassay G7015 from Promega were used. In this assay, as a surrogate for ADCC activity, Fc-γRIIIa signalling by the effector cells is quantified through a luminescence readout. Anti-BKV or control antibodies in serial dilutions were added at to the HPRTEC culture together with the effector cells and incubated for 6 h prior to developing and measuring the bioluminescence as described by the assay kit manufacturer.

Results

319C7 and 336F07 showed comparable ADCC activity on infected HRPTEC which in turn was comparable to that of P8D11. No ADCC was observed on HRPTEC that were left uninfected with either 319C7 and 336F07 or P8D11 (FIG. 7).

Example 9—Complement-Dependent-Toxicity

Material and Methods

HRPTEC seeded in flat bottom 96 well plates either infected with wild type BK virus strain I (ATCC® VR-837™) or left uninfected were used as target cells. Cells were incubated with anti-BKV antibodies at serial dilutions starting with 100 µg/ml and 20% human serum overnight and cell viability was quantified by determining the ratio of living cells using the FSC/SSC criterium in a cytometer.

Results

319C7 and 336F07 showed no CDC activity at a concentration of 100 µg/ml on infected HRPTEC and the same observation was made with antibody P8D11 and control antibody Rituximab directed against an irrelevant target on HRPTEC (FIG. 8).

The invention claimed is:

1. An anti-BK virus antibody molecule or binding fragment thereof comprising:
   a heavy chain variable region (VH) comprising a heavy chain complementarity determining region 1 (VHCDR1) amino acid sequence of SEQ ID NO: 21, a heavy chain complementarity determining region 2 (VHCDR2) amino acid sequence of SEQ ID NO: 22, and a heavy chain complementarity determining region 3 (VHCDR3) amino acid sequence of SEQ ID NO: 23; and
   a light chain variable region (VL) comprising a light chain complementarity determining region 1 (VLCDR1) amino acid sequence of SEQ ID NO: 24, a light chain complementarity determining region 2 (VLCDR2) amino acid sequence of SEQ ID NO: 25, and a light chain complementarity determining region 3 (VLCDR3) amino acid sequence of SEQ ID NO: 26.

2. The antibody molecule or binding fragment thereof of claim 1 comprising:
   (i) a heavy chain variable region (VH) comprising the amino acid sequence of SEQ ID NO: 27, or an amino acid sequence having at least about 85% sequence identity to SEQ ID NO: 27, and a light chain variable region (VL) comprising the amino acid sequence of SEQ ID NO: 28, or an amino acid sequence having at least about 85% sequence identity to SEQ ID NO: 28; or
   (ii) a heavy chain variable region (VH) comprising the amino acid sequence of SEQ ID NO: 27, or an amino acid sequence having at least about 85% sequence identity to SEQ ID NO: 27, and a light chain variable region (VL) comprising the amino acid sequence of SEQ ID NO: 31, or an amino acid sequence having at least about 85% sequence identity to SEQ ID NO: 31.

3. The antibody molecule or binding fragment thereof of claim 1 comprising
   (i) a heavy chain variable region (VH) comprising the amino acid sequence of SEQ ID NO: 27, and a light chain variable region (VL) comprising the amino acid sequence of SEQ ID NO: 28; or
   (ii) a heavy chain variable region (VH) comprising the amino acid sequence of SEQ ID NO: 27, and a light chain variable region (VL) comprising the amino acid sequence of SEQ ID NO: 31.

4. The antibody molecule or binding fragment thereof of claim 1 comprising one or more of the following properties:
   (i) binds to BK virus serotype I VP1 with an EC50 of less than about 10 nM when the antibody molecule or binding fragment thereof is tested as a bivalent molecule using an ELISA assay;
   (ii) binds to BK virus serotype II VP1 with an EC50 of less than about 10 nM when the antibody molecule or binding fragment thereof is tested as a bivalent molecule using an ELISA assay;
   (iii) binds to BK virus serotype III VP1 with an EC50 of less than about 10 nM when the antibody molecule or binding fragment thereof is tested as a bivalent molecule using an ELISA assay;
   (iv) binds to BK virus serotype IV VP1 with an EC50 of less than about 10 nM when the antibody molecule or binding fragment thereof is tested as a bivalent molecule using an ELISA assay;
   (v) does not bind to JC virus VP1;
   (vi) neutralizes BK virus serotype I;
   (vii) neutralizes BK virus serotype II;
   (viii) neutralizes BK virus serotype III; or
   (ix) neutralizes BK virus serotype IV.

5. A pharmaceutical composition comprising the antibody molecule or binding fragment thereof of claim 1 and a pharmaceutically acceptable carrier, excipient or stabilizer.

6. A method of treating a BK virus infection and/or a BK virus associated disorder, the method comprising administering to a subject in need thereof an antibody molecule or binding fragment thereof according to claim 1.

7. A nucleic acid encoding the heavy and/or light chain variable region of the antibody molecule or binding fragment thereof of claim 1.

8. An expression vector comprising the nucleic acid of claim.

9. A host cell comprising the nucleic acid of claim.

10. A method of producing an antibody molecule, the method comprising culturing the host cell of claim 9 under conditions suitable for gene expression.

11. A diagnostic composition comprising the antibody molecule or binding fragment thereof of claim 1.

12. A method of treating a BK virus infection and/or a BK virus associated disorder, the method comprising administering to a subject in need thereof a pharmaceutical composition according to claim 5.

13. A host cell comprising the expression vector of claim 8.

14. The antibody molecule or binding fragment thereof of claim 2 comprising:
   (i) a heavy chain variable region (VH) comprising the amino acid sequence of SEQ ID NO: 27, or an amino acid sequence having at least about 90% sequence identity to SEQ ID NO: 27, and a light chain variable region (VL) comprising the amino acid sequence of SEQ ID NO: 28, or an amino acid sequence having at least about 90% sequence identity to SEQ ID NO: 28, or
   (ii) a heavy chain variable region (VH) comprising the amino acid sequence of SEQ ID NO: 27, or an amino acid sequence having at least about 90% sequence identity to SEQ ID NO: 27, and a light chain variable region (VL) comprising the amino acid sequence of SEQ ID NO: 31, or an amino acid sequence having at least about 90% sequence identity to SEQ ID NO: 31.

15. The antibody molecule or binding fragment thereof of claim 2 comprising:
   (i) a heavy chain variable region (VH) comprising the amino acid sequence of SEQ ID NO: 27, or an amino acid sequence having at least about 95% sequence identity to SEQ ID NO: 27, and a light chain variable region (VL) comprising the amino acid sequence of SEQ ID NO: 28, or an amino acid sequence having at least about 95% sequence identity to SEQ ID NO: 28, or
   (ii) a heavy chain variable region (VH) comprising the amino acid sequence of SEQ ID NO: 27, or an amino acid sequence having at least about 95% sequence identity to SEQ ID NO: 27, and a light chain variable region (VL) comprising the amino acid sequence of SEQ ID NO: 31, or an amino acid sequence having at least about 95% sequence identity to SEQ ID NO: 31.

16. The antibody molecule or binding fragment thereof of claim 2 comprising:
   (i) a heavy chain variable region (VH) comprising the amino acid sequence of SEQ ID NO: 27, or an amino acid sequence having at least about 99% sequence identity to SEQ ID NO: 27, and a light chain variable region (VL) comprising the amino acid sequence of SEQ ID NO: 28, or an amino acid sequence having at least about 99% sequence identity to SEQ ID NO: 28, or
   (ii) a heavy chain variable region (VH) comprising the amino acid sequence of SEQ ID NO: 27, or an amino acid sequence having at least about 99% sequence identity to SEQ ID NO: 27, and a light chain variable region (VL) comprising the amino acid sequence of SEQ ID NO: 31, or an amino acid sequence having at least about 99% sequence identity to SEQ ID NO: 31.

* * * * *

UNITED STATES PATENT AND TRADEMARK OFFICE
CERTIFICATE OF CORRECTION

| | |
|---|---|
| PATENT NO. | : 11,919,943 B2 |
| APPLICATION NO. | : 18/049559 |
| DATED | : March 5, 2024 |
| INVENTOR(S) | : Weber et al. |

It is certified that error appears in the above-identified patent and that said Letters Patent is hereby corrected as shown below:

On the Title Page

Item (30), should read:
-- (30) Foreign Application Priority Data
June 9, 2020 (EP)............... 20179041
June 9, 2020 (EP)............... 20179044 --.

In the Claims

In Claim 8, Column 57, Line 12, "of claim." should read -- of claim 7. --.

In Claim 9, Column 57, Line 13, "of claim." should read -- of claim 7. --.

Signed and Sealed this
Fifth Day of November, 2024

Katherine Kelly Vidal
*Director of the United States Patent and Trademark Office*